US009957502B2

(12) United States Patent
Schatz et al.

(10) Patent No.: US 9,957,502 B2
(45) Date of Patent: *May 1, 2018

(54) NUCLEIC ACID SYNTHESIS METHODS

(75) Inventors: Octavian Schatz, Altomünster (DE); Timothy O'Connell, Fürstenfeldbruck (DE)

(73) Assignee: SLONING BIOTECHNOLOGY GMBH, Planegg (DE)

( * ) Notice: Subject to any disclaimer, the term of this patent is extended or adjusted under 35 U.S.C. 154(b) by 917 days.

This patent is subject to a terminal disclaimer.

(21) Appl. No.: 10/496,263

(22) PCT Filed: Nov. 22, 2002

(86) PCT No.: PCT/EP02/13154
§ 371 (c)(1),
(2), (4) Date: Jan. 27, 2006

(87) PCT Pub. No.: WO03/044193
PCT Pub. Date: May 30, 2003

(65) Prior Publication Data
US 2008/0044862 A1    Feb. 21, 2008

(30) Foreign Application Priority Data
Nov. 22, 2001 (EP) .................... 01127864

(51) Int. Cl.
| C12Q 1/68 | (2018.01) |
| C12P 19/34 | (2006.01) |
| C12N 9/00 | (2006.01) |
| C07H 21/04 | (2006.01) |
| C12N 15/10 | (2006.01) |
| C12N 15/66 | (2006.01) |

(52) U.S. Cl.
CPC ......... *C12N 15/1093* (2013.01); *C12N 15/10* (2013.01); *C12N 15/66* (2013.01); *C12P 19/34* (2013.01)

(58) Field of Classification Search
None
See application file for complete search history.

(56) References Cited

U.S. PATENT DOCUMENTS

| 4,652,639 A | 3/1987 | Stabinsky | |
| 5,093,251 A | 3/1992 | Richards | |
| 5,132,215 A | 7/1992 | Jayaraman | |
| 5,397,698 A | 3/1995 | Goodman et al. | |
| 5,508,169 A * | 4/1996 | Deugau et al. | 435/6 |
| 5,710,000 A | 1/1998 | Sapolsky | |
| 5,770,365 A | 6/1998 | Lane et al. | |
| 5,858,656 A * | 1/1999 | Deugau et al. | 435/6 |
| 5,888,737 A | 3/1999 | DuBridge et al. | |
| 5,981,190 A | 11/1999 | Israel | |
| 6,110,668 A | 8/2000 | Strizhov | |
| 6,472,184 B1 | 10/2002 | Hegemann | |
| 6,485,944 B1 | 11/2002 | Church et al. | |
| 7,695,906 B2 * | 4/2010 | Schatz | C12N 15/10 435/6.11 |
| 8,092,991 B2 * | 1/2012 | Schatz | C12N 15/10 435/6.12 |
| 2003/0219781 A1 | 11/2003 | Frey | |
| 2006/0115850 A1 | 6/2006 | Schatz et al. | |
| 2006/0194202 A1 | 8/2006 | Schatz et al. | |
| 2008/0044862 A1 | 2/2008 | Schatz | |

FOREIGN PATENT DOCUMENTS

| EP | 0 245 130 | 4/1987 |
| EP | 245130 A1 | 11/1987 |
| EP | 0533838 | 3/1993 |
| EP | 1411122 | 4/2004 |
| WO | WO93/19202 | 9/1993 |
| WO | WO95/17413 | 6/1995 |
| WO | WO 96/12014 | 4/1996 |
| WO | 9815567 | 4/1998 |
| WO | WO98/10095 | 12/1998 |
| WO | WO 99/47536 | 9/1999 |
| WO | WO99/47536 | 9/1999 |
| WO | WO 00/75368 A2 | 12/2000 |
| WO | WO 01/61036 | 8/2001 |
| WO | WO 01/61036 A2 | 8/2001 |
| WO | WO 01/75180 | 10/2001 |
| WO | WO 01/75180 A2 | 10/2001 |
| WO | WO 00/75368 | 12/2002 |

OTHER PUBLICATIONS

"Human Genome Project," Wikipedia.com, accessed Jun. 7, 2013.*
"Sequenced Plant Genomes," GenomeEvolution.org, (accessed Feb. 23, 2014).*
"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Mar. 8, 2013).*
"Mammal," (Wikipedia.com; accessed Sep. 22, 2011).*
"Murinae," (Wikipedia.com, accessed Mar. 18, 2013).*
"List of sequenced bacterial genomes" (Wikipedia.com; accessed Jan. 24, 2014).*
Kato, K. et al., Description of the Entire MRNA Population by a 3' End cDNA Fragment Generated by Class IIS Restriction Enzymes, *Nucleic Acids Research*; 23(18):3685-3690 (1995).
Padgett K. A. et al., Creating Seamless Junctions Independent of Restriction Sites in PCR Cloning, Gene; 168:31-35 (1996).

(Continued)

*Primary Examiner* — Bradley L Sisson
(74) *Attorney, Agent, or Firm* — Licata & Tyrrell P.C.

(57) ABSTRACT

The present invention relates to a single-stranded nucleic acid molecule for use in a method for the production of a nucleic acid, whereby the nucleic acid molecule comprises a part A and a part B, whereby part A comprises a sequence, which corresponds at least to a partial sequence of the recognition site of a type IIS restriction enzyme, and part B comprises an arbitrary but defined sequence of nucleotides. By using such nucleic acid molecules it is possible to assemble different fragments in a sequence-independent manner and thus conduct the synthesis of a nucleic acid with recourse to standardized elements.

21 Claims, 23 Drawing Sheets

(56) References Cited

OTHER PUBLICATIONS

Figure 1:
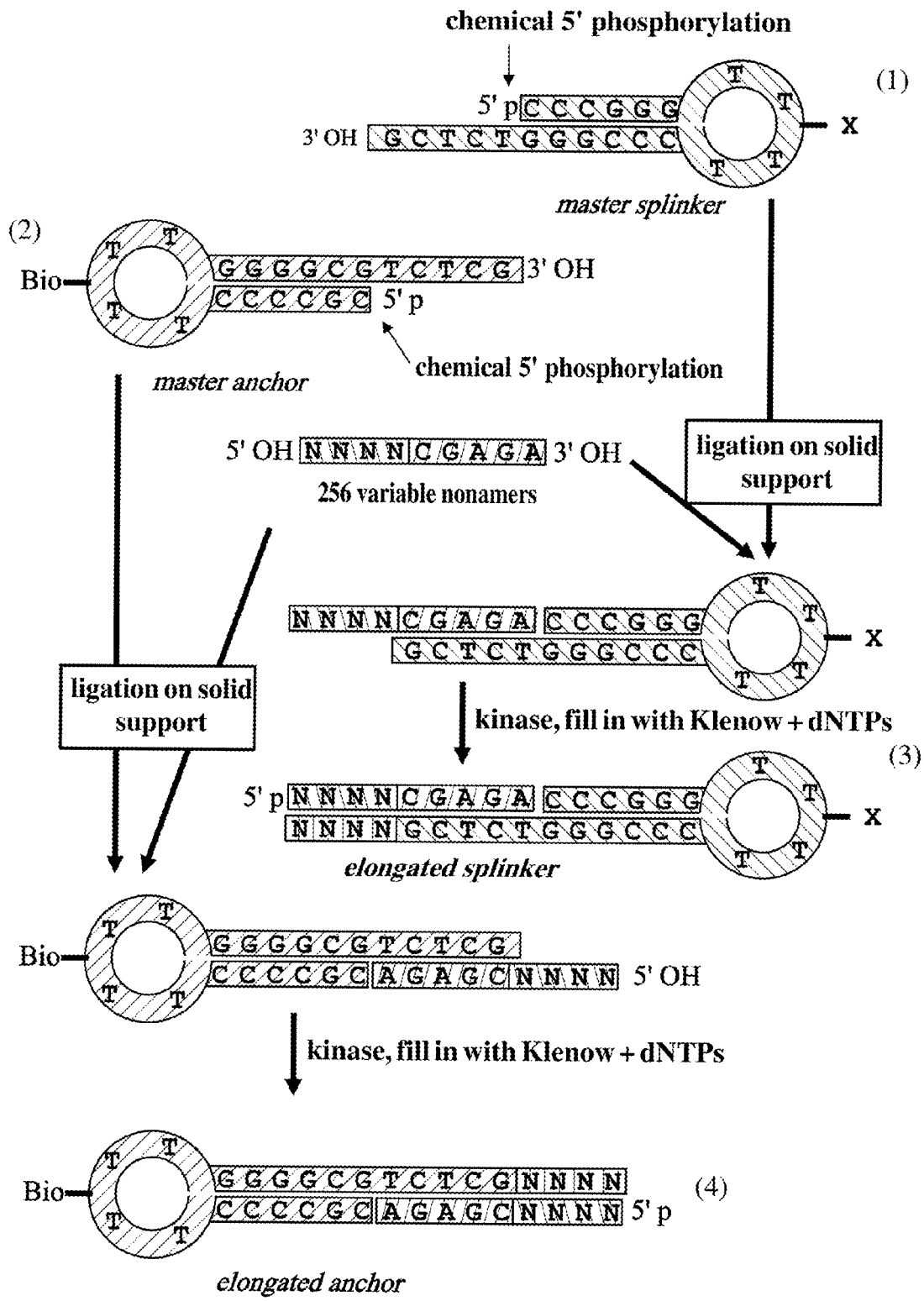

Shibata Y. et al., Cloning Full-Length, Cap-Trapper-Selected cDNAs by Using the Single-Strand Linker Ligation Method, *Brotechniques*; 30:1250-1254 (Jun. 2001).

Unrau Paul et al., Non-Cloning Amplification of Specific DNA Fragments from Whole Genomic DNA Digests Using DNA indexers, *Gene*; 145:163-169(1994).

Velculescu V. E. et al., Serial Analysis of Gene Expression, *Science*; 270: 484-487 (1995).

Van den Brulle, Jan, et al. 2008. A novel solid phase technology for high-throughput gene synthesis. BioTechniques. 45:340-43.

Berlin, (1999), Current Issues Molec. Biol., 'DNA Splicing by Directed Ligation (SDL)', 1(1), 21-30.

Crawford, M., et al., Briefings in Functional Genomics and Proteomics, vol. 2, No. 1, pp. 72-79, Apr. 2003.

Roberts, R.J., and D. Macelis (1999) REBASE—restriction enzymes and methylases. Nucleic Acids Res 27: 312-3.

Eugen Uhlmann: "An alternative approach in gene synthesis: use of long selfpriming oligodeoxynucleotides for the construction of double-stranded DNA", GENE, vol. 71, Nov. 15, 1988 (Nov. 15, 1988), pp. 29-40, XP000941756.

Wlodek Mandecki et al.: "A totally synthetic plasmid for general cloning, gene expression and mutagenesis in *Escherichia coli* ", GENE, vol. 94, Sep. 28, 1990 (Sep. 28, 1990), pp. 103-107, XP000941757.

Shao-Chi Huang et al., "Binding of biotinylated DNA to Streptavidin-Coated Polystryrene Latex." 222 Analytical Biochemistry (1994) 441-449.

Bolli, et al.; Pyranosyl-RNA:chiroselective self-assembly of base sequences by ligative oligomerization oftetranucleotide-2', 3'-cyclophosphates, 1997, Chem.Biol. 4(4): 309-320.

Hoare & Koshland; A methodfor the quantitative modification and estimation of carboxylic acid groups in proteins, 1967, 1. Biol. Chern. 242(10): 2447-2453.

Sekiya, et al.; Total Synthesis ofa tyrosine suppressor tRNA gene. xv. Synthesis of the promoter region, 1979, J. Bioi. Chern. 254(13): 5781-5786.

Sekiya, et al.; Total synthesis ofa tyrosine suppressor transfer RNA gene. XVI Enzymatic joinings to form the total 207-base pair-long DNA, 1979,1. Biol. Chern. 254(13): 5787-5801.

Xiong et al: "Non-polymerase-cycling-assembly-based chemical gene synthesis: Strategies, methods, and progress", Biotechnology Advances, Elsevier Publishing, Barking, GB, vol. 26, No. 2, Nov. 7, 2007 (Nov. 7, 2007), pp. 121-134, XP022426820.

\* cited by examiner

Simultaneous production of different gene variants (5)

*9. Restriction with the splinker-specific restriction endonuclease*

(I)

*10. Ligation of (biotinylated) splinker adapters*

(J)

FIG. 19

SEQUENCE LISTING

```
<160> NUMBER OF SEQ ID NOS: 167

<210> SEQ ID NO 1
<211> LENGTH: 11
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Recognition sequence of class I: Esp3I, BsmBI
<220> FEATURE:
<221> NAME/KEY: misc_feature
<222> LOCATION: (7)..(7)
<223> OTHER INFORMATION: Cleavage site in the upper strand, i. e. from
      5'->3' from left to right
<220> FEATURE:
<221> NAME/KEY: misc_feature
<222> LOCATION: (11)..(11)
<223> OTHER INFORMATION: Cleavage site in the lower strand, i.e. from
      5'->3' from right to left
<220> FEATURE:
<221> NAME/KEY: misc_feature
<222> LOCATION: (7)..(11)
<223> OTHER INFORMATION: N is any nucleotide of A, G, C or T

<400> SEQUENCE: 1
cgtctcnnnn n                                                              11

<210> SEQ ID NO 2
<211> LENGTH: 11
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Recognition sequence of 1: BsaI, Eco31I
<220> FEATURE:
<221> NAME/KEY: misc_feature
<222> LOCATION: (7)..(7)
<223> OTHER INFORMATION: Cleavage site in the upper strand, i. e. from
      5'->3' from left to right
<220> FEATURE:
<221> NAME/KEY: misc_feature
<222> LOCATION: (11)..(11)
<223> OTHER INFORMATION: Cleavage site in the lower strand, i. e. from
      5'->3' from right to left
<220> FEATURE:
<221> NAME/KEY: misc_feature
<222> LOCATION: (7)..(11)
<223> OTHER INFORMATION: N is any nucleotide of A, G, C or T

<400> SEQUENCE: 2
```

```
ggtctcnnnn n                                                          11
```

```
<210> SEQ ID NO 3
<211> LENGTH: 12
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Recognition sequence of class 1: BbsI, BpiI
<220> FEATURE:
<221> NAME/KEY: misc_feature
<222> LOCATION: (8)..(8)
<223> OTHER INFORMATION: Cleavage site in the upper strand, i. e. from
      5'->3' from left to right
<220> FEATURE:
<221> NAME/KEY: misc_feature
<222> LOCATION: (12)..(12)
<223> OTHER INFORMATION: Cleavage site in the lower strand, i. e. from
      5'->3' from right to left
<220> FEATURE:
<221> NAME/KEY: misc_feature
<222> LOCATION: (7)..(12)
<223> OTHER INFORMATION: N is any nucleotide of A, G, C or T T

<400> SEQUENCE: 3
gaagacnnnn nn                                                         12
```

```
<210> SEQ ID NO 4
<211> LENGTH: 14
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Recognition sequence of class 1: BspMI, Acc36I
<220> FEATURE:
<221> NAME/KEY: misc_feature
<222> LOCATION: (10)..(10)
<223> OTHER INFORMATION: Cleavage site in the upper strand, i. e. from
      5'->3' from left to right
<220> FEATURE:
<221> NAME/KEY: misc_feature
<222> LOCATION: (14)..(14)
<223> OTHER INFORMATION: Cleavage site in the lower strand, i. e. from
      5'->3' from right to left
<220> FEATURE:
<221> NAME/KEY: misc_feature
<222> LOCATION: (7)..(14)
<223> OTHER INFORMATION: N is any nucleotide of A, G, C or T

<400> SEQUENCE: 4
acctgcnnnn nnnn                                                       14
```

```
<210> SEQ ID NO 5
<211> LENGTH: 8
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Recognition sequence of class I: BtsI
<220> FEATURE:
<221> NAME/KEY: misc_feature
<222> LOCATION: (8)..(8)
<223> OTHER INFORMATION: Cleavage site in the upper strand, i. e. from
      5'->3' from left to right
<220> FEATURE:
<221> NAME/KEY: misc_feature
<222> LOCATION: (6)..(6)
```

```
<223> OTHER INFORMATION: Cleavage site in the lower strand, i. e. from
      5'->3' from right to left
<220> FEATURE:
<221> NAME/KEY: misc_feature
<222> LOCATION: (7)..(8)
<223> OTHER INFORMATION: N is any nucleotide of A, G, C or T

<400> SEQUENCE: 5 gcagtgnn                                                                  8

<210> SEQ ID NO 6
<211> LENGTH: 8
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Recognition sequence of class 1: BsrDI, Bse3DI
<220> FEATURE:
<221> NAME/KEY: misc_feature
<222> LOCATION: (8)..(8)
<223> OTHER INFORMATION: Cleavage site in the upper strand, i. e. from
      5'->3' from left to right
<220> FEATURE:
<221> NAME/KEY: misc_feature
<222> LOCATION: (6)..(6)
<223> OTHER INFORMATION: Cleavage site in the lower strand, i. e. from
      5'->3' from right to left
<220> FEATURE:
<221> NAME/KEY: misc_feature
<222> LOCATION: (7)..(8)
<223> OTHER INFORMATION: N is any nucleotide of A, G, C or T

<400> SEQUENCE: 6 gcaatgnn                                                                  8

<210> SEQ ID NO 7
<211> LENGTH: 12
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Recognition sequence of class 1: BciVI, BfuI
<220> FEATURE:
<221> NAME/KEY: misc_feature
<222> LOCATION: (12)..(12)
<223> OTHER INFORMATION: Cleavage site in the upper strand, i. e. from
      5'->3' from left to right
<220> FEATURE:
<221> NAME/KEY: misc_feature
<222> LOCATION: (11)..(11)
<223> OTHER INFORMATION: Cleavage site in the lower strand, i. e. from
      5'->3' from right to left
<220> FEATURE:
<221> NAME/KEY: misc_feature
<222> LOCATION: (7)..(12)
<223> OTHER INFORMATION: N is any nucleotide of A, G, C or T

<400> SEQUENCE: 7
gtatccnnnn nn                                                            12

<210> SEQ ID NO 8
<211> LENGTH: 11
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Recognition sequence of class 1: BfiI, BmrI
```

```
<220> FEATURE:
<221> NAME/KEY: misc_feature
<222> LOCATION: (11)..(11)
<223> OTHER INFORMATION: Cleavage site in the upper strand, i. e. from
      5'->3' from left to right
<220> FEATURE:
<221> NAME/KEY: misc_feature
<222> LOCATION: (10)..(10)
<223> OTHER INFORMATION: Cleavage site in the lower strand, i. e. from
      5'->3' from right to left
<220> FEATURE:
<221> NAME/KEY: misc_feature
<222> LOCATION: (7)..(11)
<223> OTHER INFORMATION: N is any nucleotide of A, G, C or T

<400> SEQUENCE: 8
actgggnnnn n                                                              11

<210> SEQ ID NO 9
<211> LENGTH: 17
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Recognition sequence of class 1: EciI
<220> FEATURE:
<221> NAME/KEY: misc_feature
<222> LOCATION: (17)..(17)
<223> OTHER INFORMATION: Cleavage site in the upper strand, i. e. from
      5'->3' from left to right
<220> FEATURE:
<221> NAME/KEY: misc_feature
<222> LOCATION: (15)..(15)
<223> OTHER INFORMATION: Cleavage site in the lower strand, i. e. from
      5'->3' from right to left
<220> FEATURE:
<221> NAME/KEY: misc_feature
<222> LOCATION: (7)..(17)
<223> OTHER INFORMATION: N is any nucleotide of A, G, C or T

<400> SEQUENCE: 9
ggcggannnn nnnnnnn                                                        17

<210> SEQ ID NO 10
<211> LENGTH: 16
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Recognition sequence of class 1: BseRI
<220> FEATURE:
<221> NAME/KEY: misc_feature
<222> LOCATION: (16)..(16)
<223> OTHER INFORMATION: Cleavage site in the upper strand, i. e. from
      5'->3' from left to right
<220> FEATURE:
<221> NAME/KEY: misc_feature
<222> LOCATION: (14)..(14)
<223> OTHER INFORMATION: Cleavage site in the lower strand, i. e. from
      5'->3' from right to left
<220> FEATURE:
<221> NAME/KEY: misc_feature
<222> LOCATION: (7)..(16)
<223> OTHER INFORMATION: N is any nucleotide of A, G, C or T

<400> SEQUENCE: 10
gaggagnnnn nnnnnn                                                         16

<210> SEQ ID NO 11
```

```
<211> LENGTH: 15
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Recognition sequence of class 1: AarI
<220> FEATURE:
<221> NAME/KEY: misc_feature
<222> LOCATION: (11)..(11)
<223> OTHER INFORMATION: Cleavage site in the upper strand, i. e. from
      5'->3' from left to right
<220> FEATURE:
<221> NAME/KEY: misc_feature
<222> LOCATION: (15)..(15)
<223> OTHER INFORMATION: Cleavage site in the lower strand, i. e. from
      5'->3' from right to left
<220> FEATURE:
<221> NAME/KEY: misc_feature
<222> LOCATION: (8)..(15)
<223> OTHER INFORMATION: N is any nucleotide of A, G, C or T

<400> SEQUENCE: 11
cacctgcnnn nnnnn                                                    15

<210> SEQ ID NO 12
<211> LENGTH: 17
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Recognition sequence of class 1: AceIII
<220> FEATURE:
<221> NAME/KEY: misc_feature
<222> LOCATION: (13)..(13)
<223> OTHER INFORMATION: Cleavage site in the upper strand, i. e. from
      5'->3' from left to right
<220> FEATURE:
<221> NAME/KEY: misc_feature
<222> LOCATION: (17)..(17)
<223> OTHER INFORMATION: Cleavage site in the lower strand, i. e. from
      5'->3' from right to left
<220> FEATURE:
<221> NAME/KEY: misc_feature
<222> LOCATION: (7)..(17)
<223> OTHER INFORMATION: N is any nucleotide of A, G, C or T

<400> SEQUENCE: 12
cagctcnnnn nnnnnnn                                                  17

<210> SEQ ID NO 13
<211> LENGTH: 11
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Recognition sequence of class 1: SapI
<220> FEATURE:
<221> NAME/KEY: misc_feature
<222> LOCATION: (8)..(8)
<223> OTHER INFORMATION: Cleavage site in the upper strand, i. e. from
      5'->3' from left to right
<220> FEATURE:
<221> NAME/KEY: misc_feature
<222> LOCATION: (11)..(11)
<223> OTHER INFORMATION: Cleavage site in the lower strand, i. e. from
      5'->3' from right to left
<220> FEATURE:
<221> NAME/KEY: misc_feature
<222> LOCATION: (8)..(11)
```

```
<223> OTHER INFORMATION: N is any nucleotide of A, G, C or T

<400> SEQUENCE: 13
gctcttcnnn n                                                           11

<210> SEQ ID NO 14
<211> LENGTH: 12
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 1 (5'-3'): Eco31I/Esp3I
<220> FEATURE:
<221> NAME/KEY: misc_feature
<222> LOCATION: (3)..(3)
<223> OTHER INFORMATION: N is any nucleotide of A, G, C or T; there may
      be 1-9 N present at this position
<220> FEATURE:
<221> NAME/KEY: misc_feature
<222> LOCATION: (4)..(4)
<223> OTHER INFORMATION: N = X is any nucleotide or non-nucleotide
      element (optionally with a corresponding modification) which is
      capable of chain formation, there may be 1-9 X present at this
      site
<220> FEATURE:
<221> NAME/KEY: misc_feature
<222> LOCATION: (5)..(5)
<223> OTHER INFORMATION: N = N', the nucleotide which is each
      complementary to N at the corresponding position in the counter
      strand; there may be 1-9 N' at this position
<220> FEATURE:
<221> NAME/KEY: misc_feature
<222> LOCATION: (12)..(12)
<223> OTHER INFORMATION: N is any nucleotide of A, G, C or T

<400> SEQUENCE: 14
cgnnncgtct cn                                                          12

<210> SEQ ID NO 15
<211> LENGTH: 14
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 1 (5'-3'): BbsI/Acc36I
<220> FEATURE:
<221> NAME/KEY: misc_feature
<222> LOCATION: (4)..(4)
<223> OTHER INFORMATION: N is any nucleotide of A, G, C or T; there may
      be 1-9 N at this position
<220> FEATURE:
<221> NAME/KEY: misc_feature
<222> LOCATION: (5)..(5)
<223> OTHER INFORMATION: N = X is any nucleotide or non-nucleotide
      element (optionally with a corresponding modification) which is
      capable of chain formation, there may be 1-9 X present at this
      site
<220> FEATURE:
<221> NAME/KEY: misc_feature
<222> LOCATION: (6)..(6)
<223> OTHER INFORMATION: N = N', the nucleotide which is each
      complementary to N at the corresponding position in the counter
      strand; there may be 1-9 N' at this position
<220> FEATURE:
<221> NAME/KEY: misc_feature
<222> LOCATION: (13)..(14)
<223> OTHER INFORMATION: N is any nucleotide of A, G, C or T

<400> SEQUENCE: 15
ttcnnngaag acnn                                                        14
```

<210> SEQ ID NO 16
<211> LENGTH: 12
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 2 (5'-3'): Eco31I/Esp3I
<220> FEATURE:
<221> NAME/KEY: misc_feature
<222> LOCATION: (3)..(3)
<223> OTHER INFORMATION: N is any nucleotide of A, G, C or T; there may
      be 1-9 N at this position
<220> FEATURE:
<221> NAME/KEY: misc_feature
<222> LOCATION: (4)..(4)
<223> OTHER INFORMATION: N = X is any nucleotide or non-nucleotide
      element (optionally with a corresponding modification) which
      is capable of chain formation, there may be 1-9 X present at this
      site
<220> FEATURE:
<221> NAME/KEY: misc_feature
<222> LOCATION: (5)..(5)
<223> OTHER INFORMATION: N = N', the nucleotide which is each
      complementary to N at the corresponding position in the counter
      strand; there may be 1-9 N' at this position
<220> FEATURE:
<221> NAME/KEY: misc_feature
<222> LOCATION: (12)..(12)
<223> OTHER INFORMATION: N is any nucleotide of A, G, C or T

<400> SEQUENCE: 16 ccnnggtct cn                                                        12

<210> SEQ ID NO 17
<211> LENGTH: 15
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 2 (5'-3'): BbsI/Acc36I
<220> FEATURE:
<221> NAME/KEY: misc_feature
<222> LOCATION: (6)..(6)
<223> OTHER INFORMATION: N is any nucleotide of A, G, C or T; there may
      be 1-9 N at this position
<220> FEATURE:
<221> NAME/KEY: misc_feature
<222> LOCATION: (7)..(7)
<223> OTHER INFORMATION: N = X is any nucleotide or non-nucleotide
      element (optionally with a corresponding modification) which is
      capable of chain formation, there may be 1-9 X present at this
      site
<220> FEATURE:
<221> NAME/KEY: misc_feature
<222> LOCATION: (8)..(8)
<223> OTHER INFORMATION: N = N', the nucleotide which is each
      complementary to N at the corresponding position in the counter
      strand; there may be 1-9 N' at this position
<220> FEATURE:
<221> NAME/KEY: misc_feature
<222> LOCATION: (15)..(15)
<223> OTHER INFORMATION: N is any nucleotide of A, G, C or T; there are
      4 N present at this position

<400> SEQUENCE: 17
caggtnnnac ctgcn                                                    15

<210> SEQ ID NO 18
<211> LENGTH: 9

```
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Linker (5'-3'): Eco31I/Esp3I
<220> FEATURE:
<221> NAME/KEY: misc_feature
<222> LOCATION: (5)..(5)
<223> OTHER INFORMATION: N = N', the nucleotide which is each
      complementary to N at the corresponding position in the counter
      strand
<220> FEATURE:
<221> NAME/KEY: misc_feature
<222> LOCATION: (1)..(4)
<223> OTHER INFORMATION: N is any nucleotide of A, G, C or T

<400> SEQUENCE: 18 nnnnngaga                                                              9

<210> SEQ ID NO 19
<211> LENGTH: 8
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Linker a (5'-3'): BbsI/Acc36I
<220> FEATURE:
<221> NAME/KEY: misc_feature
<222> LOCATION: (5)..(5)
<223> OTHER INFORMATION: N = N', the nucleotide which is each
      complementary to N at the corresponding position in the counter
      strand
<220> FEATURE:
<221> NAME/KEY: misc_feature
<222> LOCATION: (5)..(5)
<223> OTHER INFORMATION: 2 N' present
<220> FEATURE:
<221> NAME/KEY: misc_feature
<222> LOCATION: (1)..(4)
<223> OTHER INFORMATION: N is any nucleotide A, G, C or T

<400> SEQUENCE: 19 nnnnngtc                                                               8

<210> SEQ ID NO 20
<211> LENGTH: 6
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Linker b (5'-3'): BbsI/Acc36I
<220> FEATURE:
<221> NAME/KEY: misc_feature
<222> LOCATION: (5)..(5)
<223> OTHER INFORMATION: N = N', the nucleotide which is each
      complementary to N at the corresponding position in the counter
      strand
<220> FEATURE:
<221> NAME/KEY: misc_feature
<222> LOCATION: (5)..(5)
<223> OTHER INFORMATION: 4 N' present
<220> FEATURE:
<221> NAME/KEY: misc_feature
<222> LOCATION: (1)..(4)
<223> OTHER INFORMATION: N is any nucleotide of A, G, C or T

<400> SEQUENCE: 20 nnnnng                                                                 6
```

```
<210> SEQ ID NO 21
<211> LENGTH: 8
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 1: Eco31I/Esp3I (bipartite)
<220> FEATURE:
<221> NAME/KEY: misc_feature
<222> LOCATION: (1)..(1)
<223> OTHER INFORMATION: N is any nucleotide of A, G, C or T; an there
      may be 1-9 N present at this position
<220> FEATURE:
<221> NAME/KEY: misc_feature
<222> LOCATION: (8)..(8)
<223> OTHER INFORMATION: N is any nucleotide of A, G, C or T

<400> SEQUENCE: 21 ncgtctcn                                                                    8

<210> SEQ ID NO 22
<211> LENGTH: 3
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 1: Eco31I/Esp3I (bipartite)
<220> FEATURE:
<221> NAME/KEY: misc_feature
<222> LOCATION: (3)..(3)
<223> OTHER INFORMATION: N = N', the nucleotide which is each
      complementary to N at the corresponding position in the counter
      strand; there may be 1-9 N' present at this position

<400> SEQUENCE: 22 cgn                                                                         3

<210> SEQ ID NO 23
<211> LENGTH: 3
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 2 (5'-3'): Eco31I/Esp3I
      (bipartite)
<220> FEATURE:
<221> NAME/KEY: misc_feature
<222> LOCATION: (3)..(3)
<223> OTHER INFORMATION: N = N', the nucleotide which is each
      complementary to N at the corresponding position in the counter
      strand; there may be 1-9 N' present at this position

<400> SEQUENCE: 23 ccn                                                                         3

<210> SEQ ID NO 24
<211> LENGTH: 8
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 2 (5'-3'): Eco31I/Esp3I
      (bipartite)
```

```
<220> FEATURE:
<221> NAME/KEY: misc_feature
<222> LOCATION: (1)..(1)
<223> OTHER INFORMATION: N is any nucleotide of A, G, C or T; there may
      be 1-9 N present at this position
<220> FEATURE:
<221> NAME/KEY: misc_feature
<222> LOCATION: (8)..(8)
<223> OTHER INFORMATION: N is any nucleotide of A, G, C or T

<400> SEQUENCE: 24 nggtctcn                                                                   8

<210> SEQ ID NO 25
<211> LENGTH: 6
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Linker (5'-3'): Eco31I/Esp3I (bipartite)
<220> FEATURE:
<221> NAME/KEY: misc_feature
<222> LOCATION: (1)..(1)
<223> OTHER INFORMATION: N is any nucleotide of A, G, C or T; there may
      be 1-9 N present at this position

<400> SEQUENCE: 25 ncgaga                                                                     6

<210> SEQ ID NO 26
<211> LENGTH: 9
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 1 (5'-3'): BbsI/Acc36I
      (bipartite)
<220> FEATURE:
<221> NAME/KEY: misc_feature
<222> LOCATION: (1)..(1)
<223> OTHER INFORMATION: N is any nucleotide of A, G, C or T; there may
      be 1-9 N present at this position
<220> FEATURE:
<221> NAME/KEY: misc_feature
<222> LOCATION: (8)..(9)
<223> OTHER INFORMATION: N is any nucleotide of A, G, C or T

<400> SEQUENCE: 26 ngaagacnn                                                                  9

<210> SEQ ID NO 27
<211> LENGTH: 4
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 1 (5'-3'): BbsI/Acc36I
      (bipartite)
<220> FEATURE:
<221> NAME/KEY: misc_feature
<222> LOCATION: (4)..(4)
<223> OTHER INFORMATION: N is any nucleotide of A, G, C or T; there may
      be 1-9 N present at this position

<400> SEQUENCE: 27 ttcn                                                                       4
```

```
<210> SEQ ID NO 28
<211> LENGTH: 6
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 2 (5'-3'): BbsI/Acc36I
      (bipartite)
<220> FEATURE:
<221> NAME/KEY: misc_feature
<222> LOCATION: (6)..(6)
<223> OTHER INFORMATION: N is any nucleotide of A, G, C or T; there may
      be 1-9 N present at this position

<400> SEQUENCE: 28 caggtn                                                                    6

<210> SEQ ID NO 29
<211> LENGTH: 11
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 2 (5'-3'): BbsI/Acc36I
      (bipartite)
<220> FEATURE:
<221> NAME/KEY: misc_feature
<222> LOCATION: (1)..(1)
<223> OTHER INFORMATION: N = N', the nucleotide which is each
      complementary to N at the corresponding position in the counter
      strand; there may be 1-9 N' present at this position
<220> FEATURE:
<221> NAME/KEY: misc_feature
<222> LOCATION: (8)..(11)
<223> OTHER INFORMATION: N is any nucleotide of A, G, C or T

<400> SEQUENCE: 29
nacctgcnnn n                                                             11

<210> SEQ ID NO 30
<211> LENGTH: 9
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Linker (5'-3'): BbsI/Acc36I (bipartite)
<220> FEATURE:
<221> NAME/KEY: misc_feature
<222> LOCATION: (1)..(6)
<223> OTHER INFORMATION: N is any nucleotide of A, G, C or T

<400> SEQUENCE: 30 nnnnnngtc                                                                 9

<210> SEQ ID NO 31
<211> LENGTH: 6
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Linker (5'-3'): BbsI/Acc36I (bipartite)
<220> FEATURE:
<221> NAME/KEY: misc_feature
```

```
<222> LOCATION: (5)..(5)
<223> OTHER INFORMATION: N = N', the nucleotide which is each
      complementary to N at the corresponding position in the counter
      strand
<220> FEATURE:
<221> NAME/KEY: misc_feature
<222> LOCATION: (5)..(5)
<223> OTHER INFORMATION: 4 N' present
<220> FEATURE:
<221> NAME/KEY: misc_feature
<222> LOCATION: (1)..(4)
<223> OTHER INFORMATION: N is any nucleotide of A, G, C or T

<400> SEQUENCE: 31 nnnnng                                                                  6

<210> SEQ ID NO 32
<211> LENGTH: 21
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 1 (5'-3'): Eco31I/Esp3I; Table
      2

<400> SEQUENCE: 32 cgccccttttt ggggcgtctc g                                               21

<210> SEQ ID NO 33
<211> LENGTH: 21
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 1 (5'-3'): BbsI/Acc36I; Table 2

<400> SEQUENCE: 33
ttcgggtttt cccgaagacg c                                                21

<210> SEQ ID NO 34
<211> LENGTH: 21
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 2 (5'-3'): Eco31I/Esp3I; Table
      2

<400> SEQUENCE: 34
cccgggtttt cccgggtctc g                                                21

<210> SEQ ID NO 35
<211> LENGTH: 25
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 2 (5'-3'): BbsI/Acc36I; Table 2

<400> SEQUENCE: 35
caggtgggtt ttcccactgg gacgc                                            25
```

```
<210> SEQ ID NO 36
<211> LENGTH: 9
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Linker (5'-3'): Eco31I/Esp3I; Table 2
<220> FEATURE:
<221> NAME/KEY: misc_feature
<222> LOCATION: (1)..(4)
<223> OTHER INFORMATION: N is any nucleotide of A, G, C or T

<400> SEQUENCE: 36 nnnncgaga                                                                 9

<210> SEQ ID NO 37
<211> LENGTH: 9
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Linker (5'-3'): BbsI/Acc36I; Table 2
<220> FEATURE:
<221> NAME/KEY: misc_feature
<222> LOCATION: (1)..(4)
<223> OTHER INFORMATION: N is any nucleotide of A, G, C or T

<400> SEQUENCE: 37 nnnngcgtc                                                                 9

<210> SEQ ID NO 38
<211> LENGTH: 9
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Linker (5'-3'): Eco31I/Esp3I (bipartite); Table
      2
<220> FEATURE:
<221> NAME/KEY: misc_feature
<222> LOCATION: (1)..(4)
<223> OTHER INFORMATION: N is any nucleotide of A, G, C or T

<400> SEQUENCE: 38 nnnncgaga                                                                 9

<210> SEQ ID NO 39
<211> LENGTH: 9
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Linker (5'-3'): BbsI/Acc36I (bipartite); Table 2
<220> FEATURE:
<221> NAME/KEY: misc_feature
<222> LOCATION: (1)..(4)
<223> OTHER INFORMATION: N is any nucleotide of A, G, C or T

<400> SEQUENCE: 39 nnnngcgtc                                                                 9

<210> SEQ ID NO 40
```

```
<211> LENGTH: 17
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 1 (5'-3'): Eco31I/Esp3I
      (bipartite); Table 2

<400> SEQUENCE: 40
ggggcgtctc gcgcccc                                                     17

<210> SEQ ID NO 41
<211> LENGTH: 17
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 1 (5'-3'): BbsI/Acc36I
      (bipartite); Table 2

<400> SEQUENCE: 41
cccgaagacg cttcggg                                                     17

<210> SEQ ID NO 42
<211> LENGTH: 17
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 2 (5'-3'): Eco31I/Esp3I
      (bipartite); Table 2

<400> SEQUENCE: 42
cccgggcccg ggtctcg                                                     17

<210> SEQ ID NO 43
<211> LENGTH: 19
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Oligonucleotide 2 (5'-3'): BbsI/Acc36I
      (bipartite); Table 2

<400> SEQUENCE: 43
caggtgccca ctgggacgc                                                   19

<210> SEQ ID NO 44
<211> LENGTH: 21
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 1, Step 1 (first nucleic acid from top);
      Modification for the binding on a solid carrier
<220> FEATURE:
<221> NAME/KEY: misc_feature
<222> LOCATION: (1)..(1)
<223> OTHER INFORMATION: chemical 5'-phosphorylated

<400> SEQUENCE: 44
```
cccgggtttt cccgggtctc g                                              21

<210> SEQ ID NO 45
<211> LENGTH: 21
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 1, Step 2 (second nucleic acid from top),
      biotinylated
<220> FEATURE:
<221> NAME/KEY: misc_feature
<222> LOCATION: (1)..(1)
<223> OTHER INFORMATION: chemical 5'-phosphorylated

<400> SEQUENCE: 45 cgccccttt ggggcgtctc g                                               21

<210> SEQ ID NO 46
<211> LENGTH: 9
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 1 (third nucleic acid from top)
<220> FEATURE:
<221> NAME/KEY: misc_feature
<222> LOCATION: (1)..(4)
<223> OTHER INFORMATION: any nucleotide

<400> SEQUENCE: 46 nnnncgaga                                                             9

<210> SEQ ID NO 47
<211> LENGTH: 30
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 1, (fourth nucleic acid from top),
      Modification for the binding on a solid carrier
<220> FEATURE:
<221> NAME/KEY: misc_feature
<222> LOCATION: (1)..(4)
<223> OTHER INFORMATION: any nucleotide

<400> SEQUENCE: 47
nnnncgagac ccgggttttc ccgggtctcg                                     30

<210> SEQ ID NO 48
<211> LENGTH: 34
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 1, Step 3 (fifth nucleic acid from top),
      Modification for the binding on a solid carrier
<220> FEATURE:
<221> NAME/KEY: misc_feature
<222> LOCATION: (1)..(4)
<223> OTHER INFORMATION: any nucleotide
<220> FEATURE:
<221> NAME/KEY: misc_feature

```
<222> LOCATION: (31)..(34)
<223> OTHER INFORMATION: any nucleotide

<400> SEQUENCE: 48
nnnncgagac ccgggttttc ccgggtctcg nnnn                              34

<210> SEQ ID NO 49
<211> LENGTH: 30
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 1, (sixth nucleic acid from top),
      biotinylated
<220> FEATURE:
<221> NAME/KEY: misc_feature
<222> LOCATION: (1)..(4)
<223> OTHER INFORMATION: any nucleotide

<400> SEQUENCE: 49
nnnncgagac gcccttttg gggcgtctcg                                    30

<210> SEQ ID NO 50
<211> LENGTH: 34
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 1, Step 4 (seventh nucleic acid from top),
      biotinylated
<220> FEATURE:
<221> NAME/KEY: misc_feature
<222> LOCATION: (1)..(4)
<223> OTHER INFORMATION: any nucleotide
<220> FEATURE:
<221> NAME/KEY: misc_feature
<222> LOCATION: (31)..(34)
<223> OTHER INFORMATION: any nucleotide

<400> SEQUENCE: 50
nnnncgagac gcccttttg gggcgtctcg nnnn                               34

<210> SEQ ID NO 51
<211> LENGTH: 20
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 2, (left nucleic acid of the first line
      from top), biotinylated

<400> SEQUENCE: 51
gcgcgttttc gcgctcttcc                                              20

<210> SEQ ID NO 52
<211> LENGTH: 9
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 2 (middle nucleic acid of the first line
      from top)
<220> FEATURE:
```

```
<221> NAME/KEY: misc_feature
<222> LOCATION: (1)..(3)
<223> OTHER INFORMATION: any nucleotide

<400> SEQUENCE: 52 nnnggaaga                                                                    9

<210> SEQ ID NO 53
<211> LENGTH: 20
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 2 (right nucleic acid of the first line
      from top), Modification for the binding on a solid carrier and
      biotinylated

<400> SEQUENCE: 53
gggggttttc ccctcttcc                                                        20

<210> SEQ ID NO 54
<211> LENGTH: 29
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 2, Step A (left nucleic acid of the second
      line from top), biotinylated
<220> FEATURE:
<221> NAME/KEY: misc_feature
<222> LOCATION: (1)..(3)
<223> OTHER INFORMATION: any nucleotide

<400> SEQUENCE: 54
nnnggaagag cgcgttttcg cgctcttcc                                             29

<210> SEQ ID NO 55
<211> LENGTH: 29
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 2, A (right nucleic acid of the second
      line from top), Modification for the binding on a solid carrier
      and biotinylated
<220> FEATURE:
<221> NAME/KEY: misc_feature
<222> LOCATION: (1)..(3)
<223> OTHER INFORMATION: any nucleotide

<400> SEQUENCE: 55
nnnggaagag ggggttttcc ccctcttcc                                             29

<210> SEQ ID NO 56
<211> LENGTH: 32
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 2, B (left nucleic acid of the third line
      from top), biotinylated
<220> FEATURE:
<221> NAME/KEY: misc_feature
```

```
<222> LOCATION: (1)..(3)
<223> OTHER INFORMATION: any nucleotide
<220> FEATURE:
<221> NAME/KEY: misc_feature
<222> LOCATION: (30)..(32)
<223> OTHER INFORMATION: any nucleotide

<400> SEQUENCE: 56
nnnggaagag cgcgttttcg cgctcttccn nn                                32

<210> SEQ ID NO 57
<211> LENGTH: 32
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 2, B (right nucleic acid of the third line
      from top), Modification for the binding on a solid carrier and
      biotinylated
<220> FEATURE:
<221> NAME/KEY: misc_feature
<222> LOCATION: (1)..(3)
<223> OTHER INFORMATION: Fig. 2, right nucleic acid of the third line
      from top
<220> FEATURE:
<221> NAME/KEY: misc_feature
<222> LOCATION: (30)..(32)
<223> OTHER INFORMATION: Fig. 2, right nucleic acid of the third line
      from top

<400> SEQUENCE: 57
nnnggaagag ggggttttcc ccctcttccn nn                                32

<210> SEQ ID NO 58
<211> LENGTH: 64
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 3, C (nucleic acid of the first line from
      top), Modification for the binding on a solid carrier and double
      biotinylated
<220> FEATURE:
<221> NAME/KEY: misc_feature
<222> LOCATION: (12)..(17)
<223> OTHER INFORMATION: any nucleotide
<220> FEATURE:
<221> NAME/KEY: misc_feature
<222> LOCATION: (44)..(49)
<223> OTHER INFORMATION: any nucleotide

<400> SEQUENCE: 58
cgcgctcttc cnnnnnngga agaggggtt ttccccctct tccnnnnnng gaagagcgcg    60
tttt                                                               64

<210> SEQ ID NO 59
<211> LENGTH: 35
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 3, D (nucleic acid of the second line from
      top), Modification for the binding on a solid carrier and
      biotinylated
<220> FEATURE:
<221> NAME/KEY: misc_feature
```

```
<222> LOCATION: (1)..(6)
<223> OTHER INFORMATION: any nucleotide
<220> FEATURE:
<221> NAME/KEY: misc_feature
<222> LOCATION: (33)..(35)
<223> OTHER INFORMATION: any nucleotide

<400> SEQUENCE: 59
nnnnnnggaa gagggggttt tccccctctt ccnnn                              35

<210> SEQ ID NO 60
<211> LENGTH: 20
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 4, A (left nucleic acid of the first line
      from top), biotinyated

<400> SEQUENCE: 60
gcgcgttttc gcgctcttcc                                               20

<210> SEQ ID NO 61
<211> LENGTH: 8
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 4, A (upper middle nucleic acid of the
      first line from top)
<220> FEATURE:
<221> NAME/KEY: misc_feature
<222> LOCATION: (1)..(2)
<223> OTHER INFORMATION: any nucleotide

<400> SEQUENCE: 61 nnggaaga                                                             8

<210> SEQ ID NO 62
<211> LENGTH: 8
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 4, A (below middle nucleic acid of the
      first line from top)
<220> FEATURE:
<221> NAME/KEY: misc_feature
<222> LOCATION: (1)..(2)
<223> OTHER INFORMATION: any nucleotide

<400> SEQUENCE: 62 nnagagac                                                             8

<210> SEQ ID NO 63
<211> LENGTH: 18
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 4, A (right nucleic acid of the first line
      from top), Modification for the binding on a solid carrier and
      biotinylated
```

```
<400> SEQUENCE: 63
ccccttttgg gggtctct                                                    18

<210> SEQ ID NO 64
<211> LENGTH: 28
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 4, B (left nucleic acid of the second line
      from top), biotinylated
<220> FEATURE:
<221> NAME/KEY: misc_feature
<222> LOCATION: (1)..(2)
<223> OTHER INFORMATION: any nucleotide

<400> SEQUENCE: 64
nnggaagagc gcgttttcgc gctcttcc                                         28

<210> SEQ ID NO 65
<211> LENGTH: 26
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 4, B (right nucleic acid of the second
      line from top), modification for the binding on a solid carrier
      and biotinylated
<220> FEATURE:
<221> NAME/KEY: misc_feature
<222> LOCATION: (1)..(2)
<223> OTHER INFORMATION: Fig. 4, right nucleic acid of the second line
      from top

<400> SEQUENCE: 65
nnagagaccc cctttggggg gtctct                                           26

<210> SEQ ID NO 66
<211> LENGTH: 30
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 4, C (left nucleic acid of the third line
      from top), biotinylated
<220> FEATURE:
<221> NAME/KEY: misc_feature
<222> LOCATION: (1)..(2)
<223> OTHER INFORMATION: Fig. 4, left nucleic acid of the third line
      from top
<220> FEATURE:
<221> NAME/KEY: misc_feature
<222> LOCATION: (29)..(30)
<223> OTHER INFORMATION: Fig. 4, left nucleic acid of the third line
      from top

<400> SEQUENCE: 66
nnggaagagc gcgttttcgc gctcttccnn                                       30

<210> SEQ ID NO 67
<211> LENGTH: 28
<212> TYPE: DNA
<213> ORGANISM: Artificial Sequence
<220> FEATURE:
```

```
<223> OTHER INFORMATION: Chemically synthesized
<220> FEATURE:
<221> NAME/KEY: misc_feature
<223> OTHER INFORMATION: Fig. 4, C (right nucleic acid of the third
      line from top), Modification for the binding on a solid carrier
      and biotinylated
<220> FEATURE:
<221> NAME/KEY: misc_feature
<222> LOCATION: (1)..(2)
<223> OTHER INFORMATION: Fig. 4, right nucleic acid of the third line
      from top
<220> FEATURE:
<221> NAME/KEY: misc_feature
<222> LOCATION: (27)..(28)
<223> OTHER INFORMATION: Fig. 4, right nucleic acid of the third line
      from top

<400> SEQUENCE: 67
nnagagaccc cctttttgggg gtctctnn                                           28

<210> SEQ ID NO 68
<211> LENGTH: 58
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 5, Step D (nucleic acid of the first line
      from top), Modification for the binding on a solid carrier and
      biotinylated
<220> FEATURE:
<221> NAME/KEY: misc_feature
<222> LOCATION: (12)..(15)
<223> OTHER INFORMATION: any nucleotide
<220> FEATURE:
<221> NAME/KEY: misc_feature
<222> LOCATION: (40)..(43)
<223> OTHER INFORMATION: any nucleotide

<400> SEQUENCE: 68
cgcgctcttc cnnnnagaga ccccctttttg ggggtctctn nnnggaagag cgcgtttt          58

<210> SEQ ID NO 69
<211> LENGTH: 29
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 5, E (nucleic acid of the second line
      from top), Modification for the binding on a solid carrier
<220> FEATURE:
<221> NAME/KEY: misc_feature
<222> LOCATION: (1)..(4)
<223> OTHER INFORMATION: any nucleotide
<220> FEATURE:
<221> NAME/KEY: misc_feature
<222> LOCATION: (29)..(29)
<223> OTHER INFORMATION: any nucleotide

<400> SEQUENCE: 69
nnnnagagac ccccttttgg gggtctctn                                           29

<210> SEQ ID NO 70
<211> LENGTH: 18
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
```

-continued

<223> OTHER INFORMATION: Fig. 6, A (nucleic acid of the first line from
      top)

<400> SEQUENCE: 70
aggtctagcc caagtcgt                                                    18

<210> SEQ ID NO 71
<211> LENGTH: 18
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 6, A (complementary sequence to the
      nucleic acid of the first line from top)

<400> SEQUENCE: 71
acgacttggg ctagacct                                                    18

<210> SEQ ID NO 72
<211> LENGTH: 62
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 6, B (nucleic acid of the second line from
      top), biotinylated

<400> SEQUENCE: 72
gcgcgtctca aggtctagaa gagcgcgttt tcgcgctctt ctagaccttg agacgcgctt      60
tt                                                                     62

<210> SEQ ID NO 73
<211> LENGTH: 68
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 6, C (nucleic acid of the third line from
      top), biotinylated

<400> SEQUENCE: 73
gcgcgtctca aggtctagca gaagagcgcg ttttcgcgct cttctgctag accttgagac      60
gcgctttt                                                               68

<210> SEQ ID NO 74
<211> LENGTH: 74
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 6, D (nucleic acid of the fourth line from
      top), biotinylated

<400> SEQUENCE: 74
gcgcgtctca aggtctagcc caaagagcgc gcgttttcgc gctcttcttg ggctagacct      60
tgagacgcgc tttt                                                        74

<210> SEQ ID NO 75

-continued

```
<211> LENGTH: 74
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 6, E (nucleic acid of the fifth line from
      top). biotinylated

<400> SEQUENCE: 75
gcgcgtctca aggtctagcc caaagagacc cgcttttgcg ggtctctttg ggctagacct    60
tgagacgcgc tttt                                                     74

<210> SEQ ID NO 76
<211> LENGTH: 46
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 6 (nucleic acid of the sixth line from
      top), biotinylated

<400> SEQUENCE: 76
cgatctggaa ctctgcgcgt tttcgcgcag agttccagat cgggtt                  46

<210> SEQ ID NO 77
<211> LENGTH: 21
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 7, A (nucleic acid of the first line from
      top)

<400> SEQUENCE: 77
aggtctagcc caagtcgtaa g                                             21

<210> SEQ ID NO 78
<211> LENGTH: 21
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 7, A (complementary sequence to the
      nucleic acid of the first lien from top)

<400> SEQUENCE: 78
cttacgactt gggctagacc t                                             21

<210> SEQ ID NO 79
<211> LENGTH: 62
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 7, B (nucleic acid of the second line
      from top), biotinylated

<400> SEQUENCE: 79
gcgcgtctca ccaagtagaa gagcgcgttt tcgcgctctt ctacttggtg agacgcgctt   60
``` tt                                                                  62

<210> SEQ ID NO 80
<211> LENGTH: 68
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 7, C (nucleic acid of the third line from
      top), biotinylated

<400> SEQUENCE: 80
gcgcgtctca ccaagtcgta gaagagcgcg ttttcgcgct cttctacgac ttggtgagac    60
gcgctttt                                                            68

<210> SEQ ID NO 81
<211> LENGTH: 74
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 7, D (nucleic acid of the fourth line from
      top), biotinylated

<400> SEQUENCE: 81
gcgcgtctca ccaagtcgta agagcgcgcg gcgttttcgc gctcttctct tacgacttgg    60
tgagacgcgc tttt                                                     74

<210> SEQ ID NO 82
<211> LENGTH: 74
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 7, E (nucleic acid of the fifth line from
      top), biotinylated

<400> SEQUENCE: 82
gcgcgtctca ccaagtcgta agaagagacc cgcttttgcg ggtctcttct tacgacttgg    60
tgagacgcgc tttt                                                     74

<210> SEQ ID NO 83
<211> LENGTH: 46
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 7, F (nucleic acid of the sixth line from
      top)

<400> SEQUENCE: 83
cagcattctt ctctgggcgt tttcgcccag agaagaatgc tgaacc                  46

<210> SEQ ID NO 84
<211> LENGTH: 21
<212> TYPE: DNA
<213> ORGANISM: Artificial Sequence
<220> FEATURE:

<223> OTHER INFORMATION: Chemically synthesized
<220> FEATURE:
<221> NAME/KEY: misc_feature
<223> OTHER INFORMATION: Fig. 8, A (sequence of the nucleic acid of the
      first line)

<400> SEQUENCE: 84
aggtctagcc caagtcgtaa g                                              21

<210> SEQ ID NO 85
<211> LENGTH: 21
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 8, A (complementary sequence of the
      nucleic acid of the first line)

<400> SEQUENCE: 85
cttacgactt gggctagacc t                                              21

<210> SEQ ID NO 86
<211> LENGTH: 92
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 8, B (nucleic acid of the second line from
      top), biotinylated

<400> SEQUENCE: 86
gcgcgtctca aggtctagcc caagtcgtaa gaagagaccc gcttttgcgg gtctcttctt    60 acgactggg ctagaccttg agacgcgctt tt                                   92

Figure 9:
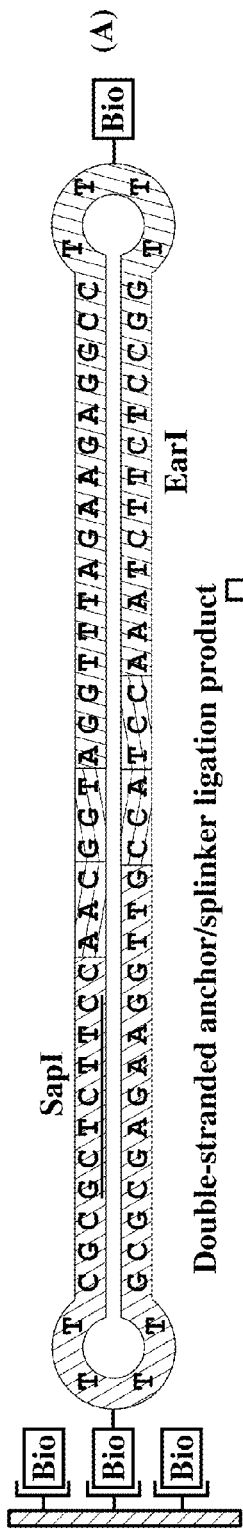
Figure 9:
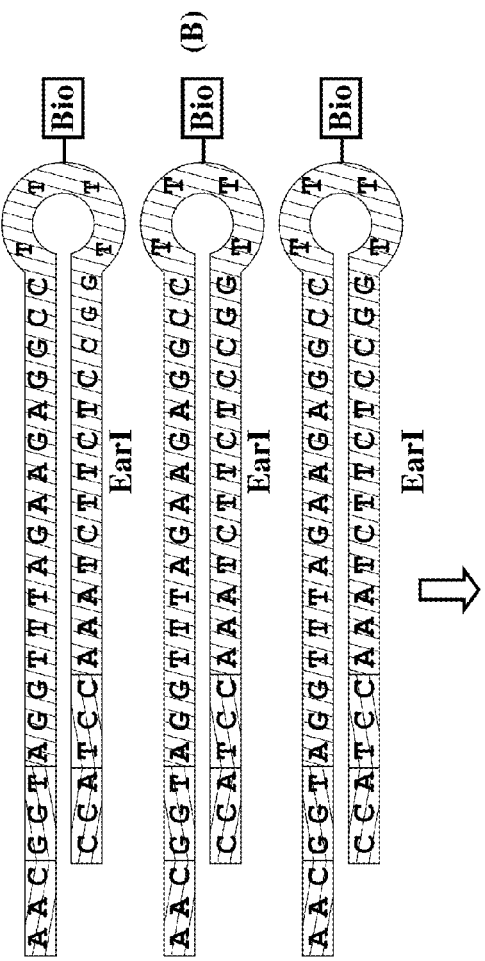

<210> SEQ ID NO 87
<211> LENGTH: 74
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 9, A (nucleic acid of the first line from
      top), double biotinylated

<400> SEQUENCE: 87
cgcgctcttc caacggtagg tttagaagag gccttttggc ctcttctaaa cctaccgttg    60
gaagagcgcg tttt                                                      74

<210> SEQ ID NO 88
<211> LENGTH: 45
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 9, B (nucleic acid of the second line from
      top), biotinylated

<400> SEQUENCE: 88
aacggtaggt ttagaagagg ccttttggcc tcttctaaac ctacc                    45

<210> SEQ ID NO 89
<211> LENGTH: 45
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 9, B (nucleic acid of the third line from top), biotinlyated

<400> SEQUENCE: 89
aacggtaggt ttagaagagg cctttggcc tcttctaaac ctacc                45

<210> SEQ ID NO 90
<211> LENGTH: 45
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 9, B (nucleic acid of the fourth line from top), biotinylated

<400> SEQUENCE: 90
aacggtaggt ttagaagagg cctttggcc tcttctaaac ctacc                45

Figure 10:
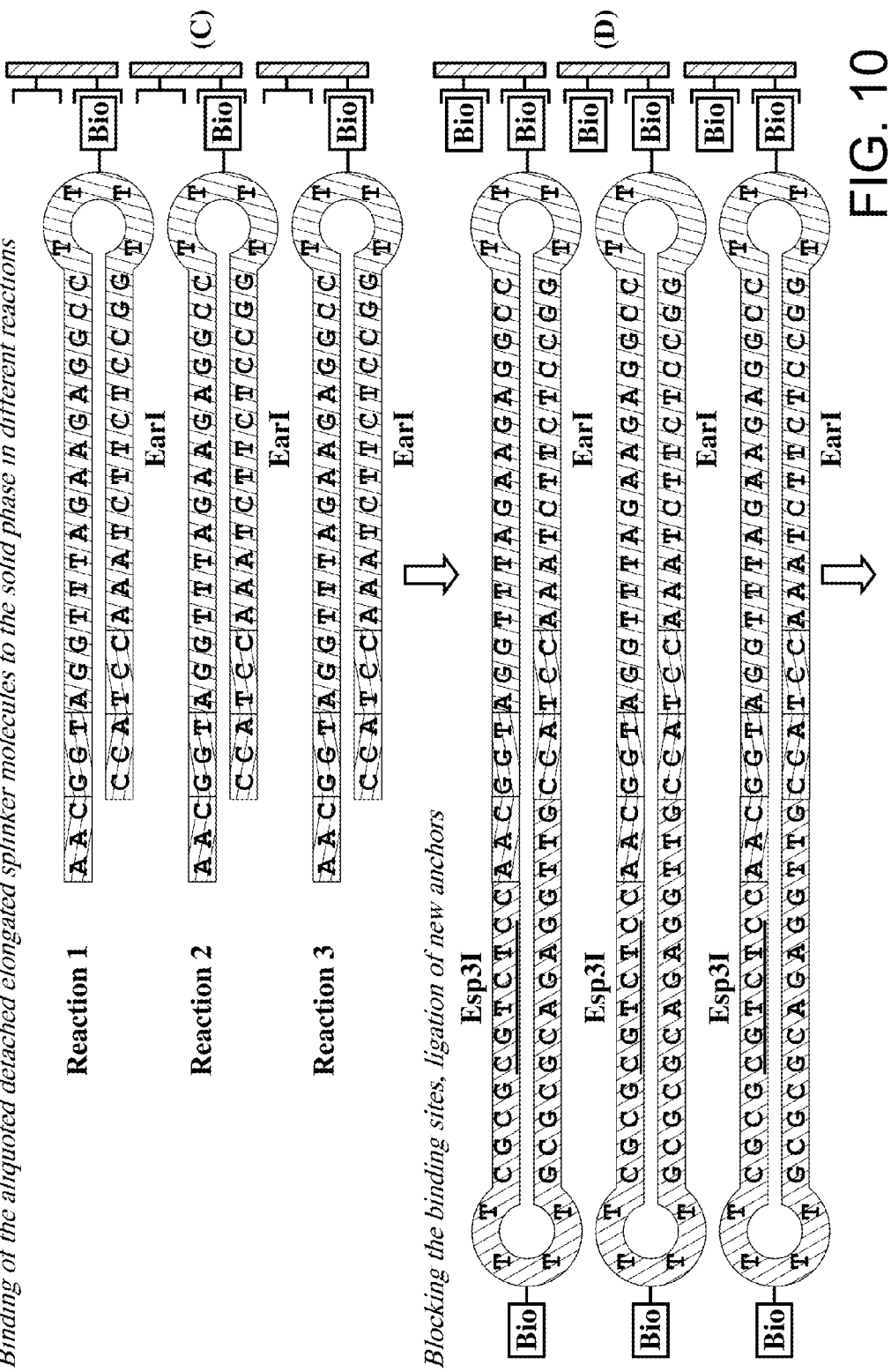

<210> SEQ ID NO 91
<211> LENGTH: 45
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 10, C (first nucleic acid from top), biotinylated

<400> SEQUENCE: 91
aacggtaggt ttagaagagg cctttggcc tcttctaaac ctacc                45

<210> SEQ ID NO 92
<211> LENGTH: 45
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 10, C (second nucleic acid from top), biotinlyated

<400> SEQUENCE: 92
aacggtaggt ttagaagagg cctttggcc tcttctaaac ctacc                45

<210> SEQ ID NO 93
<211> LENGTH: 45
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 10, C (third nucleic acid from top), biotinylated

<400> SEQUENCE: 93
aacggtaggt ttagaagagg cctttggcc tcttctaaac ctacc                45

<210> SEQ ID NO 94
<211> LENGTH: 74
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 10, D (fourth nucleic acid from top),
      double biotinylated

<400> SEQUENCE: 94
cgcgcgtctc caacggtagg tttagaagag gccttttggc ctcttctaaa cctaccgttg    60
gagacgcgcg tttt                                                     74

<210> SEQ ID NO 95
<211> LENGTH: 74
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 10, D (fifth nucleic acid from top),
      double biotinylated

<400> SEQUENCE: 95
cgcgcgtctc caacggtagg tttagaagag gccttttggc ctcttctaaa cctaccgttg    60
gagacgcgcg tttt                                                     74

<210> SEQ ID NO 96
<211> LENGTH: 74
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 10, D (sixth nucleic acid from top),
      double biotinylated

<400> SEQUENCE: 96
cgcgcgtctc caacggtagg tttagaagag gccttttggc ctcttctaaa cctaccgttg    60
gagacgcgcg tttt                                                     74

Figure 11:
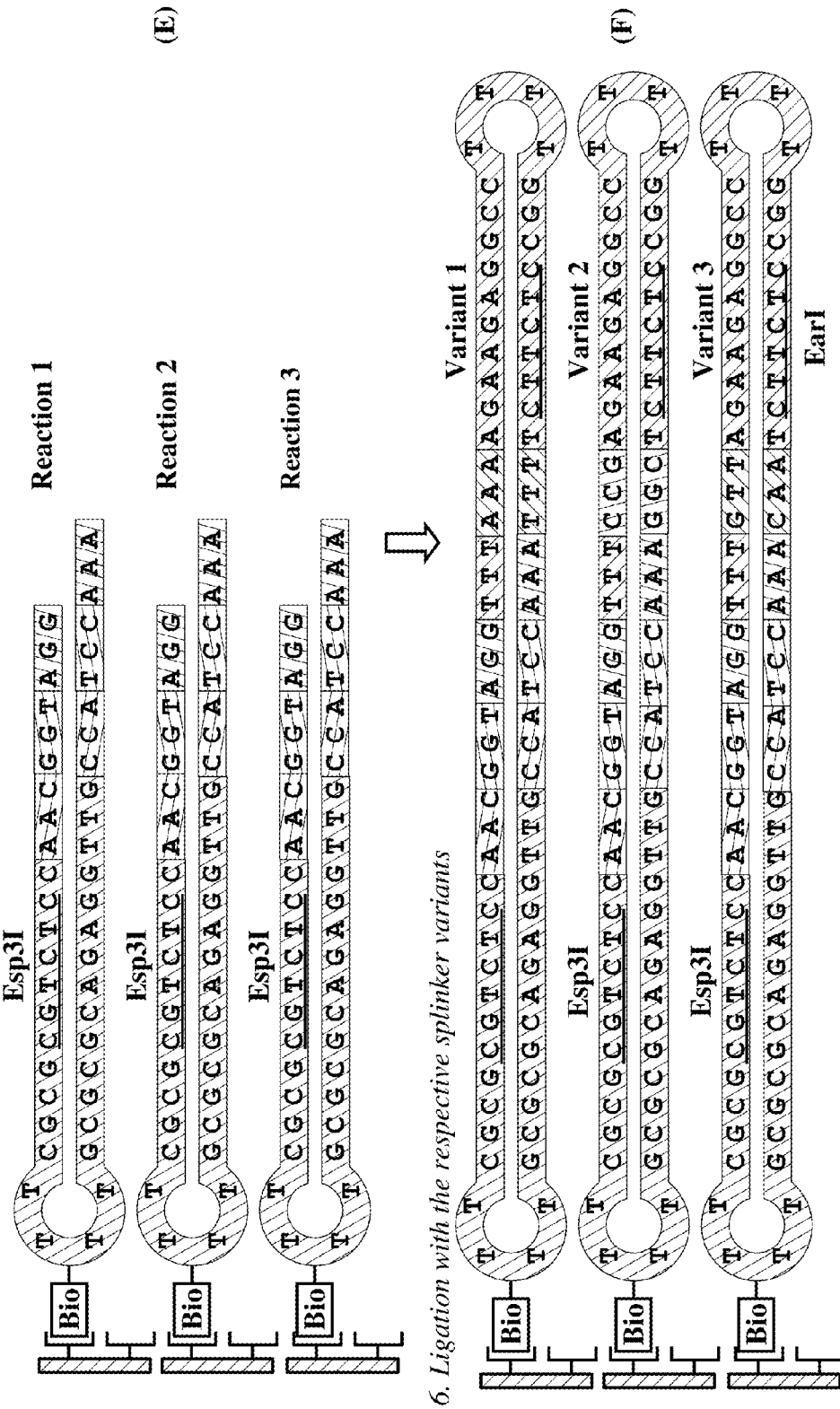

<210> SEQ ID NO 97
<211> LENGTH: 47
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 11, E (first nucleic acid from top),
      biotinylated

<400> SEQUENCE: 97
aaacctaccg ttggagacgc gcgttttcgc gcgtctccaa cggtagg                 47

<210> SEQ ID NO 98
<211> LENGTH: 47
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 11, E (second nucleic acid from top),
      biotinylated

<400> SEQUENCE: 98
aaacctaccg ttggagacgc gcgttttcgc gcgtctccaa cggtagg                47

<210> SEQ ID NO 99
<211> LENGTH: 47
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 11, E (third nucleic acid from top),
      biotinylated

<400> SEQUENCE: 99
aaacctaccg ttggagacgc gcgttttcgc gcgtctccaa cggtagg                47

<210> SEQ ID NO 100
<211> LENGTH: 80
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 11, F (fourth nucleic acid from top),
      biotinylated

<400> SEQUENCE: 100
cgcgcgtctc caacggtagg tttagaagaa gaggcctttt ggcctcttct tttaaaccta    60
ccgttggaga cgcgcgtttt                                               80

<210> SEQ ID NO 101
<211> LENGTH: 80
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 11, F (fifth nucleic acid from top),
      biotinylated

<400> SEQUENCE: 101
cgcgcgtctc caacggtagg tttccgagaa gaggcctttt ggcctcttct cggaaaccta    60
ccgttggaga cgcgcgtttt                                               80

<210> SEQ ID NO 102
<211> LENGTH: 80
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 11, F (sixth nucleic acid from top),
      biotinylated

<400> SEQUENCE: 102
cgcgcgtctc caacggtagg tttgttagaa gaggcctttt ggcctcttct cggaaaccta    60
ccgttggaga cgcgcgtttt                                               80

<210> SEQ ID NO 103

Figure 12:
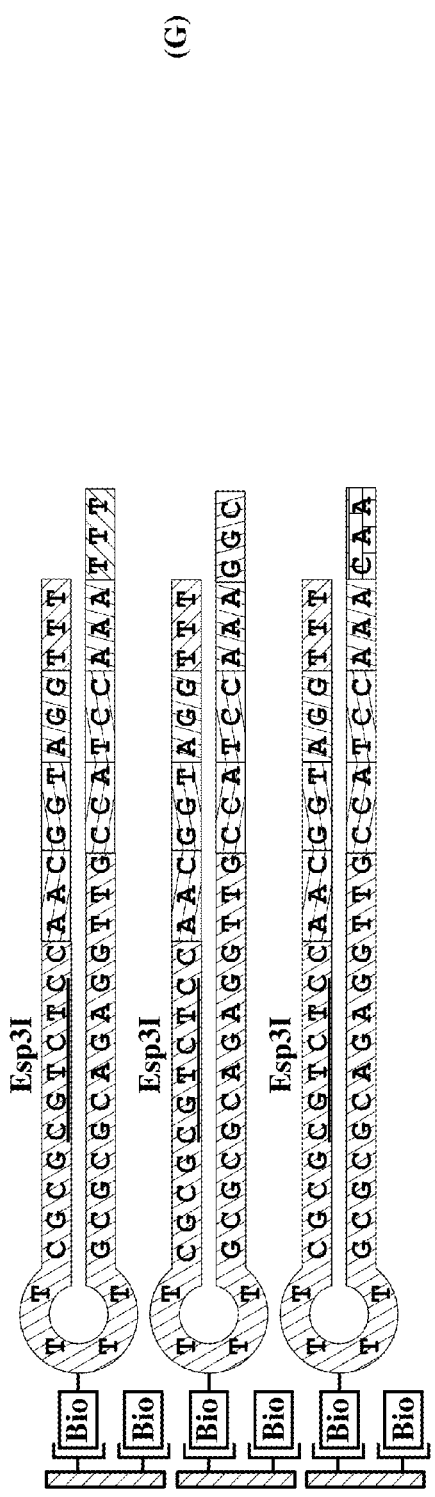
Figure 12:
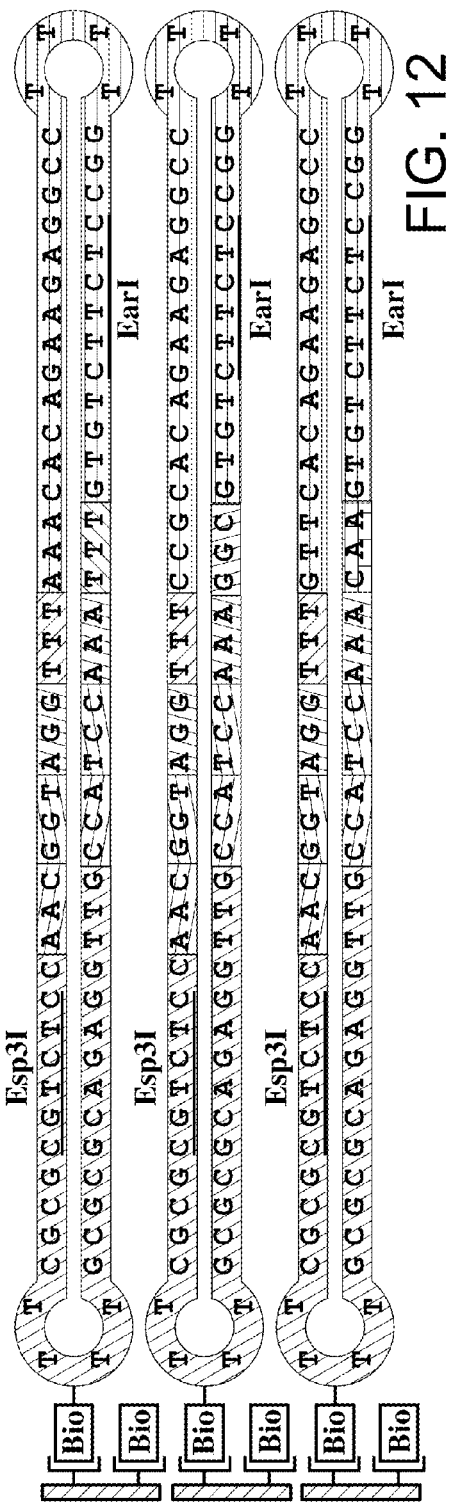

```
<211> LENGTH: 53
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 12, G (first nucleic acid from top),
      biotinylated

<400> SEQUENCE: 103
tttaaaccta ccgttggaga cgcgcgtttt cgcgcgtctc caacggtagg ttt            53

<210> SEQ ID NO 104
<211> LENGTH: 53
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 12, G (second nucleic acid from top),
      biotinylated

<400> SEQUENCE: 104
cggaaaccta ccgttggaga cgcgcgtttt cgcgcgtctc caacggtagg ttt            53

<210> SEQ ID NO 105
<211> LENGTH: 53
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 12, G (third nucleic acid from top),
      biotinylated

<400> SEQUENCE: 105
aacaaaccta ccgttggaga cgcgcgtttt cgcgcgtctc caacggtagg ttt            53

<210> SEQ ID NO 106
<211> LENGTH: 86
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 12, H (fourth nucleic acid from top),
      biotinylated

<400> SEQUENCE: 106
cgcgcgtctc caacggtagg tttaaacaca gaagaggcct tttggcctct tctgtgttta    60
aacctaccgt tggagacgcg cgtttt                                         86

<210> SEQ ID NO 107
<211> LENGTH: 86
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 12, H (fifth nucleic acid from top),
      biotinylated

<400> SEQUENCE: 107
cgcgcgtctc caacggtagg tttccgcaca gaagaggcct tttggcctct tctgtgcgga    60
```
aacctaccgt tggagacgcg cgtttt                                          86

<210> SEQ ID NO 108
<211> LENGTH: 86
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 12, H (sixth nucleic acid from top),
      biotinylated

<400> SEQUENCE: 108
cgcgcgtctc caacggtagg tttgttcaca gaagaggcct tttggcctct tctgtgaaca    60
aacctaccgt tggagacgcg cgtttt                                          86

Figure 13:
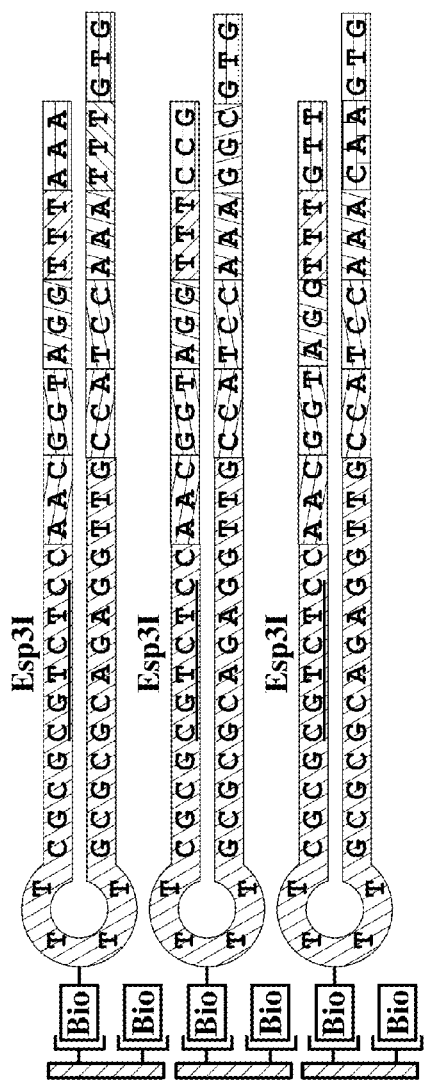
Figure 13:
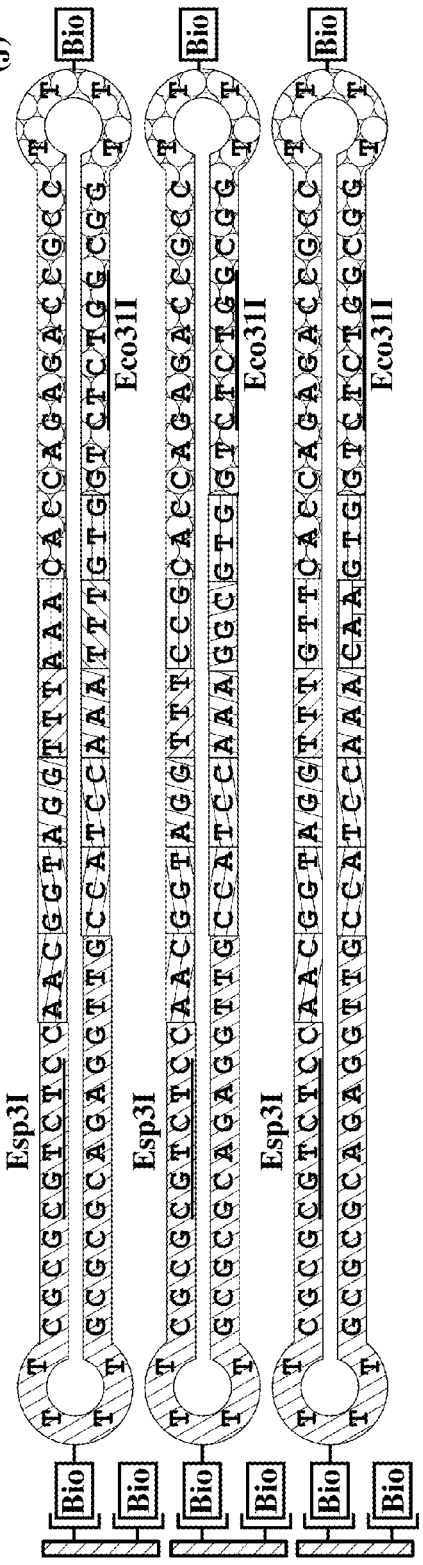

<210> SEQ ID NO 109
<211> LENGTH: 59
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 13, I (first nucleic acid from top),
      biotinylated

<400> SEQUENCE: 109
gtgtttaaac ctaccgttgg agacgcgcgt tttcgcgcgt ctccaacggt aggtttaaa     59

<210> SEQ ID NO 110
<211> LENGTH: 59
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 13, I (second nucleic acid from top),
      biotinylated

<400> SEQUENCE: 110
gtgcggaaac ctaccgttgg agacgcgcgt tttcgcgcgt ctccaacggt aggtttccg     59

<210> SEQ ID NO 111
<211> LENGTH: 59
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 13, I (third nucleic acid from top),
      biotinylated

<400> SEQUENCE: 111
gtgaacaaac ctaccgttgg agacgcgcgt tttcgcgcgt ctccaacggt aggtttgtt     59

<210> SEQ ID NO 112
<211> LENGTH: 88
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 13, J (fourth nucleic acid from top), double biotinylated

<400> SEQUENCE: 112
cgcgcgtctc caacggtagg tttaaacacc agagaccgcc ttttggcggt ctctggtgtt    60
taaacctacc gttggagacg cgcgtttt                                        88

<210> SEQ ID NO 113
<211> LENGTH: 88
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 13, J (fifth nucleic acid from top),
      double biotinylated

<400> SEQUENCE: 113
cgcgcgtctc caacggtagg tttccgcacc agagaccgcc ttttggcggt ctctggtgcg    60
gaaacctacc gttggagacg cgcgtttt                                        88

<210> SEQ ID NO 114
<211> LENGTH: 88
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 13, J (sixth nucleic acid from top),
      double biotinylated

<400> SEQUENCE: 114
cgcgcgtctc caacggtagg tttgttcacc agagaccgcc ttttggcggt ctctggtgaa    60
caaacctacc gttggagacg cgcgtttt                                        88

Figure 14:
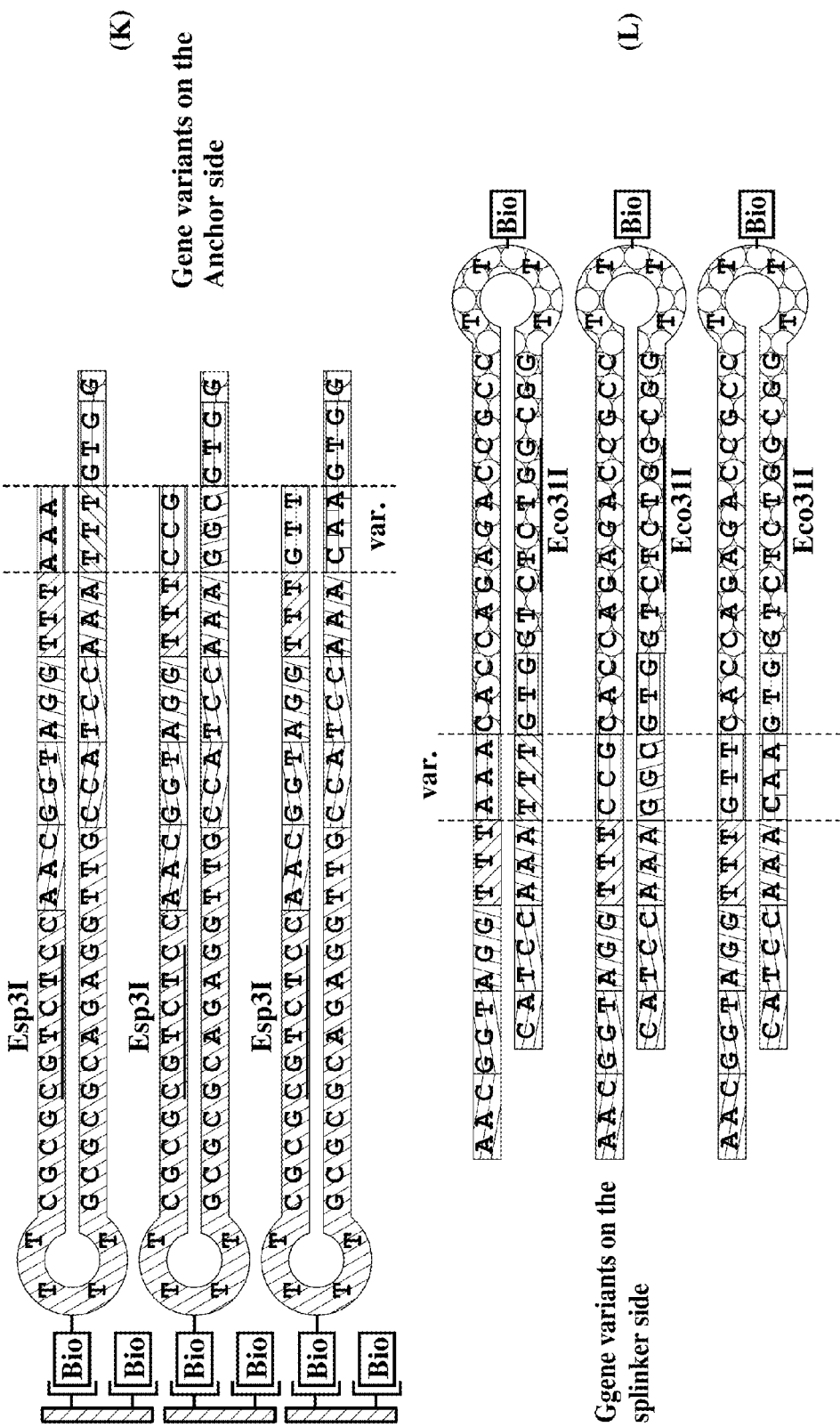

<210> SEQ ID NO 115
<211> LENGTH: 60
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 14, K (first nucleic acid from top),
      biotinylated

<400> SEQUENCE: 115
ggtgtttaaa cctaccgttg gagacgcgcg ttttcgcgcg tctccaacgg taggtttaaa    60

<210> SEQ ID NO 116
<211> LENGTH: 60
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 14, K (second nucleic acid from top),
      biotinylated

<400> SEQUENCE: 116
ggtgcggaaa cctaccgttg gagacgcgcg ttttcgcgcg tctccaacgg taggtttccg    60

<210> SEQ ID NO 117
<211> LENGTH: 60

```
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 14, K (third nucleic acid from top),
      biotinylated

<400> SEQUENCE: 117
ggtgaacaaa cctaccgttg gagacgcgcg ttttcgcgcg tctccaacgg taggtttgtt     60

<210> SEQ ID NO 118
<211> LENGTH: 58
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 14, L (fourth nucleic acid from top),
      biotinylated

<400> SEQUENCE: 118
aacggtaggt ttaaacacca gagaccgcct tttggcggtc tctggtgttt aaacctac       58

<210> SEQ ID NO 119
<211> LENGTH: 58
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 14, L (fifth nucleic acid from top),
      biotinylated

<400> SEQUENCE: 119
aacggtaggt ttccgcacca gagaccgcct tttggcggtc tctggtgcgg aaacctac       58

<210> SEQ ID NO 120
<211> LENGTH: 58
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 14,  L (sixth nucleic acid from top),
      biotinylated

<400> SEQUENCE: 120
aacggtaggt ttgttcacca gagaccgcct tttggcggtc tctggtgaac aaacctac       58

<210> SEQ ID NO 121
<211> LENGTH: 76
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 15, A (first nucleic acid from top),
      double biotinylated

<400> SEQUENCE: 121
cgcgcgtctc caacggtagg tttatgagac cgccttttgg cggtctcata aacctaccgt     60
tggagacgcg cgtttt                                                     76
```

<210> SEQ ID NO 122
<211> LENGTH: 70
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 15, B (second nucleic acid from top), biotinylated

<400> SEQUENCE: 122
cgcgcgtctc caacggtagg aagaagaggc cttttggcct cttcttccta ccgttggaga    60
cgcgcgtttt                                                            70

<210> SEQ ID NO 123
<211> LENGTH: 46
<212> TYPE: DNA
<213> ORGANISM: Artificial Sequence
<220> FEATURE:
<223> OTHER INFORMATION: Chemically synthesised
<220> FEATURE:
<221> NAME/KEY: misc_feature
<223> OTHER INFORMATION: Fig. 15 (third nucleic acid from top), biotinylated

<400> SEQUENCE: 123
aacggtaggt ttatgagacc gcctttggc ggtctcataa acctac                    46

<210> SEQ ID NO 124
<211> LENGTH: 40
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 15 (fourth nucleic acid from top)

<400> SEQUENCE: 124
aacggtagga agaagaggcc ttttggcctc ttcttcctac                          40

<210> SEQ ID NO 125
<211> LENGTH: 46
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 16 (first nucleic acid from top), biotinylated

<400> SEQUENCE: 125
aacggtaggt ttatgagacc gccttttggc ggtctcataa acctac                   46

<210> SEQ ID NO 126
<211> LENGTH: 40
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 16 (second nucleic acid from top)

<400> SEQUENCE: 126
aacggtagga agaagaggcc ttttggcctc ttcttcctac                          40

```
<210> SEQ ID NO 127
<211> LENGTH: 46
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 16 (third nucleic acid from top),
      biotinylated

<400> SEQUENCE: 127
aacggtaggt ttatgagacc gcctttggc ggtctcataa acctac                46

<210> SEQ ID NO 128
<211> LENGTH: 76
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 17, D (first nucleic acid from top),
      double biotinylated

<400> SEQUENCE: 128
cgcgcgtctc caacggtagg tttatgaaga ggccttttgg cggtctcata aacctaccgt    60
tggagacgcg cgtttt                                                   76

<210> SEQ ID NO 129
<211> LENGTH: 48
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 17, E (second nucleic acid from top),
      biotinylated

<400> SEQUENCE: 129
taaacctacc gttggagacg cgcgttttcg cgcgtctcca acggtagg              48

<210> SEQ ID NO 130
<211> LENGTH: 76
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 17, F (third nucleic acid from top),
      biotinylated

<400> SEQUENCE: 130
cgcgcgtctc caacggtagg tttatgaaga ggccttttgg cggtctcata aacctaccgt    60
tggagacgcg cgtttt                                                   76

<210> SEQ ID NO 131
<211> LENGTH: 46
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 17, H (fourth nucleic acid from top)
```

```
<400> SEQUENCE: 131
aacggtaggt ttatgaagag gcctttggc ggtctcataa acctac                46

<210> SEQ ID NO 132
<211> LENGTH: 29
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 18 (left nucleic acid of the first line
      from top)

<400> SEQUENCE: 132
gttggagacg cgcgttttcg cgcgtctcc                                  29

<210> SEQ ID NO 133
<211> LENGTH: 33
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 18 (right nucleic acid of the first line
      from top), biotinylated

<400> SEQUENCE: 133
aacaggagaa gaggccttt ggcctcttct cct                              33

<210> SEQ ID NO 134
<211> LENGTH: 62
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 18, A (nucleic acid of the second line
      from top), biotinylated

<400> SEQUENCE: 134
cgcgcgtctc caacaggaga agaggccttt tggcctcttc tcctgttgga gacgcgcgtt    60
tt                                                                  62

<210> SEQ ID NO 135
<211> LENGTH: 35
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 18, B (left nucleic acid of the third
      line from top)

<400> SEQUENCE: 135
cctgttggag acgcgcgttt tcgcgcgtct ccaac                           35

<210> SEQ ID NO 136
<211> LENGTH: 27
<212> TYPE: DNA
<213> ORGANISM: Artificial Sequence
<220> FEATURE:
<223> OTHER INFORMATION: Chemically synthesized
<220> FEATURE:
```

```
<221> NAME/KEY: misc_feature
<223> OTHER INFORMATION: Fig. 18, B (right nucleic acid of the third
      line from top), biotinylated

<400> SEQUENCE: 136
aggagaagag gccttttggc ctcttct                                          27

<210> SEQ ID NO 137
<211> LENGTH: 33
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 19 (first nucleic acid from top),
      biotinylated

<400> SEQUENCE: 137
aacaggagaa gaggcctttt ggcctcttct cct                                   33

<210> SEQ ID NO 138
<211> LENGTH: 62
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 19, C (second nucleic acid from top),
      biotinylated

<400> SEQUENCE: 138
cgcgcgtctc caacaggaga agaggccttt tggcctcttc tcctgttgga gacgcgcgtt      60
tt                                                                     62

<210> SEQ ID NO 139
<211> LENGTH: 27
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 19 (third nucleic acid from top),
      biotinylated

<400> SEQUENCE: 139
aggagaagag gccttttggc ctcttct                                          27

<210> SEQ ID NO 140
<211> LENGTH: 35
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 19, D (fourth nucleic acid from top)

<400> SEQUENCE: 140
cctgttggag acgcgcgttt tcgcgcgtct ccaac                                 35

<210> SEQ ID NO 141
<211> LENGTH: 35
<212> TYPE: DNA
<213> ORGANISM: Artificial Sequence
<220> FEATURE:
```

<223> OTHER INFORMATION: Chemically synthesized
<220> FEATURE:
<221> NAME/KEY: misc_feature
<223> OTHER INFORMATION: Fig. 20 (left nucleic acid of the first line
      from top)

<400> SEQUENCE: 141
cctgttggag acgcgcgttt tcgcgcgtct ccaac                                    35

<210> SEQ ID NO 142
<211> LENGTH: 33
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 20 (right nucleic acid of the first line
      from top), biotinylated

<400> SEQUENCE: 142
aggcatagaa gaggcctttt ggcctcttct atg                                     33

<210> SEQ ID NO 143
<211> LENGTH: 68
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 20, E (nucleic acid of the second line
      from top), biotinylated

<400> SEQUENCE: 143
cgcgcgtctc caacaggcat agaagaggcc ttttggcctc ttctatgcct gttggagacg        60
cgcgtttt                                                                 68

<210> SEQ ID NO 144
<211> LENGTH: 41
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 20, F (left nucleic acid of the third
      line from top)

<400> SEQUENCE: 144
atgcctgttg gagacgcgcg ttttcgcgcg tctccaacag g                            41

<210> SEQ ID NO 145
<211> LENGTH: 27
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 20, F (right nucleic acid of the third
      line from top), biotinylated

<400> SEQUENCE: 145
catagaagag gccttttggc ctcttct                                            27

<210> SEQ ID NO 146
<211> LENGTH: 30

```
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 21, A (left nucleic acid of the first
      line from top), biotinylated

<400> SEQUENCE: 146
agaccgagac gcgcgttttc gcgcgtctcg                                            30

<210> SEQ ID NO 147
<211> LENGTH: 36
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 21 (right nucleic acid of the first line
      from top)
<220> FEATURE:
<221> NAME/KEY: misc_feature
<222> LOCATION: (3)..(3)
<223> OTHER INFORMATION: methylated

<400> SEQUENCE: 147
gtctcgagtg agaccgcctt ttggcggtct cactcg                                     36

<210> SEQ ID NO 148
<211> LENGTH: 66
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 21 (nucleic acid of the second line from
      top), biotinylated
<220> FEATURE:
<221> NAME/KEY: misc_feature
<222> LOCATION: (14)..(14)
<223> OTHER INFORMATION: methylated
<220> FEATURE:
<221> NAME/KEY: misc_feature
<222> LOCATION: (50)..(50)
<223> OTHER INFORMATION: methylated

<400> SEQUENCE: 148
cgcgcgtctc ggtctcgagt gagaccgcct tttggcggtc tcactcgaga ccgagacgcg           60
cgtttt                                                                     66

<210> SEQ ID NO 149
<211> LENGTH: 38
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 21, B (left nucleic acid of the third line
      from top), biotinylated
<220> FEATURE:
<221> NAME/KEY: misc_feature
<222> LOCATION: (7)..(7)
<223> OTHER INFORMATION: methylated
<220> FEATURE:
<221> NAME/KEY: misc_feature
<222> LOCATION: (38)..(38)
<223> OTHER INFORMATION: methylated
```

```
<400> SEQUENCE: 149
ctcgagaccg agacgcgcgt tttcgcgcgt ctcggtct                              38

<210> SEQ ID NO 150
<211> LENGTH: 28
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 21 (right nucleic acid of the third line
      from top)

<400> SEQUENCE: 150
cgagtgagac cgcctttTgg cggtctca                                         28

<210> SEQ ID NO 151
<211> LENGTH: 38
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 22, C (left nucleic acid of the first line
      from top), biotinylated
<220> FEATURE:
<221> NAME/KEY: misc_feature
<222> LOCATION: (7)..(7)
<223> OTHER INFORMATION: methylated
<220> FEATURE:
<221> NAME/KEY: misc_feature
<222> LOCATION: (37)..(37)
<223> OTHER INFORMATION: methylated

<400> SEQUENCE: 151
ctcgagaccg agacgcgcgt tttcgcgcgt ctcggtct                              38

<210> SEQ ID NO 152
<211> LENGTH: 36
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 22 (right nucleic acid of the first line
      from top)

<400> SEQUENCE: 152
cgagcatatg agaccgcctt ttggcggtct catatg                                36

<210> SEQ ID NO 153
<211> LENGTH: 74
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 22 (nucleic acid of the second line from
      top), biotinylated
<220> FEATURE:
<221> NAME/KEY: misc_feature
<222> LOCATION: (14)..(14)
<223> OTHER INFORMATION: methylated
<220> FEATURE:
<221> NAME/KEY: misc_feature
<222> LOCATION: (58)..(58)
<223> OTHER INFORMATION: methylated
```

<400> SEQUENCE: 153
cgcgcgtctc ggtctcgagc atatgagacc gccttttggc ggtctcatat gctcgagacc      60
gagacgcgcg tttt                                                         74

<210> SEQ ID NO 154
<211> LENGTH: 46
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 22, D (left nucleic acid of the third line
      from top), biotinylated
<220> FEATURE:
<221> NAME/KEY: misc_feature
<222> LOCATION: (11)..(11)
<223> OTHER INFORMATION: methylated
<220> FEATURE:
<221> NAME/KEY: misc_feature
<222> LOCATION: (41)..(41)
<223> OTHER INFORMATION: methylated

<400> SEQUENCE: 154
tatgctcgag accgagacgc gcgttttcgc gcgtctcggt ctcgag                      46

<210> SEQ ID NO 155
<211> LENGTH: 28
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 22 (right nucleic acid of the third line
      from top)

<400> SEQUENCE: 155
catatgagac cgccttttgg cggtctca                                          28

<210> SEQ ID NO 156
<211> LENGTH: 38
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 23 (left nucleic acid of the first line
      from top), biotinylated

<400> SEQUENCE: 156
accgtttgag acgcgcgttt tcgcgcgtct caaacggt                               38

<210> SEQ ID NO 157
<211> LENGTH: 18
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 23 (left, overlepped nucleic acid, i.e.
      5'-primer, of the first line from top)

-continued

<400> SEQUENCE: 157
gcgaaaacgc gcgtctca                                                    18

<210> SEQ ID NO 158
<211> LENGTH: 44
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 23 (right nucleic acid of the first line
      from top)

<400> SEQUENCE: 158
tttaaacacc agagaccgcc ttttggcggt ctctggtgtt taaa                       44

<210> SEQ ID NO 159
<211> LENGTH: 17
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 23 (right overlapped nucleic acid, i.e.
      3'-primer, of the first line from top)

<400> SEQUENCE: 159
gccaaaaggc ggtctct                                                     17

<210> SEQ ID NO 160
<211> LENGTH: 24
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 23 (left upper nucleic acid of the left
      nucleic acid in the second line from top)

<400> SEQUENCE: 160
gcgaaaacgc gcgtctcaaa cggt                                             24

<210> SEQ ID NO 161
<211> LENGTH: 24
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 23 (left below, i.e. complementary
      sequence of the left nucleic acid in the second line from top)

<400> SEQUENCE: 161
accgtttgag acgcgcgttt tcgc                                             24

<210> SEQ ID NO 162
<211> LENGTH: 26
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 23 (right upper sequence of the right nucleic acid in the second column from top)

<400> SEQUENCE: 162
tttaaacacc agagaccgcc ttttgg                                              26

<210> SEQ ID NO 163
<211> LENGTH: 26
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 23 (complementary sequence to the right
      upper sequence of the right nucleic acid in the second line from
      top)

<400> SEQUENCE: 163
ccaaaaggcg gtctctggtg tttaaa                                              26

<210> SEQ ID NO 164
<211> LENGTH: 24
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 23, B (upper sequence of the left nucleic
      acid in the third line from top)

<400> SEQUENCE: 164
gcgaaaacgc gcgtctcaaa cggt                                                24

<210> SEQ ID NO 165
<211> LENGTH: 24
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 23 (complementary sequence of the left
      sequence in the third line from top)

<400> SEQUENCE: 165
accgtttgag acgcgcgttt tcgc                                                24

<210> SEQ ID NO 166
<211> LENGTH: 26
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Fig. 23 (upper sequence of the left nucleic
      acid in the third line from top)

<400> SEQUENCE: 166
tttaaacacc agagaccgcc ttttgg                                              26

<210> SEQ ID NO 167
<211> LENGTH: 26
<212> TYPE: DNA
<213> ORGANISM: Artificial Sequence
<220> FEATURE:
<223> OTHER INFORMATION: Chemically synthesized
<220> FEATURE:

```
<221> NAME/KEY: misc_feature
<223> OTHER INFORMATION: Fig. 23 (complementary sequence to the right,
      upper sequence in the third line from top)

<400> SEQUENCE: 167
ccaaaaggcg gtctctggtg tttaaa                                            26
```

NUCLEIC ACID SYNTHESIS METHODS

The present invention relates to single and double-stranded nucleic acid molecules for use in a procedure for the production of a nucleic acid, a procedure for the production of a nucleic acid as well as a kit for the production of a nucleic acid.

The synthesis of nucleic acids has many kinds of applications in modern biotechnology. Apart from the synthesis of comparatively short nucleic acids like oligonucleotides the focus is increasingly on large nucleic acids of several kilobases. For each gene the methods employed generally use different synthetically produced oligonucleotides, typically 40-100 nucleotides in length as basic modules. As a consequence of the multitude of necessary reactions steps—despite high coupling efficiencies of typically approximately 98-99% per step, —they contain degradation products as well as abortive sequences which are detrimental for the quality of the nucleic acids to be synthesized. Such errors are especially detrimental when the nucleic acid to be synthesized is a coding sequence and thus the shift of the reading frame leads to shortened transcription- or translation products. Therefore the oligonucleotide building blocks need to be additionally purified to reduce these errors to an acceptable degree since complex gene synthesis is otherwise practically impossible. To the procedures known in the state of the art belongs the so called "gap filling" procedure, in which a multitude of oligonucleotides is synthesized, purified and subsequently hybridized either pair-wise or in sub-groups. After the synthesis of the respective complementary strands by a Klenow polymerase reaction, the individual fragments are ligated to each other.

The thus formed ligation products can either be cloned as sub-fragments or first be hybridized with flanking oligonucleotide primers and amplified by a polymerase chain reaction. Alternatively complementary oligonucleotides can be hybridized in the framework of the so called "cassette method" and the obtained gene fragments can be linked by enzymatic or chemical ligation. After purification and/or cloning these can be assembled into larger gene segments.

Both procedures have disadvantages for example caused by errors in the Klenow Polymerase reaction or in the polymerase chain reaction which increase with the length of the nucleic acid to be synthesized. Additionally there are procedures known in the state of the art in which oligonucleotides are assembled in a solid phase synthesis to build up larger nucleic acids.

For example, the international patent application WO 99/47536 describes a recursive procedure in which single-stranded oligonucleotides are sequentially ligated to an immobilized starter molecule in a defined orientation. A disadvantage of this procedure is the high number of single steps required for larger gene synthesis which as a consequence of the principle lead to low yield and the accumulation of sequence errors. In addition all oligonucleotides used for the respective synthesis must first be synthesized. Due to the inherent high technical complexity, a standardization of this procedure is only possible in a limited way.

International patent application WO 00/75368 describes a combinatorial solid phase synthesis, in which double-stranded oligonucleotides containing a recognition sequence for a type IIS restriction enzyme are ligated, in parallel reactions, to further oligonucleotides containing a recognition sequence for a different type IIS restriction enzyme followed by digestion of the ligation products with a type IIS restriction enzyme. Thus a defined nucleic acid is iteratively built by multiple repetitions of the same steps.

This procedure is advantageous compared to other procedures based on the ligation of oligonucleotides in that the oligonucleotides used contain recognition sequences for different type IIS restriction enzymes, which allow a sequence-independent combination of sub-fragments ligated in parallel. Thereby any desired sub-fragments can be produced from a standardized nucleic acid library with a defined number of elements. The number of elements building up this library is dependent on the length of the overhangs produced by the respective restriction enzyme. For example, based on an overhang of four nucleotides a complete library consists of a total of 65.536 elements. This figure results from the number of sequence variants which exist for an overhang of 4 nucleotides ($4^4=256$) multiplied with the number of sequence variants for the four directly adjacent nucleotides that form the overhang in the next ligation step ($4^4 \times 4^4 = 65.536$).

Despite the fact that this procedure allows for a sequence independent ligation of any desired subfragments produced in parallel and thus forms the basis for automation, the number of oligonucleotides needed for building up a corresponding library which is accessed for the synthesis is still comparatively high. A further aspect which needs to be considered is the length of the oligonucleotides that are used in such a procedure (typically 20-40 nucleotides). As a consequence a complete library in the described case contains a total of $65.536 \times 40 \approx 2.6$ Mio. nucleotides Despite the advantages directly connected with the procedure according to WO 00/75368 in the state of the art there is still the need for a procedure for the synthesis of nucleic acids and means for its implementation which are based on an oligonucleotide library of smaller complexity. In particular, the complexity for the production of a complete library mainly with respect to the number of nucleotides necessary is to be significantly reduced compared to the state of the art, without having to accept disadvantages like a reduced ligation efficiency (for example when using overhangs of only one or two nucleotides). It is thus an additional problem of the invention to provide a procedure which guarantees a further reduction of the number of incomplete and faulty sequences as well as to allow for the simultaneous synthesis of several variants of the respective gene.

According to the invention this problem is solved in a first aspect by a single-stranded nucleic acid molecule for use in a method for the production of a nucleic acid comprising at least a (constant) part A and a (variable) part B whereby Part A comprises a sequence, which corresponds to a recognition site or a part thereof or a sequence complementary thereto of a type IIS restriction enzyme, and Part B comprises a defined sequence of nucleotides In one embodiment it is intended that the restriction enzyme is chosen from the group which comprises BpiI, Esp3I, Eco31I, BsaI, BsmBI, BbsI, BspMI, AarI, AceIII, Acc36I, SapI, BtsI, BsrDI, Bse3DI, BciVI, BfuI, BfiI and BmrI.

In a further embodiment it is intended that the sequence of part A is chosen from the group comprising the SEQ ID Nos 1 to 13. In still another embodiment it is intended that part B has a length of 1, 2, 3, 4, 5, 6 or 7 nucleotides.

In a second aspect the problem is solved by a nucleic acid molecule library containing a multitude of nucleic acid molecules according to the invention. In one embodiment it is intended that the library contains 256 members, which are different in part B of the sequence, whereby the defined sequence of nucleotides of part B has a length of four nucleotides.

In another embodiment it is intended that the library comprises 1024 members that differ in part B of the sequence, whereby the defined sequence of nucleotides of part B has a length of five nucleotides.

In yet another embodiment it is intended that the library comprises 4096 members that differ in part B of the sequence, whereby the defined sequence of nucleotides of part B has a length of six nucleotides.

In another embodiment it is intended that the library comprises 16 members that differ in part B of the sequence, whereby the defined sequence of nucleotides of part B has a length of two nucleotides.

Finally, in one embodiment it is intended that the library comprises 64 members that differ in part B of the sequence, whereby the defined sequence of nucleotides of part B has a length of three nucleotides.

In a third aspect the problem is solved by using at least one of the nucleic acid molecules according to the invention and/or one of the nucleic acid libraries according to the invention in a method for the production of nucleic acids, particularly in a procedure for a sequential ligation of oligonucleotides in parallel reactions which are assembled in additional steps in a sequence-independent manner.

In a fourth aspect the problem is solved by a method for the production of a nucleic acid molecule comprising the steps:
 a) providing a first oligonucleotide, optionally coupled to a surface via a modification, whereby the oligonucleotide comprises a recognition site or a part thereof or a sequence complementary thereto for a first type IIS restriction enzyme cutting outside its recognition site, and a single-stranded overhang,
 b) adding a single-stranded nucleic acid molecule according to one of the claims 1 to 4 to the oligonucleotide, whereby part A of the nucleic acid molecule is preferably essentially complementary to the single-stranded region of the first oligonucleotide;
 c) ligation of the nucleic acid molecule of step b) with the first oligonucleotide thus forming a 5' overhang;
 d) filling in the 5' overhang;
 e) providing a second oligonucleotide, whereby the oligonucleotide comprises a recognition site or a part thereof or a sequence complementary thereto for a second type IIS restriction enzyme, which cleaves outside its recognition site, and comprises a single-stranded overhang, whereby the recognition site of the restriction enzyme is different from the recognition site of the restriction enzyme referred to in step a), and
 f) adding a single-stranded nucleic acid molecule according to one of the claims 1 to 4 to the oligonucleotide, whereby part A of the nucleic acid molecule is preferably basically complementary to the single-stranded region of the second oligonucleotide;
 g) ligating the nucleic acid molecule of step f) with the second oligonucleotide thus forming a 5' overhang;
 h) filling in the 5' overhang;
 i) ligation of the oligonucleotides obtained from steps a) to d) and e) to h);
 j) cleavage of the ligation product obtained in step i) with the first or with the second type IIS restriction enzyme.

In one embodiment it is intended that in step b) and/or f) a hybridization occurs between the single-stranded portion of the oligonucleotide and part A of the single-stranded nucleic acid molecule.

In a further embodiment it is intended that the first oligonucleotide is coupled to a solid phase and preferentially cleaved off the solid phase before the ligation according to step i).

In a fifth aspect the problem is solved by a kit for the production of a nucleic acid containing one of the nucleic acid libraries according to the invention or a part thereof.

In one embodiment it is intended the kit comprises a first oligonucleotide comprising a recognition site for a first type IIS restriction enzyme.

In another embodiment it is intended that the kit contains a second oligonucleotide comprising a recognition site or a part thereof or a sequence complementary thereto for a second type IIS restriction enzyme, whereby the second restriction enzyme is different from the first restriction enzyme.

In yet another embodiment it is intended that at least one of the oligonucleotides is bound to a solid phase.

In a sixth aspect the invention relates to a method for the enzymatic production of a partially double-stranded oligonucleotide with a 3 nucleotide overhang, whereby the oligonucleotide contains a recognition site for a type IIS restriction enzyme, comprising the steps:
 a) Providing a first partially double-stranded oligonucleotide, whereby the oligonucleotide possesses a 3'-overhang and a recognition site for a type IIS restriction enzyme,
 b) providing a first group of single-stranded oligonucleotides comprising a part A and a part B, whereby part A is complementary to the single-stranded region of the first oligonucleotide provided in step a) and preferably identical in all members of the group, and part B has a length of 3 nucleotides, whereby the members of the group differ in part B,
 c) providing a second partially double-stranded oligonucleotide, whereby the oligonucleotide possesses a 3'-overhang and a recognition site for a type IIS restriction enzyme, whereby the type IIS restriction enzyme is different from the type IIS restriction enzyme of the oligonucleotide in step a),
 d) providing a second group of single-stranded oligonucleotides comprising a part A and a part B, whereby part A is complementary to the single-stranded region of the first oligonucleotide provided in step a) and is preferably identical in all members of the group, and part B has a length of 3 nucleotides, whereby the members of the group differ in part B,
 e) hybridizing and ligating the first oligonucleotide provided in step a) with one member respectively of the first group of single-stranded oligonucleotides provided in step b),
 f) hybridizing and ligating the second oligonucleotide provided in step c) with one member respectively of the second group of single-stranded oligonucleotides provided in step d)
 g) filling in the 5' overhangs of the ligation products from step e),
 h) filling in the 5' overhangs of the ligation products from step f),
 i) ligation of one filled in ligation product respectively from step g) with one filled in ligation step respectively from step h),
 j) cleavage of the ligation product from step i) with the type IIS restriction enzyme specific for the oligonucleotide provided in step a)

In a seventh aspect the invention relates to a method for the enzymatic production of a partially double-stranded oligonucleotide with a 3 nucleotide overhang, whereby the oligonucleotide contains a recognition site for a type IIS restriction enzyme and digestion of the oligonucleotide with the restriction enzyme leads to an overhang with a length different from 3 nucleotides, comprising the steps:

a) Providing a first partially double-stranded oligonucleotide, whereby the oligonucleotide possesses a 3'-overhang and a recognition site for a type IIS restriction enzyme,
b) providing a first group of single-stranded oligonucleotides comprising a part A and a part B, whereby part A is complementary to the single-stranded region of the first oligonucleotide provided in step a) and is preferably identical in all members of the group and part B has a length of 2 nucleotides, whereby the members of the group differ in part B,
c) providing a second partially double-stranded oligonucleotide, whereby the oligonucleotide possesses a 3'-overhang and a recognition site for a type IIS restriction enzyme, whereby the type IIS restriction enzyme is different from the type IIS restriction enzyme of the oligonucleotides in step a),
d) providing a second group of single-stranded oligonucleotides comprising a part A and a part B, whereby part A is complementary to the single-stranded region of the first oligonucleotide provided in step a) and is preferably identical in all members of the group and part B has a length of 2 nucleotides, whereby the members of the group differ in part B,
e) hybridizing and ligating the first oligonucleotide provided in step a) with one member respectively of the first group of single-stranded oligonucleotides provided in step b),
f) hybridizing and ligating the first oligonucleotide provided in step c) with one member respectively of the first group of single-stranded oligonucleotides provided in step d),
g) filling in the 5' overhangs of the ligation products from step e),
h) filling in the 5' overhangs of the ligation products from step f),
i) ligation of one filled in ligation product respectively from step g) with one ligation step respectively from step h),
j) cleavage of the ligation product from step i) with the type IIS restriction enzyme specific for the oligonucleotide provided in step a)

In an eighth aspect the invention relates to a method for the production of a nucleic acid molecule comprising the steps a) providing an oligonucleotide, generated by the following steps:
aa) providing a partially double-stranded oligonucleotide with a 5'-overhang, containing a recognition site for a type IIS restriction enzyme cleaving outside of its recognition site, and carrying a modification, which allows coupling to a solid matrix, whereby the 5'-overhang has a length of 3 nucleotides,
ab) addition of a further, at least partially double-stranded oligonucleotide with a 5'-overhang and a different recognition site for a type IIS restriction enzyme, which cleaves outside of its recognition site, than in step aa), whereby the 5'-overhang has a length of 3 nucleotides,
ac) ligation of the oligonucleotides from step aa) and ab) in the orientation defined by the blocking of the ends not to be ligated,
ad) removing unused reactants as well as enzymes,
ae) cleavage of the ligation product from step ac) with a type IIS restriction enzyme, which cleaves outside of its recognition site, whereby the cleavage occurs in the nucleic acid sequence of the oligonucleotide from step ab),
af) separation of the reaction mixture from the elongated oligonucleotide obtained in step ae), which had been provided in step aa),
ag) optionally repeating steps ab) to af) at least one time,
b) providing a further oligonucleotide, generated by the steps:
ba) providing a partially double-stranded oligonucleotide with a 5'-overhang, containing a recognition site for a type IIS restriction enzyme, which cuts outside of its recognition site, and carrying a modification, which allows coupling to a solid matrix, whereby the 5'-overhang has a length of 3 nucleotides,
bb) addition of a further, at least partially double-stranded oligonucleotide with a 5'-overhang and with a different recognition site for a type IIS restriction enzyme, which cleaves outside of its recognition site, than in step ba), whereby the 5'-overhang has a length of 3 nucleotides,
bc) ligation of the oligonucleotides from step ba) and bb) in the orientation defined by the blocking of the ends not to be ligated,
bd) removing unused reactants as well as enzymes,
be) cleavage of the ligation product from step bc) with a type IIS restriction enzyme, which cleaves outside of its recognition site, whereby the cleavage occurs in the nucleic acid sequence of the oligonucleotide from step bb),
bf) separation of the thus elongated oligonucleotide from the reaction mixture,
bg) optionally repeating steps bb) to be) at least one time, whereby subsequent to the last ligation in step bc) and removal of unused reactants as well as enzymes, the ligation product is cleaved with a type IIS restriction enzyme, whereby the cleavage occurs in the oligonucleotide from step ba),
c) ligation of the oligonucleotides from step a) and b) in the orientation defined by the blocking of the ends not to be ligated,
d) removal of unused reactants as well as enzymes,
e) cleavage of the ligation product from step c) with a type IIS restriction enzyme, which cleaves outside of its recognition site, whereby the cleavage occurs in the oligonucleotide from step a) or b),
f) separating the thus elongated nucleic acid molecule from the reaction mixture, characterized in that the oligonucleotide of step ab) contains the recognition site for a type IIS restriction enzyme, which generates an overhang three nucleotides in length as long as steps ab) to ae) are repeated and the oligonucleotide of step ab) possesses the recognition site of a type IIS restriction enzyme, which produces an overhang other than three nucleotides in length, in the last cycle of the steps ab) to ae) and/or
the oligonucleotide from step bb) contains the recognition site for a type IIS restriction enzyme, which generates an overhang three nucleotides in length as long as steps bb) to be) are repeated and the oligonucleotide of step bb) possesses the recognition site of a type IIS restriction enzyme, which produces an overhang other than three nucleotides in length, in the last cycle of the steps bb) to be).

In a ninth aspect the invention relates to a method for the production of a group of nucleic acid molecules comprising the steps:

a) providing an oligonucleotide, generated by the following steps:
aa) providing an oligonucleotide, containing a recognition site for a type IIS restriction enzyme cutting outside of its recognition site, and carrying a modification, which allows coupling to a solid matrix,
coupling the oligonucleotides to the solid matrix,
ab) addition of a further, at least partially double-stranded oligonucleotide with a different recognition site for a type IIS restriction enzyme, cutting outside of its recognition site, than in step aa),
ac) ligation of the oligonucleotides from step aa) and ab) in the orientation defined by the blocking of the ends not to be ligated,
ad) removing unused reactants as well as enzymes,
ae) cleavage of the ligation product from step ac) with a type IIS restriction enzyme, which cleaves outside of its recognition site, whereby the cleavage occurs in the nucleic acid sequence of the oligonucleotide from step ab),
af) separating the reaction mixture from the elongated oligonucleotide obtained in step ae), first provided in step aa),
ag) optionally repeating steps ab) to af) at least one time,
b) providing a further oligonucleotide, generated by the steps:
ba) providing a partially double-stranded oligonucleotide, containing a recognition site for a type IIS restriction enzyme, which cuts outside of its recognition site, and carrying a modification, which allows coupling to a solid matrix, with one end to a solid matrix,
coupling of the oligonucleotide to the solid matrix,
bb) addition of a further, at least partially double-stranded oligonucleotide with a different recognition site for a type IIS restriction enzyme site than in step ba), which cleaves outside of its recognition,
bc) ligation of the oligonucleotides from step ba) and bb) in the orientation defined by the blocking of the ends not to be ligated,
bd) removing unused reactants as well as enzymes,
be) cleavage of the ligation product from step bc) with a type IIS restriction enzyme, which cleaves outside of its recognition site, whereby the cleavage occurs in the nucleic acid sequence of the oligonucleotide from step bb),
bf) separating the thus elongated oligonucleotide from the reaction mixture,
bg) optionally repeating steps bb) to bf) at least one time, whereby subsequent to the last ligation in step bc) and removing unused reactants as well as enzymes the ligation product is cleaved with a type IIS restriction enzyme, whereby the cleavage occurs in the oligonucleotide from step ba),
c) ligation of the oligonucleotides from step a) and b) in the orientation defined by the blocking of the ends not to be ligated,
d) removing unused reactants as well as enzymes,
e) cleavage of the ligation product from step c) with a type IIS restriction enzyme, which cleaves outside of its recognition site, whereby the cleavage occurs in the oligonucleotide from step a) or b),
f) separating of the thus elongated nucleic acid molecules from the reaction mixture,
characterized in that in the last repetition of steps ab) to af) the oligonucleotide added in step ab) carries a modification, which allows coupling to a solid matrix and after the last repetition of steps ab) to af), as step ah), the ligation product from step ac) is cut with a type IIS restriction enzyme, which cleaves outside of its recognition site, whereby the cleavage occurs in the nucleic acid sequence of the oligonucleotide from step aa), and the cleavage product of the oligonucleotide coupled to the solid matrix is released,
and the released cleavage product is divided into at least two reactions.

In a tenth aspect the problem is solved by a method for the production of a nucleic acid molecule comprising the steps of:
a) Providing an oligonucleotide, generated by the following steps:
aa) providing an oligonucleotide, containing a recognition site for a type IIS restriction enzyme cutting outside of its recognition site, and carrying a modification, which allows coupling to a solid matrix,
coupling the oligonucleotide to the solid matrix,
ab) addition of a further, at least partially double-stranded oligonucleotide with another recognition site for a type IIS restriction enzyme, cutting outside of its recognition site, than in step aa),
ac) ligation of the oligonucleotides from step aa) and ab) in the orientation defined by the blocking of the ends not to be ligated,
ad) removing unused reactants as well as enzymes,
ae) cleavage of the ligation product from step ac) with a type IIS restriction enzyme, which cleaves outside of its recognition site, whereby the cleavage occurs in the nucleic acid sequence of the oligonucleotide from step ab),
af) separating the reaction mixture from the elongated oligonucleotide obtained in step ae), first provided in step aa),
ag) optionally repeating steps ab) to af) at least one time,
b) providing a further oligonucleotide, generated by the steps:
ba) Providing an oligonucleotide containing a recognition site for a type IIS restriction enzyme, which cuts outside of its recognition site, and carrying a modification, which allows coupling to a solid matrix, with one end to the solid matrix,
coupling of the oligonucleotide to the solid matrix,
bb) addition of a further, at least partially double-stranded oligonucleotide with a different recognition site for a type IIS restriction enzyme cleaving outside of its recognition site, than in step ba),
bc) ligation of the oligonucleotides from step ba) and bb) in the orientation defined by the blocking of the ends not to be ligated,
bd) Removing unused reactants as well as enzymes,
be) cleavage of the ligation product from step bc) with a type IIS restriction enzyme, which cleaves outside of its recognition site, whereby the cleavage occurs in the nucleic acid sequence of the oligonucleotide from step bb),
bf) separating the thus elongated nucleic acid molecule from the reaction mixture,
bg) optionally repeating steps bb) to be) at least one time, whereby subsequent to the last ligation in step bc) and removing unused reactants as well as enzymes the ligation product is cleaved with a type IIS restriction enzyme, whereby the cleavage occurs in the oligonucleotide from step ba),
c) ligation of the oligonucleotides from step a) and b) in the orientation defined by the blocking of the ends not to be ligated, d) removing unused reactants as well as enzymes,
e) cleavage of the ligation product from step c) with a type IIS restriction enzyme, which cleaves outside of its recognition site, whereby the cleavage occurs in the oligonucleotide from step a) or b),
f) separating the thus elongated nucleic acid molecule from the reaction mixture, characterized in that, in the last repetition of steps ab) to af), the oligonucleotide added in step ab) carries a modification, which allows coupling to a solid matrix.

In an eleventh aspect the problem is solved according to the invention by a method for the production of a nucleic acid molecule containing the steps of:
a) Providing an oligonucleotide, generated by the following steps:
aa) Providing an oligonucleotide, containing a recognition site for a type IIS restriction enzyme cutting outside of its recognition site,
ab) addition of a further, at least partially double-stranded oligonucleotide with a different recognition site for a type IIS restriction enzyme, cutting outside of its recognition site, than in step aa), and which carries a modification allowing coupling to a solid matrix,
ac) ligation of the oligonucleotides from step aa) and ab) in the orientation defined by the blocking of the ends not to be ligated,
ad) optionally removing and/or inactivating unused reactants as well as enzymes,
ae) cleavage of the ligation product from step ac) with a type IIS restriction enzyme, which cleaves outside of its recognition site, whereby the cleavage occurs in the nucleic acid sequence of the oligonucleotide from step ab),
af) separating the cleavage product from step ae) that does not carry a modification from the reaction mixture,
ag) optionally repeating steps ab) to af) at least one time,
b) providing a further oligonucleotide, generated by the steps:
ba) Providing an oligonucleotide, containing a recognition site for a type IIS restriction enzyme cutting outside of its recognition site,
coupling the oligonucleotide to the solid matrix,
bb) addition of a further, at least partially double-stranded oligonucleotide with a different recognition site for a type IIS restriction enzyme, cutting outside of its recognition site, than in step ba), and carrying a modification, which allows coupling to a solid matrix,
bc) ligation of the oligonucleotides from step ba) and bb) in the orientation defined by the blocking of the ends not to be ligated,
bd) optionally removing and/or inactivating unused reactants as well as enzymes,
be) cleavage of the ligation product from step bc) with a type IIS restriction enzyme, which cleaves outside of its recognition site, whereby the cleavage occurs in the nucleic acid sequence of the oligonucleotide from step bb),
bf) separating the cleavage product from step be) that does not carry a modification from the reaction mixture,
bg) optionally repeating steps bb) to bf) at least one time, whereby subsequent to the last ligation in step bc) and removing unused reactants as well as enzymes the ligation product is cleaved with a type IIS restriction enzyme, whereby the cleavage occurs in the oligonucleotide from step ba), c) ligation of the oligonucleotides from step a) and b) in the orientation defined by the blocking of the ends not to be ligated,
d) removing and/or inactivating unused reactants as well as enzymes,
e) cleavage of the ligation product from step c) with a type IIS restriction enzyme, which cleaves outside of its recognition site, whereby the cleavage occurs in the oligonucleotide from step a) or b),
f) separating the thus elongated nucleic acid molecule from the reaction mixture, In a twelfth aspect the problem is solved according to the invention by a method for the production of a nucleic acid molecule containing the steps of:
a) Providing an oligonucleotide, generated by the following steps:
aa) Providing an oligonucleotide, containing a recognition site for a type IIS restriction enzyme cutting outside of its recognition site, and carrying a modification, which allows coupling to a solid matrix,
coupling the oligonucleotide to the solid matrix,
ab) addition of a further, at least partially double-stranded oligonucleotide with a different recognition site for a type IIS restriction enzyme, cutting outside of its recognition site, than in step aa),
ac) ligation of the oligonucleotides from step aa) and ab) in the orientation defined by the blocking of the ends not to be ligated,
ad) removing unused reactants as well as enzymes,
ae) cleavage of the ligation product from step ac) with a type IIS restriction enzyme, which cleaves outside of its recognition site, whereby the cleavage occurs in the nucleic acid sequence of the oligonucleotide from step ab),
af) separating the cleavage product obtained in step ae) that does not carry a modification, from the reaction mixture,
ag) optionally repeating steps ab) to af) at least one time,
b) providing a further oligonucleotide, generated by the steps:
ba) Providing an oligonucleotide, containing a recognition site for a type IIS restriction enzyme cutting outside of its recognition site, and carrying a modification, which allows coupling to a solid matrix, with one end to a solid matrix,
coupling the oligonucleotide to the solid matrix,
bb) addition of a further, at least partially double-stranded oligonucleotide with a different recognition site for a type IIS restriction enzyme, cutting outside of its recognition site, than in step ba),
bc) ligation of the oligonucleotides from step ba) and bb) in the orientation defined by the blocking of the ends not to be ligated,
bd) removing unused reactants as well as enzymes,
be) cleavage of the ligation product from step bc) with a type IIS restriction enzyme, which cleaves outside of its recognition site, whereby the cleavage occurs in the nucleic acid sequence of the oligonucleotide from step bb),
bf) separating the thus elongated nucleic acid molecule from the reaction mixture,
bg) optionally repeating steps bb) to bf) at least one time, whereby subsequent to the last ligation in step bc) and removing unused reactants as well as enzymes the ligation product is cleaved with a type IIS restriction enzyme, whereby the cleavage occurs in the oligonucleotide from step ba), c) ligation of the oligonucleotides from step a) and b) in the orientation defined by the blocking of the ends not to be ligated, d) removing unused reactants as well as enzymes, e) cleavage of the ligation product from step c) with a type IIS restriction enzyme, which cleaves outside of its recognition site, whereby the cleavage occurs in the oligonucleotide from step a) or b), f) separation of the thus elongated nucleic acid molecule from the reaction mixture, whereby the oligonucleotide from step aa) and/or the oligonucleotide from step ab) carry at least one methylation, whereby after at least one repetition of steps aa) to af) at least a part of a recognition site of a type IIS restriction enzyme is formed in the oligonucleotide that is based on the oligonucleotide from step aa), and which recognition site is completed by ligation with a further oligonucleotide according to step ae), and which methylation prevents a cleavage of the thus generated ligation product using this recognition site and/or the oligonucleotide from step aa) and/or the oligonucleotide from step ab) carry at least one methylation, whereby after at least one repetition of steps aa) to af) at least a part of a recognition site of a type IIS restriction enzyme is formed in the oligonucleotide that is based on the oligonucleotide from step ab), and which recognition site is completed by ligation with a further oligonucleotide according to step ae), and which methylation prevents a cleavage of the thus generated ligation product using this recognition site and/or the oligonucleotide from step ba) and/or the oligonucleotide from step bb) carry at least one methylation, whereby after at least one repetition of steps ba) to bf) at least a part of a recognition site of a type IIS restriction enzyme is formed in the oligonucleotide that is based on the oligonucleotide from step ba), and which recognition site is completed by ligation with a further oligonucleotide according to step be), and which methylation prevents a cleavage of the thus generated ligation product using this recognition site and/or the oligonucleotide from step ba) and/or the oligonucleotide from step bb) carry at least one methylation, whereby after at least one repetition of steps ba) to bf) at least a part of a recognition site of a type IIS restriction enzyme is formed in the oligonucleotide that is based on the oligonucleotide from step bb), and which recognition site is completed by ligation with a further oligonucleotide according to step be), and which methylation prevents a cleavage of the thus generated ligation product using this recognition site.

In a thirteenth aspect the problem is solved according to the invention by a method for the amplification of a ligation product formed in the context of the Sloning method, whereby the procedure comprises the following steps:

a) Providing a ligation product;

b) providing a primer which is at least partially complementary to the oligonucleotide according to step aa) and/or ab) of the Sloning method, c) providing a primer which is at least partially complementary to the oligonucleotide according to step ab) and/or bb) of the Sloning method, d) hybridizing at least one of the primers with the ligation product;

e) performing a polymerase chain reaction by using the primer hybridized to the ligation product.

Additional embodiments of the various aspects of the present invention result from the sub-claims.

The present invention is based on the surprising realization that the sequence-independent assembly of any desired oligonucleotides and thus the synthesis of any desired nucleic acid which is possible with the procedure according to WO 00/75368, can be further improved, since the lower complexity of the oligonucleotide library (as it can be generated according to the procedure of the present application) allows for a higher standardization of the oligonucleotides contained therein. In particular, one can achieve a higher yield and a greater purity due to the possible shortening of the oligonucleotides according to the procedure at hand allows, whereby the accuracy of the gene synthesis can be further increased.

In the procedure according to WO 00/75368 two classes of oligonucleotides are used, whereby the two classes denoted as anchor- and splinker-oligonucleotides differ by the presence of two different recognition sites for type IIS restriction enzymes and the elements within one class of oligonucleotides differ in the sequence of the respective overhang. To be able to produce any genes according to this procedure there has to be a library of oligonucleotides available that contains all possible sequence variants of the oligonucleotides in question. According to the present invention the respective required anchor and splinker oligonucleotides can be produced by using a total of three standardized elements, if required, in a modification of the method described in the application WO 00/75368. The three elements are on the one hand two classes of oligonucleotides which basically differ in the presence of at least one recognition sequence (or the sequence complementary thereto) for a type IIS restriction enzyme, and a single-stranded oligonucleotide also denoted in the following as linker.

Type IIS restriction enzymes are characterized by the fact that they interact with two discrete sites of a double-stranded. One of the two sites is the recognition site which typically has a length of 4 to 7 nucleotides. The other site is the cleavage site, which is usually 1 to 20 base pairs away from the recognition site The recognition sites of the restriction enzymes are either completely or partially asymmetric.

The two classes of oligonucleotides containing each at least one recognition sequence for a type IIS restriction enzyme (or a sequence complementary thereto) preferably comprise the following structural elements in 3' to 5' direction: a single-stranded region, a double-stranded region and, optionally, a loop. This secondary structure is formed as a consequence of the primary structure of the respective single-stranded nucleic acid.

The single-stranded region insofar has a special importance in that it constitutes or contains either completely or partially the recognition site for a type IIS restriction enzyme. Alternatively the single-stranded region may also comprise a sequence complementary to the complete recognition site for a type IIS restriction enzyme or a part thereof. The minimal length of the single-stranded region can thereby be a single nucleotide. The maximum length of this region is principally not restricted, but it is preferred when it does not contain additional nucleotides other than the recognition sequence, since the length of the oligonucleotide is needlessly elongated, which is associated with increased synthesis cost and a higher risk of abortive sequences. On the other hand the overhang used should allow for a stable hybridization with the single-stranded linker. Thus 3-7 nucleotides are considered to be optimal.

The double-stranded region can be generated by (re-) folding of the oligonucleotide on itself. The length of the double-stranded region is preferentially three to nine nucleotides. In principle, the specific order of the nucleotides in this region is arbitrary, as long as, at least under the conditions of the nucleic acid synthesis during which the oligonucleotide is to be used, a stable hybridization occurs between the complementary nucleotides of the oligonucleotide. Thereby the formation of GC-pairs is preferred due to the increased stability of a GC-pairing compared to an AT-pairing. When type IIS restriction enzymes with more distant restriction site are used, the recognition sites for these enzymes can be completely as well as partially contained in the double-stranded region.

The loop of the oligonucleotide can be formed from an arbitrary sequence of nucleotides. However, when choosing the sequence care has to be taken that no interaction occurs with other sequences thus disturbing the formation of the loop or the other (secondary-) structures forming the oligonucleotide. Preferably one uses pyrimidines and especially thymidines, since they are relatively small and the arising loop structure is stable. Cytosine forms a more stable base pair with guanosine, whereby the formation of alternative secondary structures is favored. The use of preferably four pyrimidines and preferentially thymidines results from the fact that the ring tension is too high with less than 4 nucleotides (whereby the adjacent double-stranded region could be broken up). More than 4 nucleotides, however, have no impact on the loop tension and thus would be superfluous.

The above described class of oligonucleotides is herein denoted as one-piece or self complementary oligonucleotide. An alternative class of oligonucleotides, which however has the same function, especially in the context of its use in gene- or nucleic acid synthesis, is characterized by the fact that the loop is not present. This class of oligonucleotides can be produced by hybridization of two single-stranded oligonucleotides with each other, whereby the double-stranded and single-stranded region are generated. Due to the absence of the loop one has to consider several aspects when choosing and designing the two single-stranded oligonucleotides to be hybridized, both in terms of their sequence as well as the modifications on the 3' and 5' end and to take suitable measures, respectively. As will be explained in the following, it has to be guaranteed with this type of two-piece oligonucleotide that there is no false pairing with the linker. Further on it has to be guaranteed the due to the absence of the loop the exposed ends of the two hybridized single strands are not a substrate for a polymerase or a ligase. This can be accomplished by a coupling an amino linker, a succinylester, a fluorescent dye or a digoxygenin residue to the terminal 5' or 3' phosphate groups, respectively.

Both alternatives of oligonucleotide classes, i.e. the self complementary form as well as the two-piece form of oligonucleotides can possess a modification which allows for a coupling to a solid phase. In the case of the self-complementary form this modification preferentially occurs in the loop region. With this modification it is guaranteed that the oligonucleotide or a nucleic acid containing it can be separated from other components. The modification itself can result from measures known to experts in the field. Exemplary modifications are the incorporation of low molecular weight compounds like biotin, digoxygenin, fluorescein isothiocyanate (FITC), amino compounds or succinyl esters. The surface will hence contain molecules which allow for a generally specific interaction with the modification for the purpose of immobilization.

The linker as the third standardized element is chemically also an oligonucleotide. The linker consists basically out of two sequence moieties. The first (constant) sequence moiety, herein also denoted as part A, contains at least the recognition site of a type IIS restriction enzyme or a part thereof. Alternatively, part A can comprise the sequence complementary to the recognition site of the type IIS restriction enzyme or a part thereof. The second (variable) moiety of the linker, herein also denoted as part B, is an arbitrary but defined sequence of nucleotides. The specific design of the constant part A of the linker is dependent on the particular type IIS restriction enzymes, which are used in the context of the synthesis or to which the two classes of oligonucleotides are geared to, respectively (this is generally completely complementary to the single-stranded portion of at least one of the oligonucleotides described above).

In the following the design of an oligonucleotide and the respective linker is demonstrated under the assumption that the single-stranded portion of the oligonucleotide contains the complete recognition site of a type IIS restriction enzyme. Due to the property of these restriction enzymes, that the cleavage site is outside of the recognition site, i.e. the recognition site is not destroyed by the enzymatic activity, and that the cleavage of the restriction enzyme occurs at a defined distance from the recognition site irrespective of the sequence to be cleaved, the linker can be designed such that the constant part A is complementary to the recognition sequence of the restriction enzyme, which sequence constitutes the single-stranded region of the oligonucleotide. Due to this complementarity a hybridization of oligonucleotide and linker can occur. Since the linker contains, in addition to part A, also a part B, part B forms, after hybridization with the oligonucleotide, an overhang or a protruding end. The same structure of oligonucleotide and linker is generated when the oligonucleotide contains a sequence in its single-stranded portion which is complementary to the recognition sequence of the restriction enzyme and part A of the linker constitutes the recognition site of the restriction enzyme. In this context, it is not required that either the single-stranded portion of the oligonucleotide or the constant part A of the linker comprise the complete recognition site or its complementary sequence respectively. In fact it is also within the scope of the invention when the recognition sequence of the restriction enzyme or the sequence complementary thereto is collectively generated by segments of the double-stranded region and the single-stranded region. In this case part A of the linker will for example contain only the part of the recognition sequence of the restriction enzyme which is complementary to the part contained in single-stranded region of the oligonucleotide.

The length of part B of the linker is determined by the respective restriction enzyme and more precisely by the length of the overhang produced by it. The following table 1 gives an overview over the different type IIS restriction enzymes, their recognition sequences and the overhangs produced. Thereby the table depicts pairs of restriction enzyme which, according to the inventive procedure for nucleic acid synthesis, are preferentially used in combination with the standardized elements.

TABLE 1

Exemplary design of oligonucleotide 1 and oligonucleotide 2 as well as the linker according to the invention depending on the particular pair of type IIS restriction enzymes.

| Restriction enzyme pair | Oligonucleotide 1 (5'-3') | Oligonucleotide 2 (5'-3') | Linker (5'-3') |
|---|---|---|---|
| Eco31I/Esp3I | CGN$_{1-9}$X$_{1-9}$N'$_{1-9}$*CGTCTCN* (SEQ ID NO: 14) | CCN$_{1-9}$X$_{1-9}$N'$_{1-9}$*GGTCTCN* (SEQ ID NO: 16) | NNNNN'GAGA (SEQ ID NO: 18) |
| BbsI/Acc36I | TTCN$_{1-9}$X$_{1-9}$N'$_{1-9}$*GAAGACNN* (SEQ ID NO: 15) | CAGGTN$_{1-9}$X$_{1-9}$N'$_{1-9}$*ACCTGCN$_4$* (SEQ ID NO: 17) | a) NNNNN'$_2$GTC (SEQ ID NO: 19) b) NNNNN'$_4$G (SEQ ID NO: 20) |
| Eco31I/Esp3I (bipartite) | N$_{1-9}$CGTCTCN (SEQ ID NO: 21) CGN'$_{1-9}$ (SEQ ID NO: 22) | CCN'$_{1-9}$ (SEQ ID NO: 23) N$_{1-9}$GGTCTCN (SEQ ID NO: 24) | N$_{1-9}$CGAGA (SEQ ID NO: 25) |
| BbsI/Acc36I (bipartite) | N$_{1-9}$GAAGACNN (SEQ ID NO: 26) TTCN$_{1-9}$ (SEQ ID NO: 27) | CAGGTN$_{1-9}$ (SEQ ID NO: 28) N'$_{1-9}$ACCTGCNNNN (SEQ ID NO: 29) | NNNNNNGTC (SEQ ID NO: 30) NNNNN'$_4$G (SEQ ID NO: 31) |

Where:
N any of the nucleotides A, G, C or T;
N' the complementary nucleotide of N in the corresponding position of the complementary strand
X any nucleotide or non-nucleotide element (if necessary with a respective modification) which is capable to form a chain.
The subscripts indicate the number of the respective elements.

TABLE 2

Exemplary combinations of recognition sites of type IIS restriction enzymes in the oligonucleotides of class 1 and 2

| recognition sequence of class 1 | recognition sequence of class 2 |
|---|---|
| CGTCTCN^NNNN_ (Esp3I, BsmBI) (SEQ ID NO: 1) | GGTCTCN^NNNN_ (BsaI, Eco31I, . . . ) (SEQ ID NO: 2) |
| GGTCTCN^NNNN_ (BsaI, Eco31I, . . . ) (SEQ ID NO: 2) | CGTCTCN^NNNN_ (Esp3I, BsmBI) (SEQ ID NO: 1) |
| GAAGACNN^NNNN_ (BbsI, BpiI . . . ) (SEQ ID NO: 3) | ACCTGCNNNN^NNNN_ (BspMI, Acc36I) (SEQ ID NO: 4) |
| ACCTGCNNNN^NNNN_ (BspMI, Acc36I) (SEQ ID NO: 4) | GAAGACNN^NNNN_ (BbsI, BpiI . . . ) (SEQ ID NO: 3) |
| GCAGTG_NN^ (BtsI) (SEQ ID NO: 5) | GCAATG_NN^ (BsrDI, Bse3DI, . . . ) (SEQ ID NO: 6) |
| GCAATG_NN^ (BsrDI, Bse3DI, . . . ) (SEQ ID NO: 6) | GCAGTG_NN^ (BtsI) (SEQ ID NO: 5) |
| GTATCCNNNNN_N^ (BciVI, BfuI) (SEQ ID NO: 7) | ACTGGGNNNN_N^ (BfiI, BmrI) (SEQ ID NO: 8) |
| ACTGGGNNNN_N^ (BfiI, BmrI) (SEQ ID NO: 8) | GTATCCNNNNN_N^ (BciVI, BfuI) (SEQ ID NO: 9) |
| GGCGGANNNNNNNNN_NN^ (EciI) (SEQ ID NO: 9) | GAGGAGNNNNNNNN_NN^ (BseRI) (SEQ ID NO: 10) |
| GAGGAGNNNNNNNN_NN^ (BseRI) (SEQ ID NO: 10) | GGCGGANNNNNNNNN_NN^ (EciI) (SEQ ID NO: 9) |
| CACCTGCNNNN^NNNN_ (AarI) (SEQ ID NO: 11) | CAGCTCNNNNNNN^NNNN_ (AceIII) (SEQ ID NO: 12) |
| CAGCTCNNNNNNN^NNNN_ (AceIII) (SEQ ID NO: 12) | CACCTGCNNNN^NNNN_ (AarI) (SEQ ID NO: 11) |
| GCTCTTCN^NNN_ (SapI) (SEQ ID NO: 13) | (Adapter Linker required) |

Where:
N any of the nucleotides A, G, C or T;
^ the cleavage site in the "above" strand, i.e. 5'-> 3' from left to right
_ the cleavage site in the "lower" strand, i.e. 5'-> 3' from right to left Preferred pairs of a first and a second type IIS restriction enzyme for use of the two classes of oligonucleotides and the linker molecule for the synthesis of a nucleic acid, preferentially a DNA, are the following: Eco31I/Esp3I (37° C.), BsaI/BsmBI (50° C.), BsmBI/BsaI (55° C.), BbsI/BspMI (37° C.), BspMI/BbsI (37° C.) BsrDI/BtsI (65° C.), BtsI/BsrDI (37° C.), BciVI/BmrI (37° C.), AarI/AceIII (37° C.), EciI/BseRI (37° C.) and BmrI/BciVI (37° C.). (The temperatures in brackets are the incubation temperatures used for the respective pair). The isochizomeres of these enzymes (BsaI: Bso31, Eco31I; BsmBI: Esp3I; BbsI: BpiI.BpuAI; BspMI: Acc36I; BsrDI:Bse3DI, BseMI; BmrI: BfiI) are potential replacements; in part these are overexpressed in cloned vectors and produced in higher yield or purity. Isochizomeres are also preferentially used when the shelf life of one enzyme compared to its isoschizomer is limited.

For example if BsaI is used as a restriction enzyme, an overhang of four nucleotides is produced which can have any given sequence. Since at any of the four nucleotide positions there can be any one of the four nucleotides (A, G, C, T), it is possible to produce with a total of 256 linker molecules any given sequence composed of four nucleotides. Such a linker can then be hybridized with an oligonucleotide due to the complementarity of the sequences of part A of the linker with the single-stranded portion of the oligonucleotide. If the overhang produced by the restriction enzyme contains two nucleotides the corresponding library will contain 16 elements, in case of an overhang of three nucleotides 64 elements, in case of an overhang of five nucleotides 1024 elements, in case of an overhang of six nucleotides 4096 elements and in case of an overhang of seven nucleotides 16384 elements.

For such libraries it is noteworthy that part B seems to contain an arbitrary sequence if one looks at a single linker, however in their entirety the linkers of a respective library cover the whole sequence spectrum which is defined by the length of the overhang and contains in each case a defined i.e. non random sequence of nucleotides.

The above concept of pairing an oligonucleotide of class 1, herein also denoted as first oligonucleotide and a respective linker, defined by a specific restriction enzyme, whereby the restriction enzyme defining the class of the oligonucleotide is the same as the type IIS restriction enzyme defining the class of the linker, can be applied in the same manner to the pair of linker and oligonucleotide of a second class defined by another, second type IIS restriction enzyme to form complexes of linker and oligomer. Since a different type IIS restriction enzyme is used in this case, part A of the linker will be different from the linker described above in connection with the first type IIS restriction enzyme. Part B however, will be formed, again depending on the length of the end produced by the type IIS restriction enzyme and collectively define a respective sequence spectrum.

Based on the above described procedure there are typically two linker libraries, which, due to specificity or complementarity, respectively of the recognition site of the respective type IIS restriction enzyme can hybridize with one corresponding oligonucleotide each. Following hybridization and if applicable ligation of the linker with the oligonucleotide, the linker is typically phosphorylated and the overhang generated by part B of the linker filled in by a polymerase such that the complex containing the oligonucleotide and the linker is present as a blunt ended oligonucleotide. This procedure is repeated for the oligonucleotide of the second class and the corresponding linker (of the second class). Subsequently the two blunt ended oligonucleotides which are elongated by the linker are ligated to one another and subsequently digested with one of the two type IIS restriction enzymes. Hence one or the other oligonucleotide will be elongated. The number of nucleotides added is thereby defined by the length of the overhang, which is produced by the respective enzyme that is used for the digestion of the two ligated blunt ended oligonucleotides.

The directed assembly of a defined nucleic acid is possible by using and repeating the above describe schematic reactions, because those linkers are chosen from the linker-library that contain as part B the sequence which is to be added to an existing or to be assembled nucleic acid. After the digestion of the ligation product of the two blunt ended oligonucleotides one obtains a cleaved off oligonucleotide which can be used for gene synthesis according to the Sloning procedure, as is subject of the international patent application WO 00/75368. In this procedure larger genes are produced such that first subfragments are produced by sequential ligations of unmodified double-stranded oligonucleotides (so-called splinkers) in parallel reactions are build upon oligonucleotides (so-called anchors) which can be immobilized via a modification. The thus arising ligation products are digested after every step with the restriction enzyme the recognition sequence of which is contained in the splinker molecules which have been ligated. Thereby only the variable part of the splinker is retained on the anchor molecule whereas the constant part is cleaved by the restriction enzyme and removed from the reaction mixture by a washing step. Depending upon the sub-sequence to be synthesized, the splinker required for each single step is selected from the library of all splinker molecules. Subsequently one half of the fragments obtained in this way is treated with the anchor specific restriction enzyme, the other half of the fragments with the splinker specific enzyme. Each of the fragments now has a single-stranded overhang which is complementary to the overhang of the next fragment in the sequence of the gene to be synthesized. By ligating the adjacent fragments (so-called transposition) the length of the now present fragments is doubled, while the number is cut in half. With each further transposition the length of the sub-fragments is doubled, until finally only one fragment is left which normally contains the complete gene sequence to be synthesized.

Expressed in its generality, the procedure, herein also commonly denoted as Sloning procedure, comprises the following steps:

a) Providing an oligonucleotide, generated by the following steps:

aa) Coupling of an oligonucleotide with one end to a solid matrix, whereby the coupling occurs via a modification, and the oligonucleotide comprises a recognition site for a type IIS restriction enzyme, which cleaves outside of its recognition site, ab) Addition of another at least partially double-stranded oligonucleotide with another recognition site for a type IIS restriction enzyme, cleaving outside of its recognition site than in step aa), whereby this oligonucleotide cannot bind to the matrix, ac) Ligation of the oligonucleotides from step aa) and ab) in the orientation defined by the blocking of the ends not to be ligated, ad) Removal of unused reactants as well as enzymes, ae) Cleavage of the ligation product from step ac) with a type IIS restriction enzyme, which cleaves outside of its recognition site, whereby the cleavage occurs in the nucleic acid sequence of the oligonucleotide from step ab), af) Separation of the reaction mixture from the elongated oligonucleotide obtained in step ae), first provided in step aa), ag) at least one repetition of steps ab) to af), b) Providing a further oligonucleotide, generated by the steps:

ba) Coupling of an oligonucleotide with one end to a solid matrix, whereby the coupling occurs via a modification, and the oligonucleotide comprises a recognition site for a type IIS restriction enzyme, which cleaves outside of its recognition site, bb) Addition of another at least partially double-stranded oligonucleotide with another recognition site for a type IIS restriction enzyme, cleaving outside of its recognition site than in step ba), whereby this oligonucleotide cannot bind to the matrix bc) Ligation of the oligonucleotides from step ba) and bb) in the orientation defined by the blocking of the ends not to be ligated, bd) Removal of unused reactants as well as enzymes, be) Cleavage of the ligation product from step bc) with a type IIS restriction enzyme, which cleaves outside of its recognition site, whereby the cleavage occurs in the nucleic acid sequence of the oligonucleotide from step bb), bf) Separation of the thus elongated nucleic acid molecule from the reaction mixture bg) at least one repetition of steps bb) to bf), whereby subsequent to the last ligation in step bc) and removal of unused reactants as well as enzymes the ligation product is cleaved with a type IIS restriction enzyme, whereby the cleavage occurs in the oligonucleotide from step ba), c) Ligation of the oligonucleotides from step a) and b) in the orientation defined by the blocking of the ends not to be ligated, d) Removal of unused reactants as well as enzymes, e) Cleavage of the ligation product from step c) with a type IIS restriction enzyme, which cleaves outside of its recognition site, whereby the cleavage occurs in the oligonucleotide from step a) or b), f) Separation of the thus elongated nucleic acid molecule from the reaction mixture, The term solid phase as it is used herein refers to any surface onto which a coupling of at least one reactant is possible. Among these are, in particular, surface forms like filters, foils, membranes, chips, plates, beads and columns. These surface forms can be produced from any of the following materials: Polymers such as plastic, for example polystyrene, polyacetate, poly-acrylamide, polyvinylidenfluorid, agarose, sepharose, cellulose; silicon, glass (silicon glass) and silica gel. These materials can be modified in one or several ways known to the expert.

The coupling can be achieved on the side of the oligonucleotide in that a modification is present internally, i.e. on a non terminal nucleotide of the polynucleotide, or terminally, i.e. on a terminal nucleotide. The latter is especially possible when the oligonucleotide has a bipartite structure. Such modifications which allow for a coupling to a surface, in particular to a modified surface, are known to the experts in the field and comprise for example biotin, iminobiotin, digoxygenin, sulfhydryl groups, dichyohexylcarbodiimide, fluoresceine, acrydine and rhodamine.

The coupling on the side of the solid phase can occur by one or several of the following modifications: Avidine, like streptavidine, monomeric avidine, avidine modified in tyrosine residues; antibodies, in particular those directed against the above compounds, and suflhydryl groups.

It is within the scope of the skills of the experts in the field to determine appropriate combinations of the above modifications of the reaction partners.

In a further development of the procedure according to WO 00/75368 it is also possible to produce several gene variants simultaneously. In order to be able to produce sub-fragments with terminally different sequences, the following modification of the protocol is necessary: Following ligation of a modified splinker to an elongated anchor (after previous blocking of the existing binding sites on the solid phase) the obtained anchor-splinker ligation product is not cleaved with the with the splinker specific restriction enzyme, but with the anchor specific restriction enzyme. In this way double-stranded molecules are formed which contain on one end a single-stranded overhang but despite their modification are not bound any more to the solid phase. These molecules can now be divided into different reaction vessels and bound to a solid phase. Following a new blockage of free binding sites, ligation of new anchor molecules as well as cleavage with the splinker specific restriction enzyme, it is now possible to ligate different splinkers, which differ in their overhang sequence but not in the nucleotides directly adjacent to the overhang, which after the following restriction form the next overhang. Thus several different sub-fragments can be assembled. These fragments are ligated in the next step with splinkers, which again carry the same sequence adjacent to the overhang such that all variant fragments can, after the following cleavage, be joined with the fragment which follows in order in the gene sequence to be synthesized. To obtain a nearly equimolar distribution of these different fragments all other ligation products produced in parallel have to be similarly treated and aliquoted. For this it is necessary that those fragments, which according to the original procedure remain on the anchor have to be first ligated with an anchor molecule, after they have been cleaved with the anchor-specific restriction endonuclease in order to continue the reaction. This aspect of the invention is illustrated in the FIGS. 9 to 14.

If needed the last transposition can be followed by a polymerase chain reaction (PCR) in which oligonucleotides are used as primers which are complementary to the constant regions of anchor and splinker. In this way losses, which stem from the distribution of the reactions can be compensated. Preferentially thermostable polymerases with proofreading function are employed to minimize the introduction of additional errors.

A similar procedure can be used in order to prevent shortened ligation products, which may be produced by incomplete cleavages with the splinker-specific restriction endonuclease, from getting into the following transposition reaction (=Transfer of elongated splinker molecules after cleavage with the anchor-specific restriction endonuclease) and thus leading to deletion mutants. Hereby anchor molecules are ligated instead of splinker molecules at the end of the last ligation/restriction cycle, which however contain a recognition sequence for the splinker-specific restriction enzyme (so called splinker-anchor).

By blocking any remaining free binding sites on the solid phase it is guaranteed that the splinker-anchors can only be coupled to the solid phase via ligation to the elongated anchors. Following cleavage of the thus created ligation products with the anchor-specific restriction enzyme only those molecules, which obtained a modified splinker-anchor in the last step, carry the corresponding modification and can thus be separated from unmodified sub-fragments by binding to a solid phase in a next step after transfer into a new reaction vessel. This aspect of the invention is further illustrated in FIGS. 15 to 17.

In addition, it is also possible to revert the procedure described in application WO 00/75368: instead of synthesizing the gene fragments on anchor oligonucleotides coupled to a solid phase, the ligations can in principle also occur in solution, whereby modified splinker-anchors instead of splinker oligonucleotides are ligated. Following cleavage with the splinker-specific restriction endonuclease the uncut ligation products remain at the solid phase whereas the fragments released by the restriction can be transferred into new reaction mixtures. Preferably enzymes can be used in this procedure which themselves carry a modification and thus are also retained in the reaction mixture. A heat denaturation of the enzymes is thus not necessary anymore. This aspect of the invention is described in detail in FIGS. 18 to 20.

In principle, by combining the procedures described in the last two paragraphs, it is possible to transfer the synthesized sub-fragments at will between anchor and splinker-anchor back and forth (Transfer-Reaction). Given an identical overhang sequence it is possible to combine any gene fragment from different synthesis reactions with one another. This "mini-exon-shuffling" is ideally suited for the production of designer proteins or for the optimization of enzymatic properties by combining mutants with increased activity and stability respectively.

The gene synthesis procedure described in application WO 00/75368 was limited in the choice of the nucleic acids to be synthesized insofar as the recognition sites of the used anchor- and splinker-specific type IIS restriction enzymes were not allowed to be present in the sequence to be synthesized because this would lead to internal cleavages of the partial fragments. This limitation can be circumvented by using a splinker with a recognition sequence for an alternative restriction endonuclease for the assembly of such a sequence and treating the ligation product subsequently with the respective methylase. The methylated internal sequences are then protected from cleavage with the respective restriction endonuclease whereas the anchors and splinkers can still be separated. This aspect of the invention is further illustrated in FIGS. 21 to 22.

Finally an improvement of the procedure of the original application can be achieved by the fact that the use of splinker oligonucleotides with an overhang only three nucleotides in length is possible although so far no pair of restriction endonucleases is known that produce a three nucleotide overhang and have in addition recognition sequences, which can be discriminated. The problem that the gene fragments cannot be assembled either on one end or the other in the transpositions can be circumvented by the fact that last splinker to be added is an adapter, i.e. which has a three nucleotide protruding end but contains a recognition sequence for a restriction enzyme generating a four nucleotide overhang. The use of such splinker-adapters is of advantage insofar as only a splinker library of smaller complexity is necessary (4096 instead of 65536) and that three nucleotide overhangs can never be self-complementary. Since furthermore genes can be assembled in the triplet raster, a further decrease of complexity is possible for coding regions because splinkers need not be supplied for all codons. Altogether 256 different splinker-adapters are required to cover a 11 sequence variants; if one confines oneself to the 30 most frequent codons, 120 would be sufficient. This aspect of the invention is further illustrated in FIGS. 2 to 8.

The main aspect of the present invention relies on the fact that it is possible, with the help of the procedures described herein, to significantly reduce the size of the oligonucleotide library necessary for the synthesis of any desired genes by a combinatorial production from two smaller libraries. This kind of procedure yields further significant advantages compared to the already very advantageous Sloning procedure, as it does not use standardized elements with a length of 30 to 40 nucleotides but rather linker molecules, which typically have a length of 6 to 11 nucleotides. Thereby the degree of purity of the standardized oligonucleotide building blocks can be extremely improved and a basis is formed for a very reliable nucleic acid synthesis, which can be automated.

Another advantage of the inventive procedure as shown by the above description is that the size of a linker library is only 256 in case of a four nucleotide overhang, whereby this library must correspondingly be produced for each type IIS restriction enzyme that used with the oligonucleotides. Thus it follows that in the above mentioned example a total of only 512 different linkers and two oligonucleotides (one for each class) must be produced compared to a total of 65536 oligonucleotides (when using restriction enzymes generating an overhang of four nucleotides in relation to their recognition sequence.

A particularly preferred embodiment both with respect to the linkers and to the libraries resulting thereof can be realized if, such as in the case of the restriction enzyme pair Eco31I/Esp3I, the recognition sequence differs only in one nucleotide. Under these circumstances it is possible that instead of 512 different elements (256 linkers for class 1 and 256 linkers for class 2) only 256 different linkers must be produced when the one nucleotide, in which the two restriction enzymes of the restriction enzyme pair differ, is arranged not in part A of the linker but rather in the terminal part of the double-stranded region of the oligonucleotide.

In the following table 2 sequences for represents of both classes of oligonucleotides are shown as well as the corresponding type IIS restriction enzyme, the recognition site of which is either completely or partially present in the 3' OH overhang

TABLE 3

Sequence examples for self-complementary and bi-partite oligonucleotides

| Restriction-<br>enzyme pair | Oligonucleotide 1<br>(5'-3') | Oligonucleotide 2<br>(5'-3') | Linker<br>(5'-3') |
|---|---|---|---|
| Eco31I/Esp3I | CGCCCCTTTTGGGGCGTCTCG<br>(SEQ. ID. No. 9) | CCCGGGTTTTCCCGGGTCTCG<br>(SEQ. ID. No. 11) | NNNNCGAGA<br>(SEQ. ID. No. 13) |
| BbsI/Acc36I | TTCGGGTTTTCCCGAAGACGC<br>(SEQ. ID. No. 10) | CAGGTGGGTTTTCCCACTGGGACGC<br>(SEQ. ID. No. 12) | NNNNGCGTC<br>(SEQ. ID. No. 14) |
| Eco31I/Esp3I<br>(bipartite) | GGGGCGTCTCG<br>CGCCCC<br>(SEQ. ID. No. 17) | CCCGGG<br>CCCGGGTCTCG<br>(SEQ. ID. No. 19) | NNNNCGAGA<br>(SEQ. ID. No. 15) |
| BbsI/Acc36I<br>(bipartite) | CCCGAAGACGC<br>TTCGGG<br>(SEQ. ID. No. 18) | CAGGTG<br>CCCACTGGGACGC<br>(SEQ. ID. No. 20) | NNNNGCGTC<br>(SEQ. ID. No. 16) |

The nucleic acid libraries disclosed herein consist of a plurality of the inventive nucleic acid molecules as disclosed herein. The term "single-stranded nucleic acid molecule" and "linker" are used synonymously unless otherwise indicated. Preferably these nucleic acid libraries comprise the complete range of sequences as defined by the length of the overhang (part B of the linker). However, it is also within the scope of the present invention that solely a part of the corresponding linkers and thus only a part of the range of sequences is contained in the nucleic acid molecule library. In addition, the relative proportion of the individual molecules in such a library can either be equimolar or unequal. It is for example within the scope of the present invention that such sequences that are occur comparatively rarely in the sequences to be synthesized or in natural sequences, are underrepresented compared to other sequences that occur more frequently.

As already disclosed in the above description both the single-stranded nucleic acid molecules, i.e. the linkers and the nucleic acid molecule libraries can be used in the context of a procedure for the production of a nucleic acid molecule. Preferably this procedure concerns a procedure with sequential ligation of oligonucleotides in a sequence-independent manner as described in the international patent application WO 00/75368 by way of example. The oligonucleotides defined herein as oligonucleotides of the first class, whereby the classification is made in such a way that an oligonucleotide of the first class comprises a recognition site of a first type IIS restriction enzyme or a part thereof or a sequence complementary thereto, and an oligonucleotide of the second class comprises the recognition sequence or a part thereof or a sequence complementary thereto of a second type IIS restriction enzyme, which is different from the first restriction enzyme, can b e a so-called "anchor" oligonucleotide, i.e. which carries a modification allowing an immobilization of the oligonucleotide on a solid phase, and the other class can be a so-called "splinker" oligonucleotide, which has an identical or a different cleavable modification. Otherwise "anchor" and "splinker" oligonucleotides are in accordance with the design for oligonucleotides described herein consisting of a single-stranded and a double-stranded region as well as optionally a loop.

In this context the inventive procedure allows for providing an oligonucleotide of a class 1 defined by the presence of a recognition site, a part thereof or a sequence complementary thereto for a first type IIS restriction enzyme, whereby this oligonucleotide can be designed, with respect to the recognition site for the first type IIS restriction enzyme, as disclosed above. This oligonucleotide referred to in the following as first oligonucleotide can have a modification, which allows an attachment or immobilization of the first oligonucleotide to a surface, preferably a solid matrix. Preferably this modification is designed in such a way as to allow the cleavage of the oligonucleotide bound to the surface. To this first oligonucleotide an inventive linker is added under suitable conditions so that hybridization occurs between the first oligonucleotide and the linker. The hybridization is based on the complementarity of part A of the linker with the single-stranded portion of the oligonucleotide. Through hybridization a double-strand is formed, which contains the complete recognition site of said type IIS restriction enzyme. The mass proportions between the first oligonucleotide and the linker are designed according to the requirements of an efficient ligation, whereby it is typically envisioned that the comparatively smaller linker is added in excess to the first oligonucleotide.

As a next step the 5' protruding portion of the first oligonucleotide can be filled in and thus made blunt ended after treatment with a kinase. Preferably the linker excess is removed before the filling in, which typically done with the Klenow fragment of the T4 polymerase. In case the first oligonucleotide is immobilized to a solid matrix, this can be done by using corresponding wash steps. Alternatively, in the case that the first oligonucleotide is not immobilized, it can be intended that a separation of the various molecules and particularly the separation of the linker are achieved with suitable separation techniques as for instance gel electrophoresis or gel filtration. Beside the removal of non-ligated excess of linkers, which is preferably carried out, the other components of the reaction mixture, i.e. kinase, Klenow fragment and the nucleoside triphosphates, which remained unreacted during the filling in, are removed either in parallel or in separate steps.

Parallel or subsequent to this, an oligonucleotide of the second class is provided, herein also referred to as second oligonucleotide, whereby this oligonucleotide or this class is thereby characterized that they, either completely or partially, comprise the recognition site of a type IIS restriction enzyme or the sequence complementary thereto, which is different from class 1, and that this oligonucleotide is now reacted with a respective linker, part A of which is complementary to the single-stranded region of the oligonucleotide, and that after ligation and filling in the end a blunt ended oligonucleotide is present. Also the second oligonucleotide, now tagged with a linker and filled in correspondingly, can be immobilized on a surface.

In a next step the blunt ended oligonucleotides are contacted with each other, whereby the first oligonucleotide or the second oligonucleotide is preferably immobilized on a surface. However, it is also within the scope of the inventive procedure that both blunt ended oligonucleotides are in solution. The two blunt ended oligonucleotides, which are elongated at their 5' ends with respect to their respective starting oligonucleotides by the respective length of the linker overhang, are ligated using a ligase activity. The unreacted molecules as well as the enzymes used can be readily removed by procedures known to those skilled in the art, as for example by electrophoresis, in the case that the complete reaction was carried out in solution, or by washing using suitable wash solutions in the case that one of the oligonucleotides and thus also the ligation product are immobilized on a surface.

In a next step an oligonucleotide is separated from the ligation product between the two blunt ended, filled in starting oligonucleotides by using one of the two type IIS restriction enzymes. This molecule differs from the originally employed oligonucleotide by the fact that it contains the variable nucleotides (part B) of the previously ligated linker as well as the variable nucleotides of the second linker, which was connected with the second oligonucleotide.

In the embodiment of the inventive procedure, in which at least one of the oligonucleotides is immobilized to a solid phase, a further step is inserted before the cleavage step by the type IIS restriction enzyme, in which the ligation product generated by the blunt ended, filled in first oligonucleotide and the blunt ended, filled in second oligonucleotide is detached from the surface by cleavage of the bond between the ligation product and the solid surface formed by the modification present in the oligonucleotide.

The kit according to the invention comprises at least one of the inventive single-stranded nucleic acid molecules, i.e. linkers. Preferably such a kit comprises one of the nucleic acid libraries according to the invention or a part thereof. In one embodiment the kit also comprises suitable buffers, enzyme activities such as ligases, topoisomerases, 3'→5' exonucleases, phosphatases, type IIS restriction enzymes or suitable surfaces. Preferably the kit comprises two different type IIS restriction enzymes, which preferably generate overhangs of the same length. It can be intended in this context that the surfaces already contain one or more of the standardized oligonucleotides.

Such a kit typically serves for the production of a nucleic acid.

The term "nucleic acid" herein preferably comprises deoxyribonucleic acid

Figure 4:
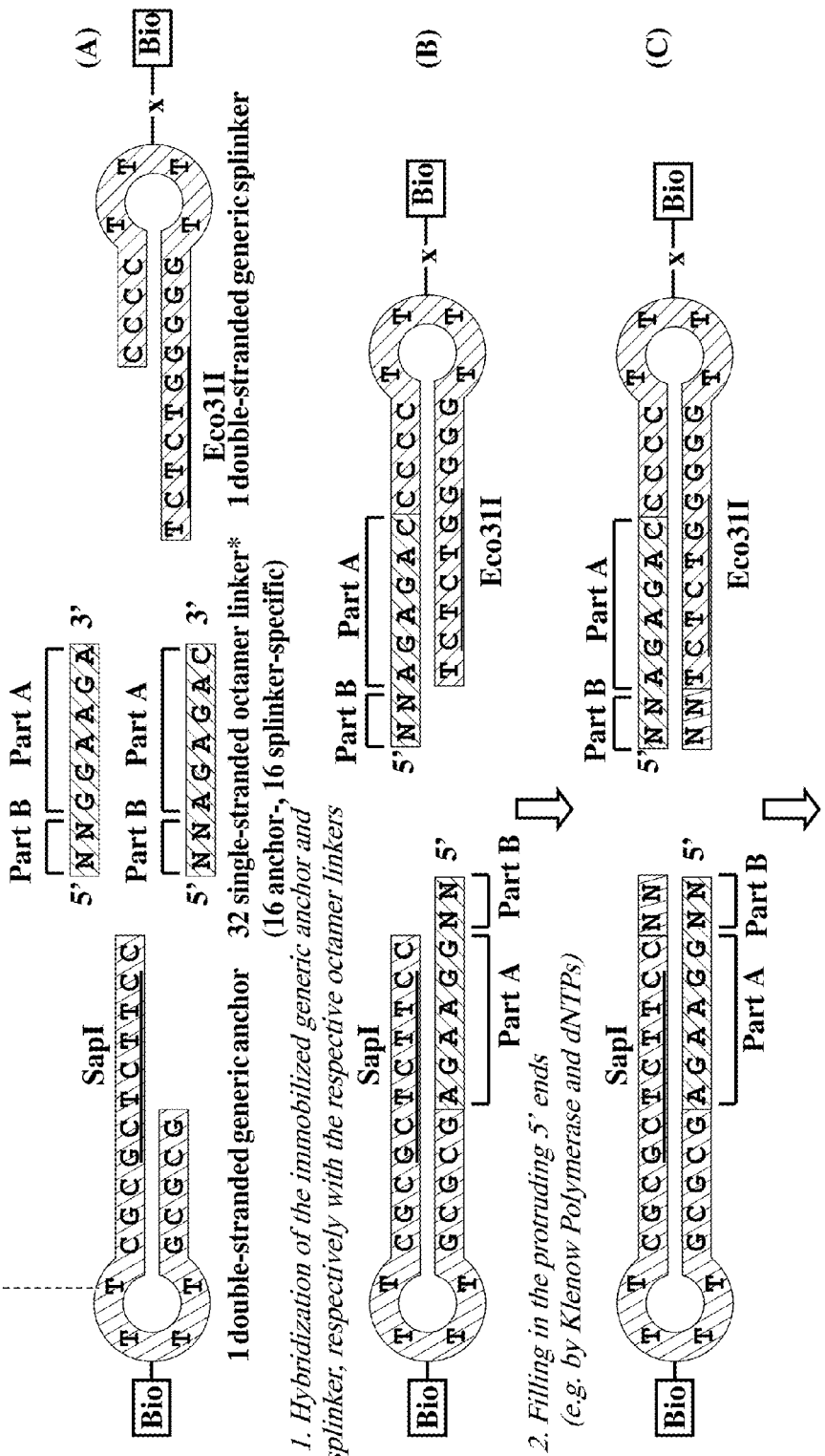
Figure 5:
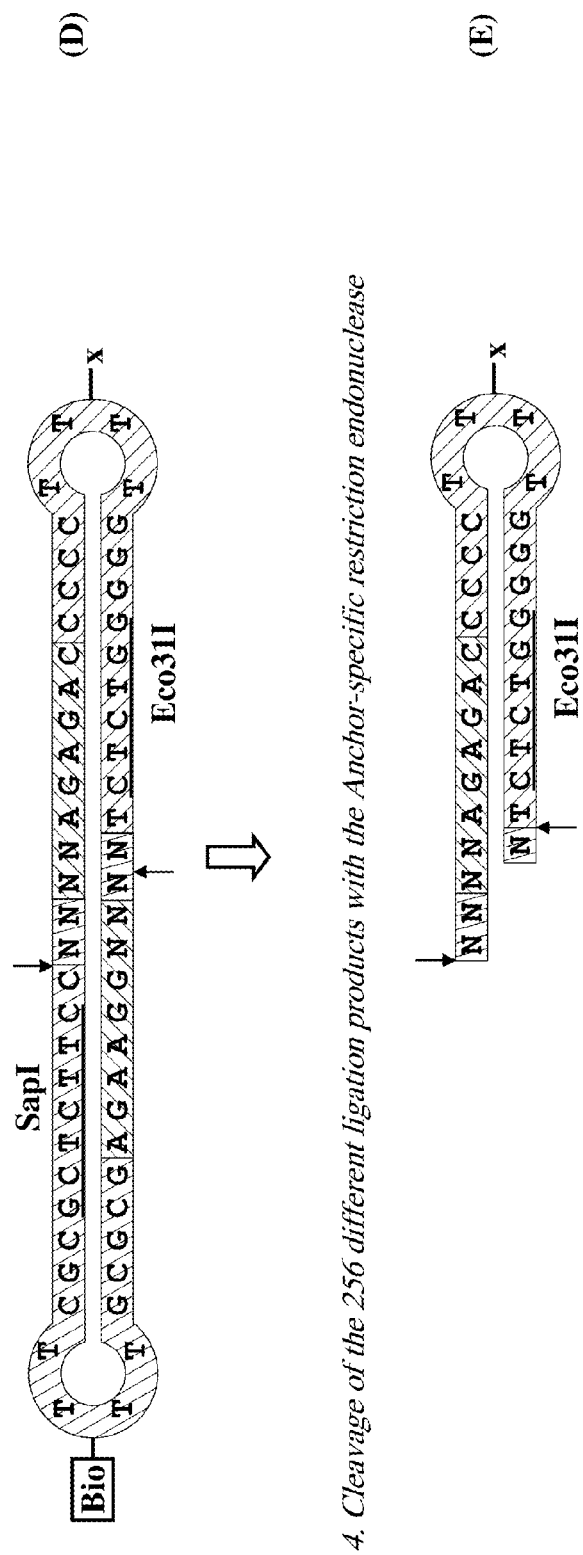
Figure 6:
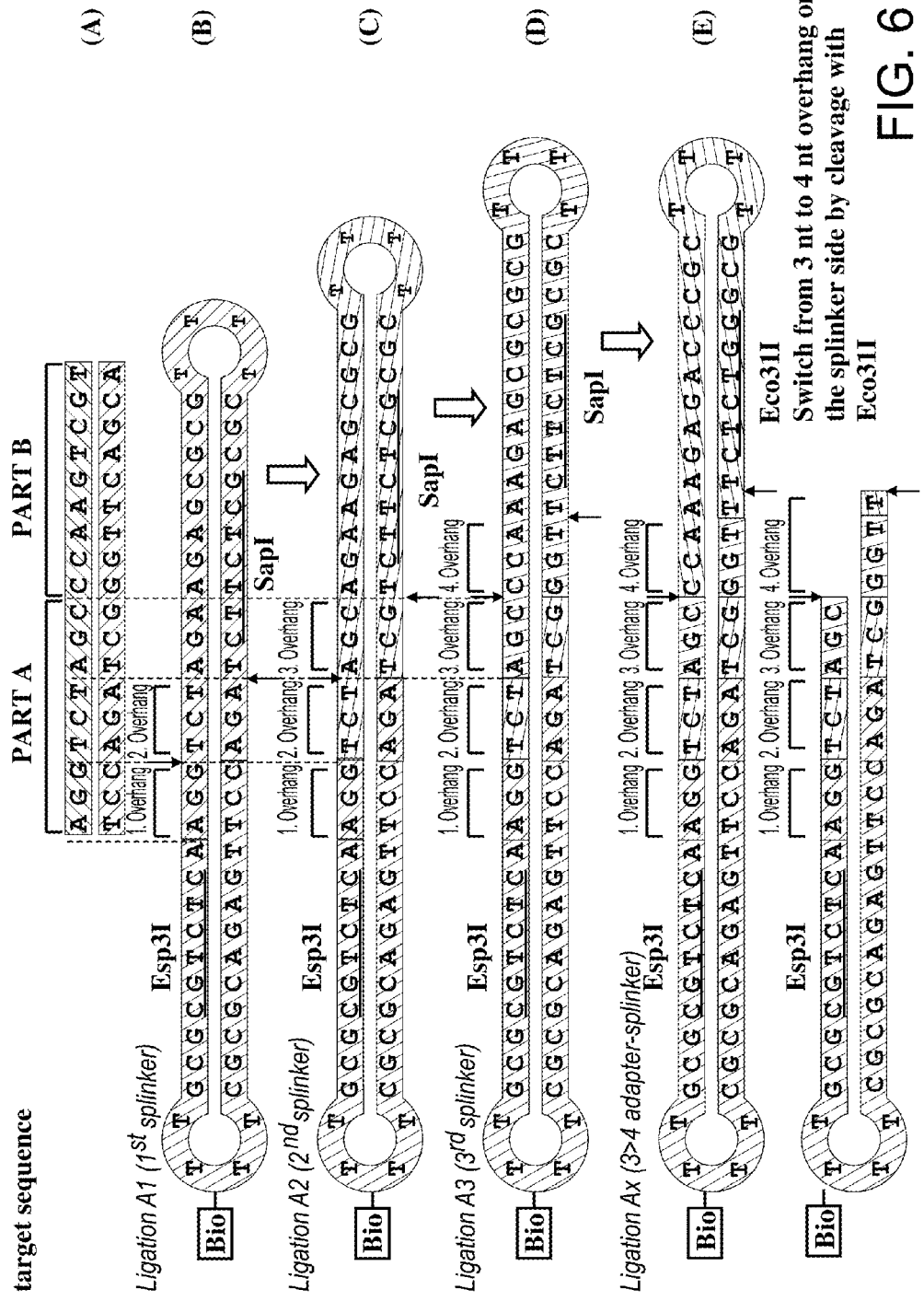
Figure 7:
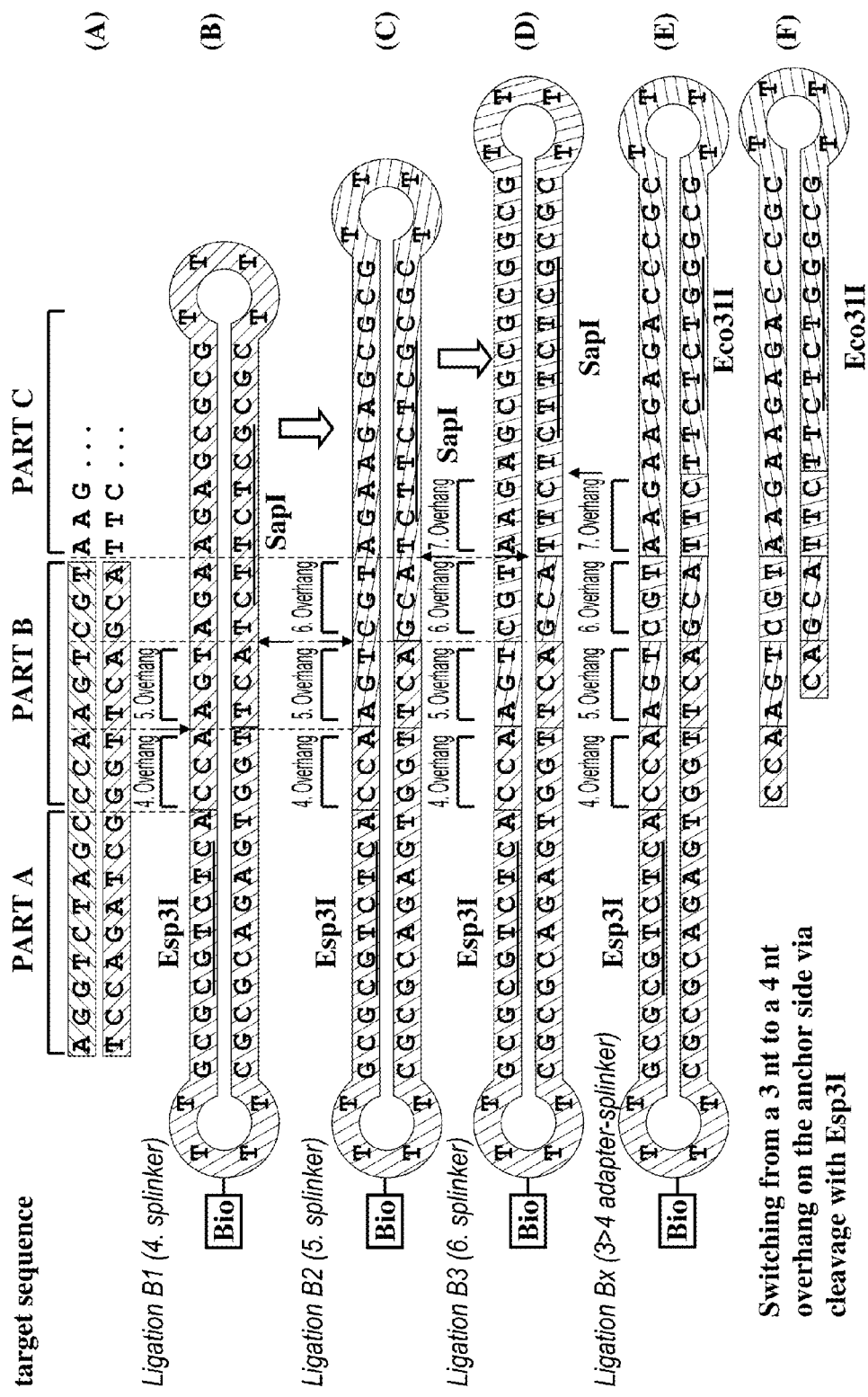
Figure 8:
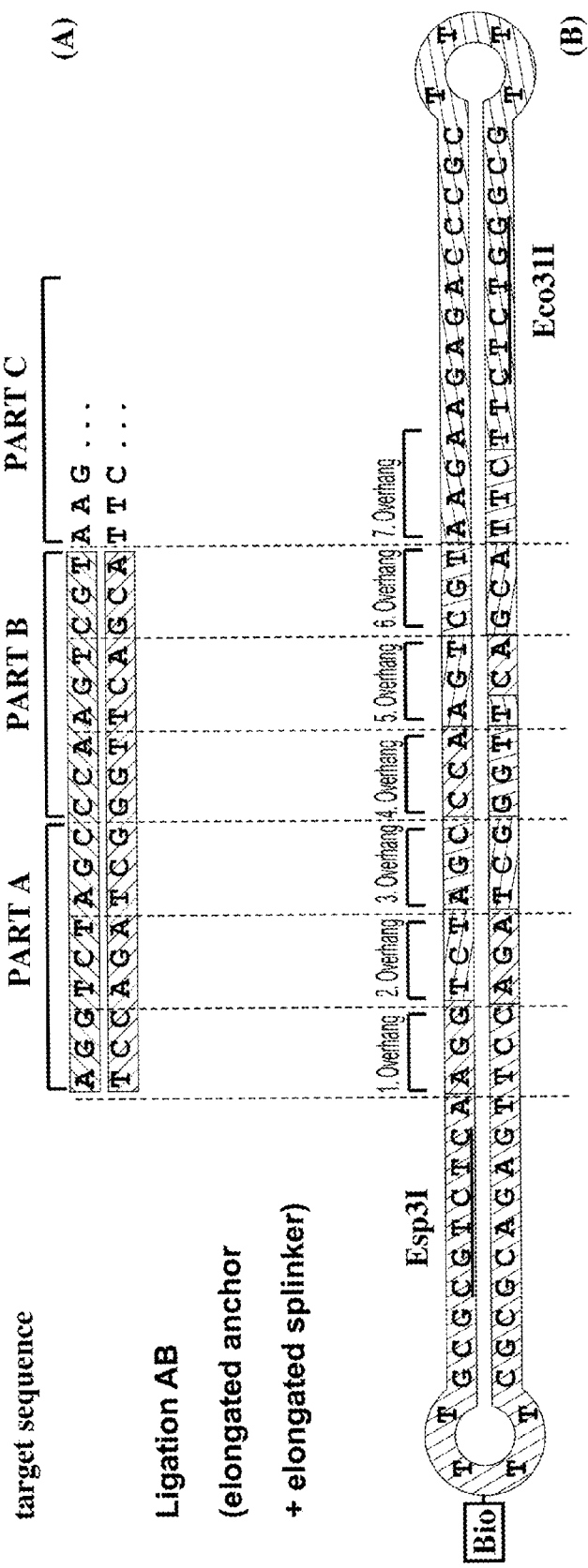
Figure 15:
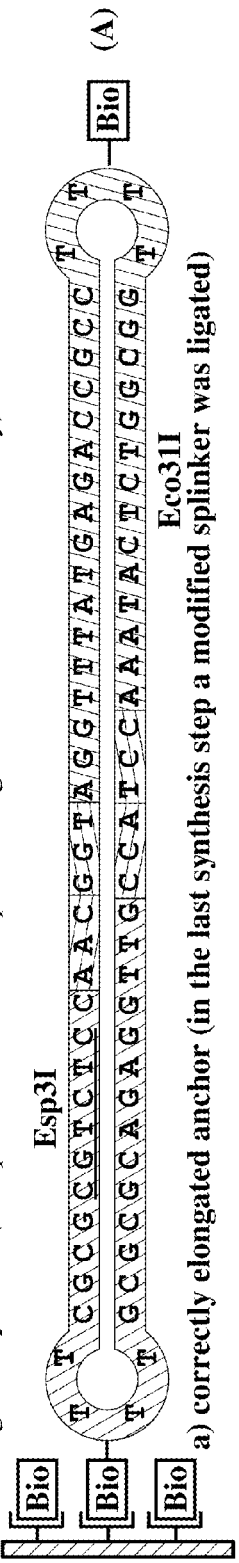
Figure 15:
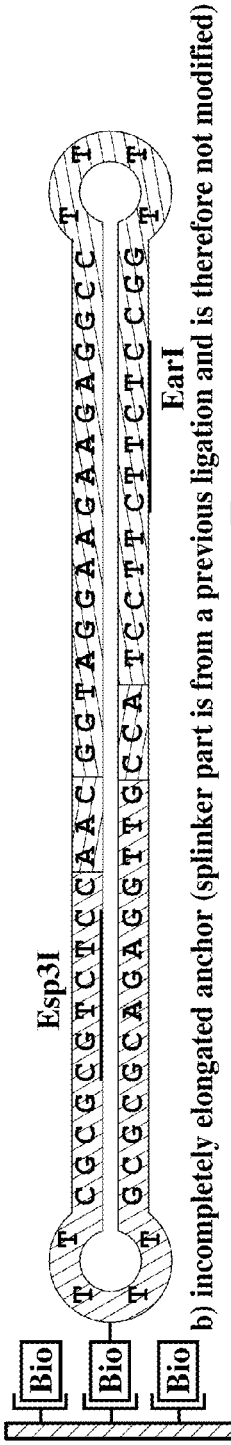
Figure 15:
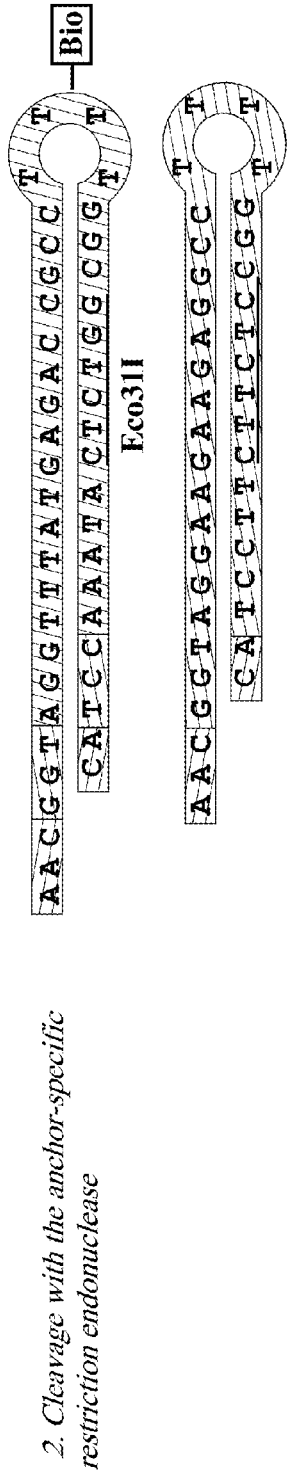
Figure 16:
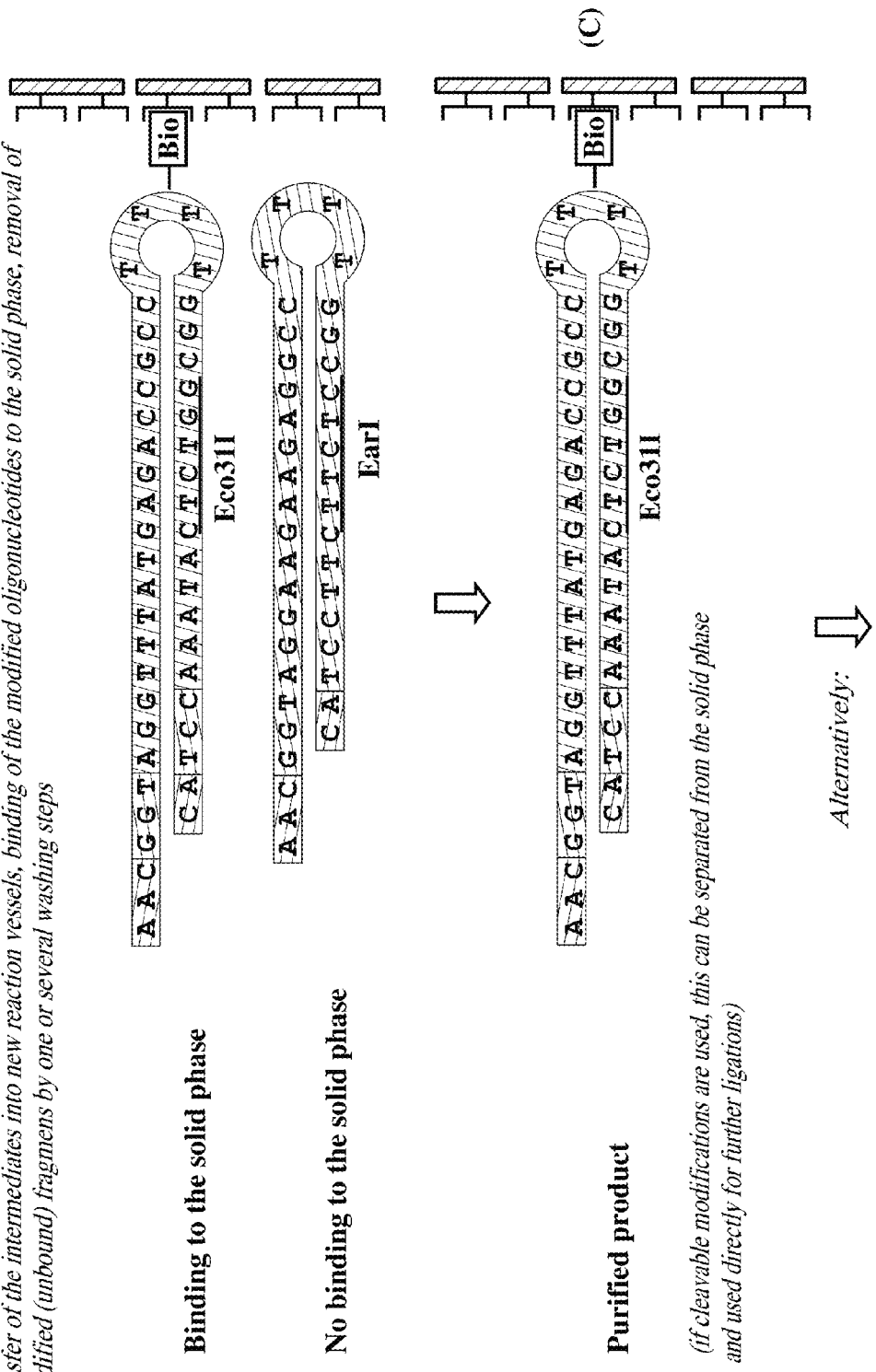
Figure 17:
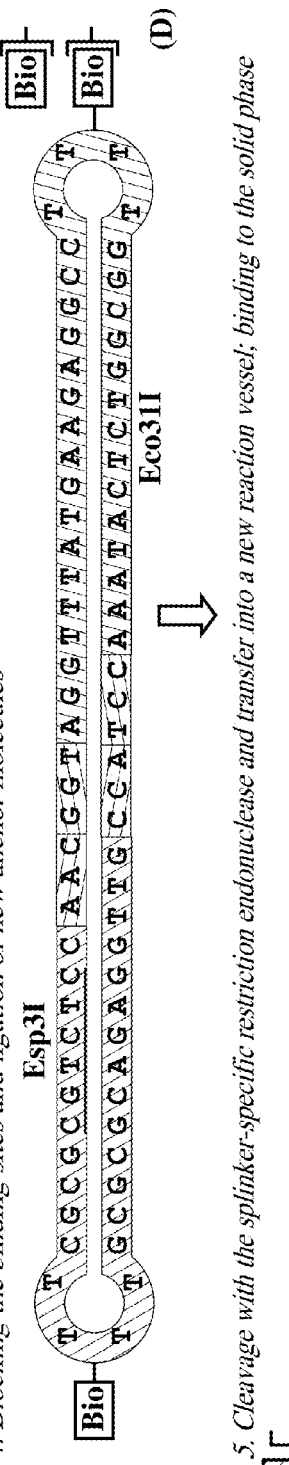
Figure 17:
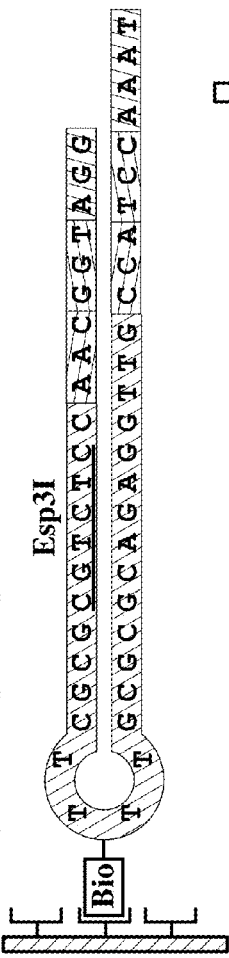
Figure 17:
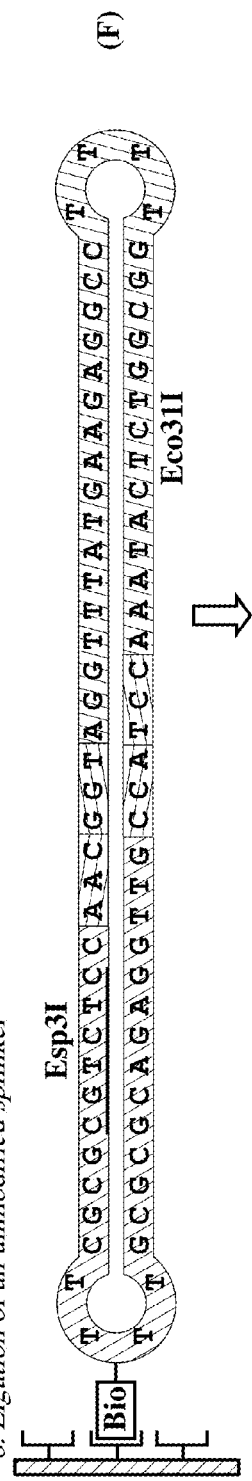
Figure 17:
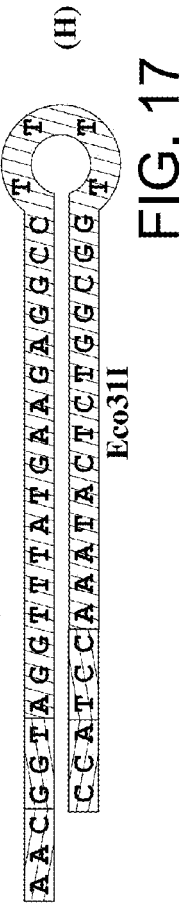
Figure 18:
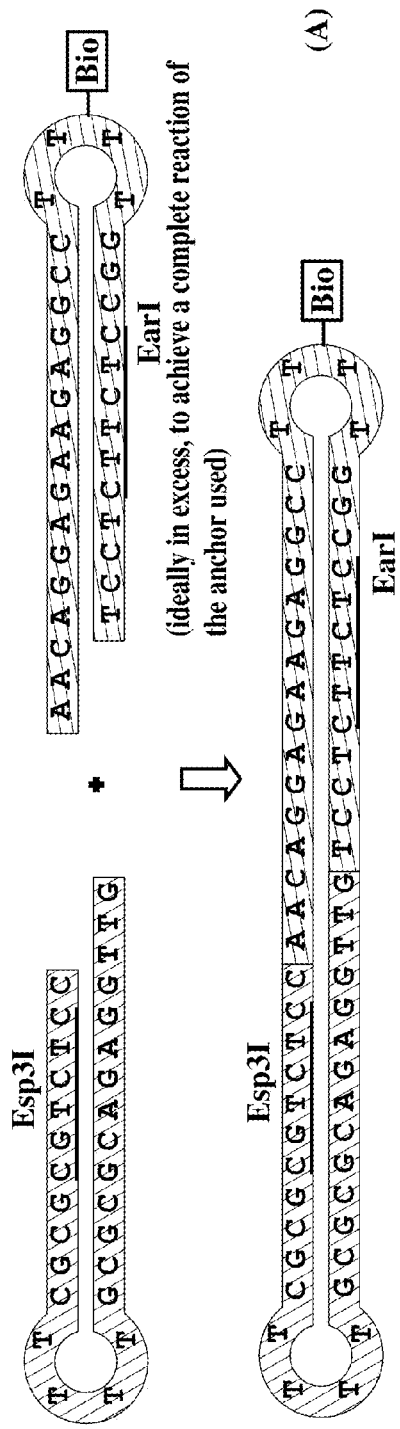
Figure 18:
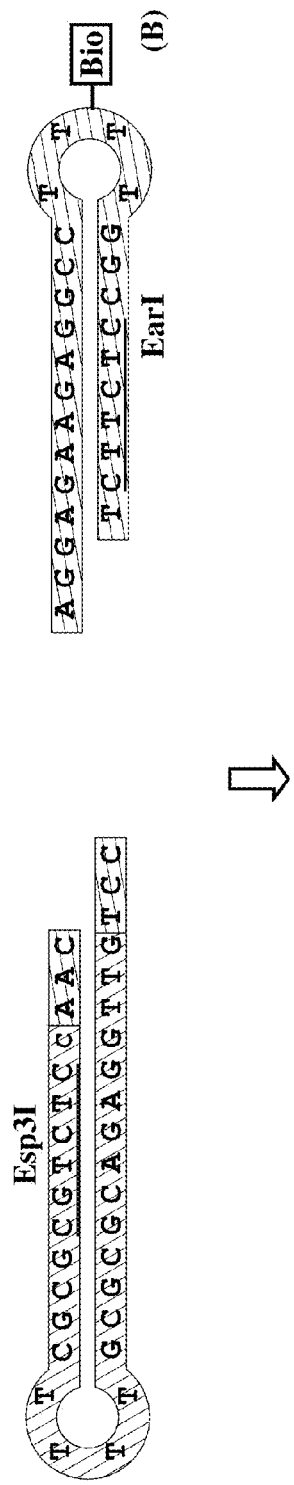
Figure 20:
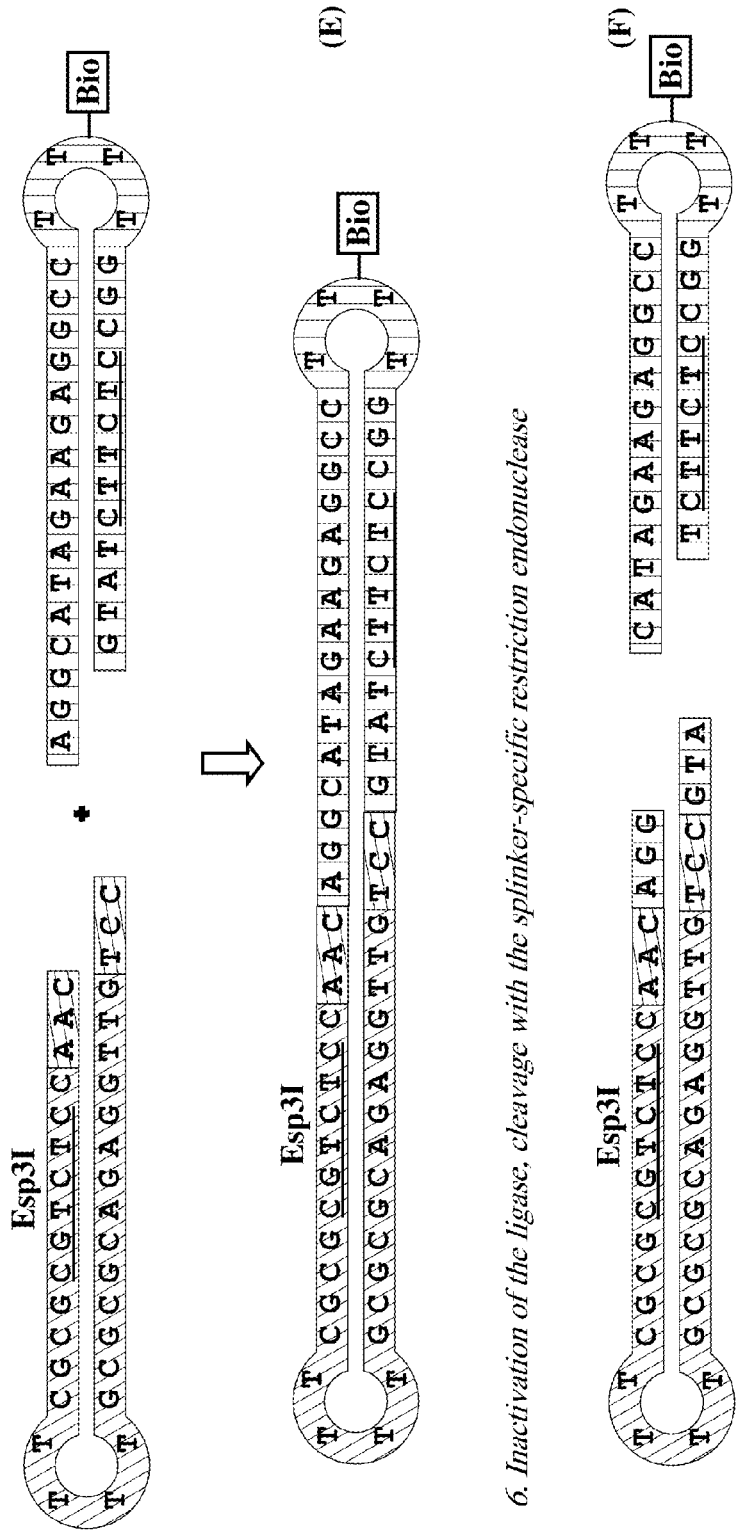
Figure 21:
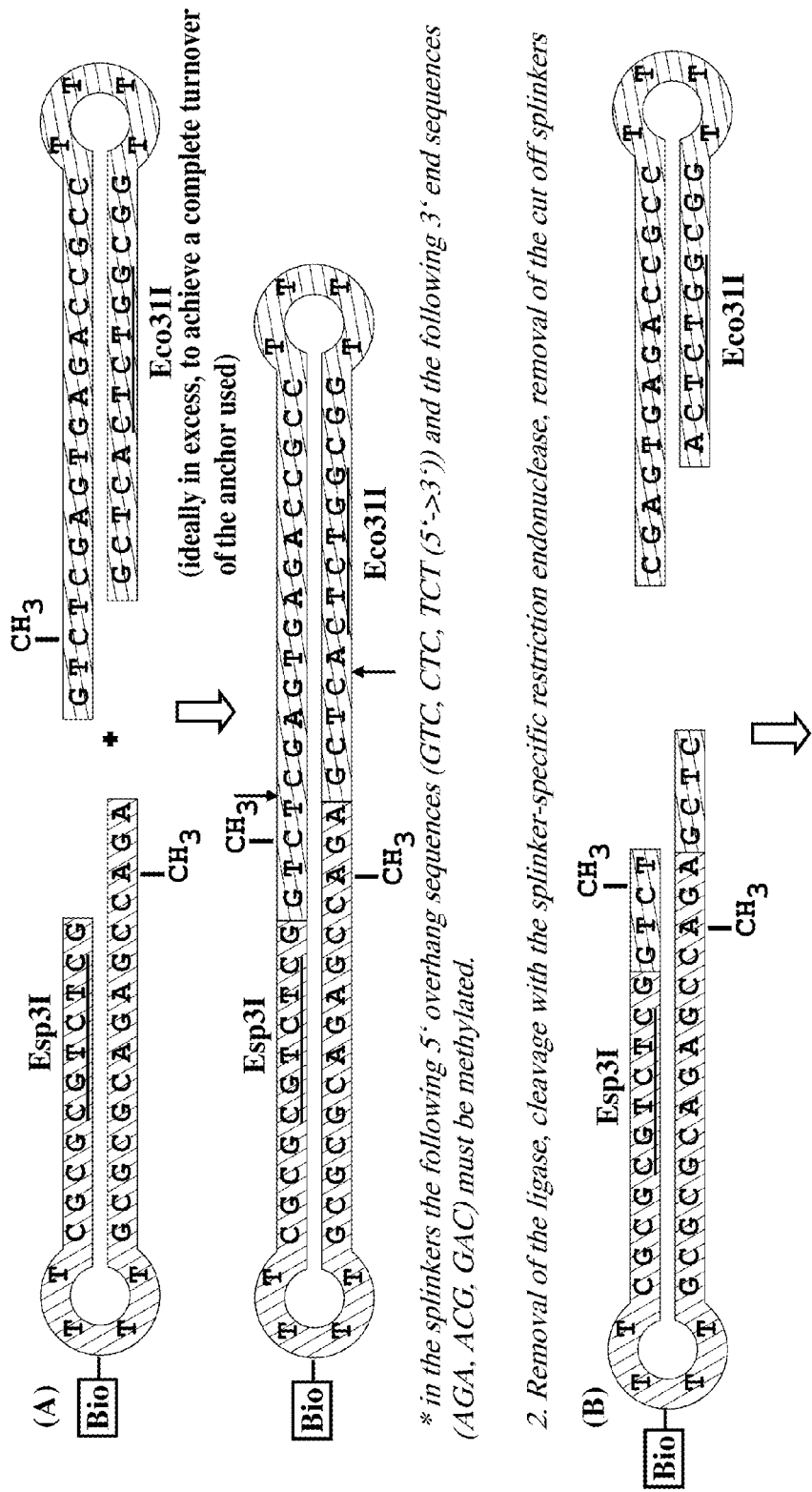
Figure 22:
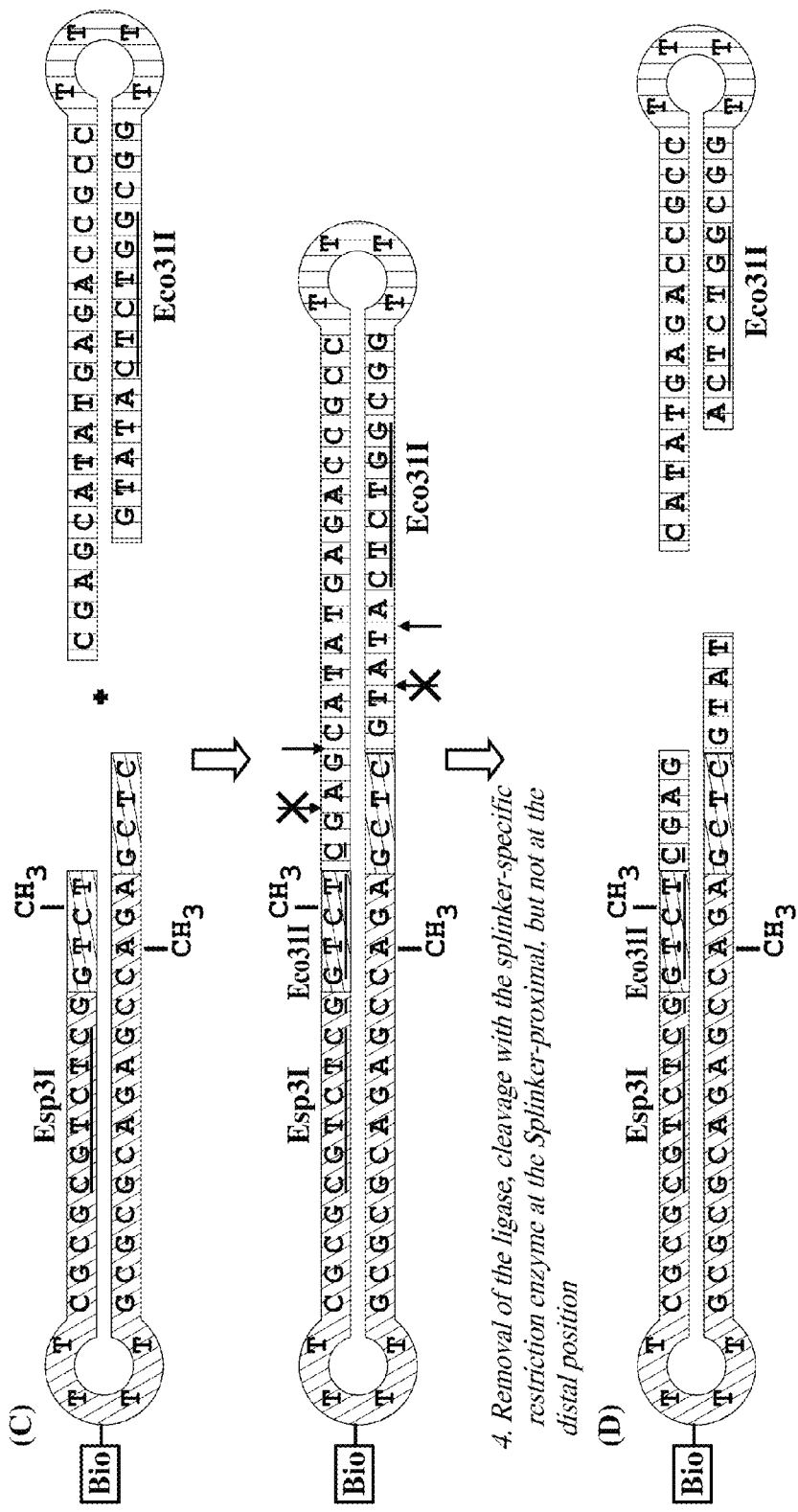
Figure 23:
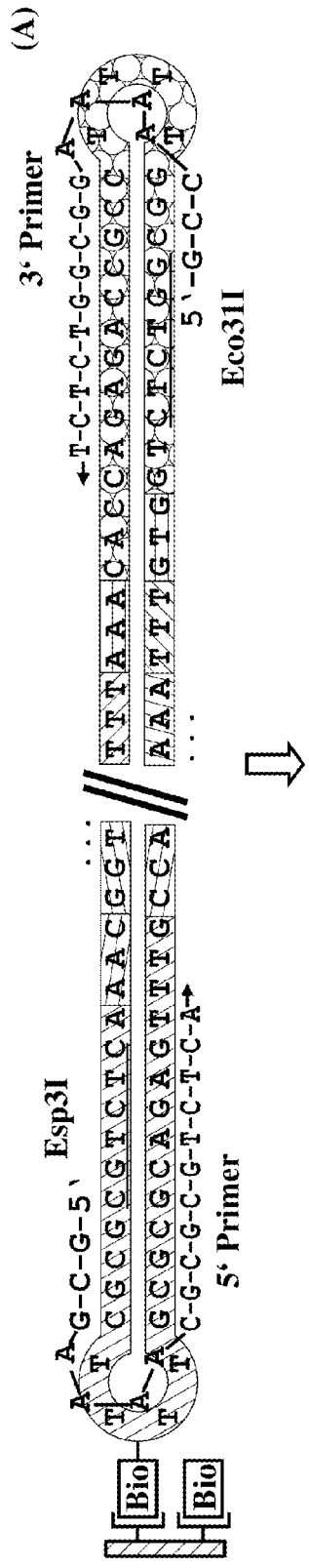
Figure 23:
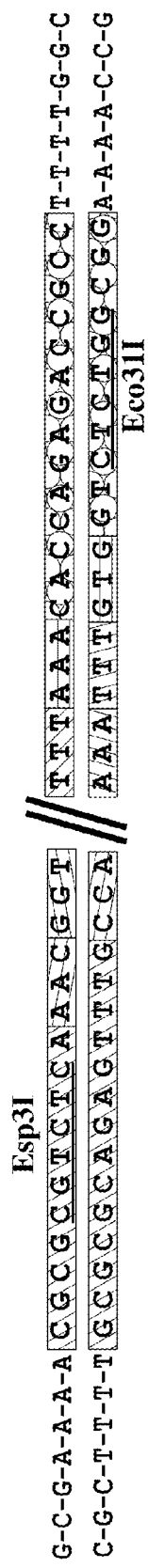
Figure 23:
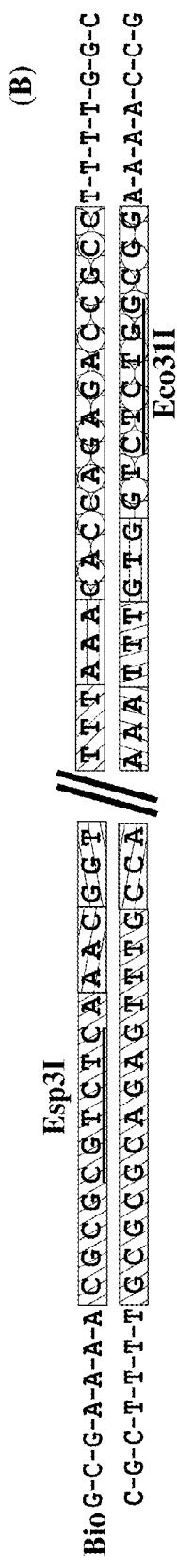

The present invention is now further illustrated by means of the following figures and examples, from which further features, embodiments and advantages of the invention arise. In this context, the figures show FIG. 1 the course of the inventive procedure FIGS. 2 to 3 the generation of a library of splinker molecules with an overhang of three nucleotides;

FIGS. 4 to 5 a procedure for the construction of a library, which allows the transition from splinker or anchor molecules with a three nucleotide overhang to such molecules with a four nucleotide overhang;

FIGS. 6 to 8 an embodiment of the Sloning procedure using anchor and splinker molecules with a three nucleotide overhang;

FIGS. 9 to 14 the basic steps of the inventive procedure for the simultaneous generation of different gene variants using the Sloning procedure;

FIGS. 15 to 17 the various steps in the removal of uncleaved incorrect sequences;

Figure 19:
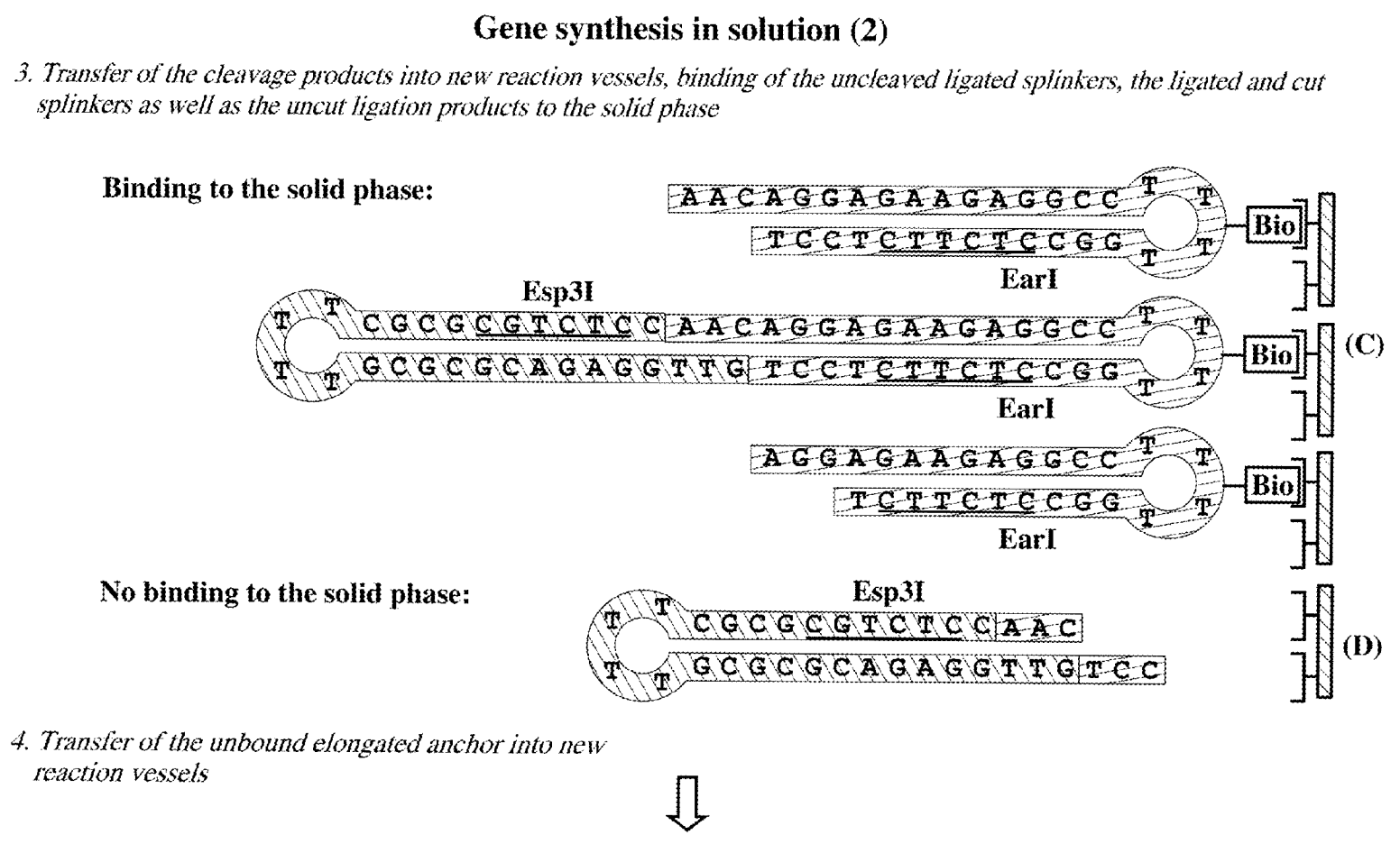

FIGS. 18 to 20 the various steps in the gene synthesis in solution, concerning a further embodiment of the Sloning procedure;

FIGS. 21 and 22 the basic steps in the synthesis of fragments with internal methylation according to the present invention, and FIG. 23 the procedure of the amplification of the (intermediate) product as it may be carried out in the context of various steps of the Sloning procedure FIG. 1 shows the cycle of the inventive procedure, in which a single-stranded linker molecule is used to reduce the size of the library of anchor and splinker molecules. In this case an oligonucleotide 1 is provided in a first step, which is also referred to as generic splinker or master splinker, and which comprises a single-stranded region comprising five nucleotides as well as a double-stranded region comprising seven nucleotides as well as a loop consisting of four nucleotides. The loop carries a modification X, which is suitable to bind oligonucleotide 1 to a solid surface. Preferably this concerns a reversible binding. The oligonucleotide 1 has a protruding 3' end. The 5' end is chemically or enzymatically phosphorylated.

In a second step oligonucleotide 2 is provided, which is herein also referred to as generic anchor or master anchor. Likewise, oligonucleotide 2 consists of a single-stranded region comprising five nucleotides, a double-stranded region comprising six nucleotides as well as a loop comprising four nucleotides. The loop carries a biotinylation allowing binding of oligonucleotide 2 to a surface. Similar to oligonucleotide 1 the 3' end protrudes by five nucleotides, and the 5' end is phosphorylated chemically or enzymatically. The protruding 3'—OH end of oligonucleotide 1 represents the recognition site of restriction enzyme X in this case.

Both oligonucleotide 1 and oligonucleotide 2 are bound, independently of each other, to a solid support, in the case of biotinylated oligos to Streptavidin-coated beads or microplates according to the instructions of the manufacturer. To the immobilized oligonucleotides 1 and 2 one then adds one linker respectively. In the present case part A of the linker comprises the sequence CGAGA and corresponds to the complementary strand of the last 4 nucleotides of the type IIS restriction enzymes Eco31I and Esp3I, and hybridizes with the corresponding single strand of oligonucleotide 1. Subsequently a ligation occurs using a ligase activity, leading to the formation of a complete recognition sequence of restriction enzyme Eco31I. The same thing happens with oligonucleotide 2, which is likewise immobilized on a surface. After ligating the linker to oligonucleotide 1 or oligonucleotide 2, respectively, part B of the linker protrudes in both cases and defines the region or nucleic acid sequence to be synthesized in the context of the synthesis.

This protruding end is specifically filled in with the appropriate nucleoside triphosphates after kinase and Klenow polymerase treatment so that in the end a filled in oligonucleotide (1) or oligonucleotide (2), respectively is immobilized at the surface. Depending in the nucleic acid to be synthesized one chooses those linkers the part B of which has the desired sequence. In the procedure depicted in FIG. 1 it is guaranteed by appropriate choice of the restriction enzyme pair that the same linker library can be used for the elongation or filling in of oligonucleotide 1 as well as oligonucleotide 2. This has become possible by the fact that the sequence of the oligonucleotide 1 and oligonucleotide 2 at the transition between the oligonucleotide and the linker was designed in such a way that after ligation the different recognition sites for the two restriction enzymes were formed.

As a next step, detachment of oligonucleotide 1 and/or oligonucleotide 2 from the surface may occur. Subsequently the two filled in oligonucleotides 1 and 2 are ligated. In a further reaction step the ligation product is then cleaved with one of the two type IIS restriction enzymes, in the present case with Esp3I. In this way complete splinker oligonucleotides with all possible 65536 octamer terminal sequences can be created.

Figure 2:
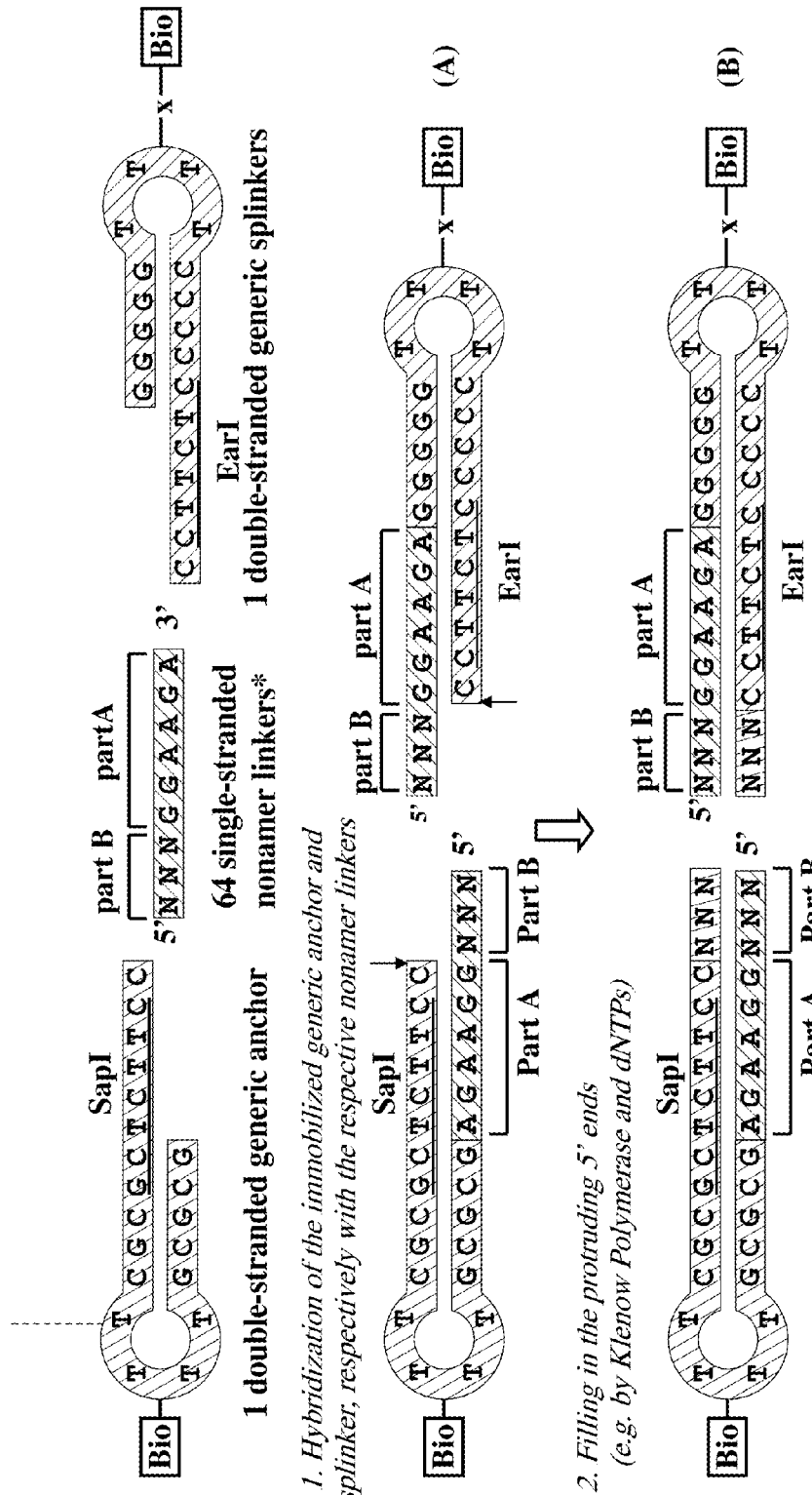
Figure 3:
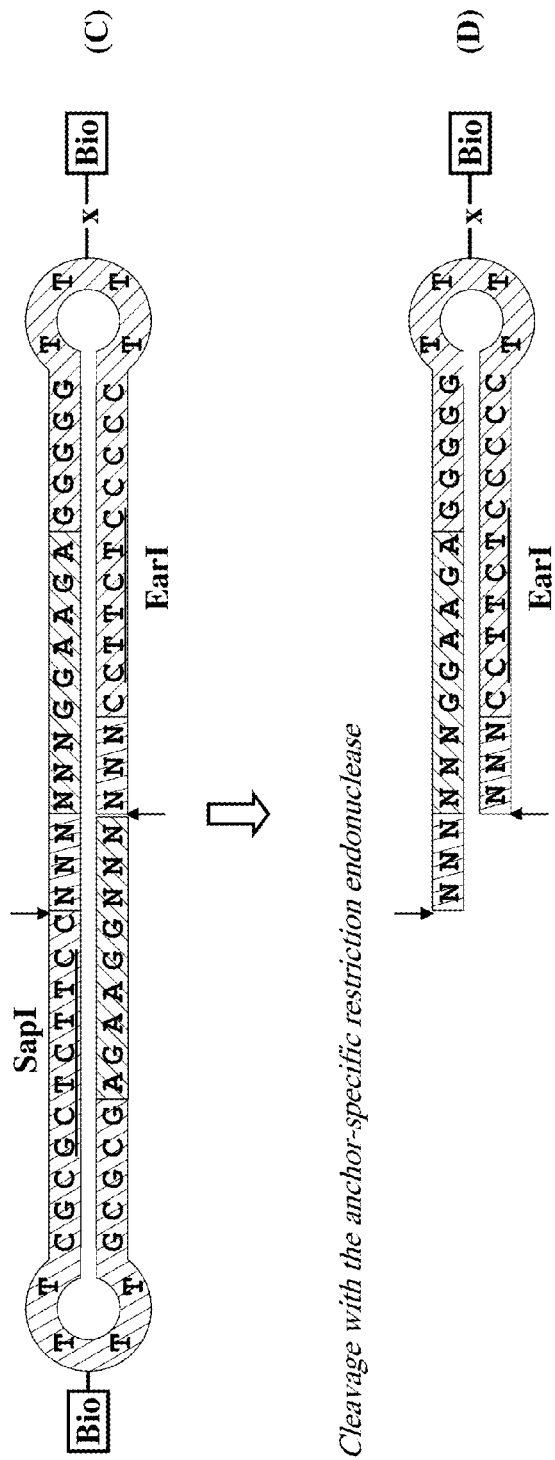

The FIGS. 2 and 3 depict the construction of a library of splinker molecules with an overhang of three nucleotides. As disclosed herein and obvious from the previously mentioned aspects, one preferably uses anchor and splinker molecules with a three nucleotide overhang, for example in the generation of gene variants and particularly of such gene variants pertaining coding nucleic acids. Insofar it is an aspect of this invention to provide a procedure for the generation of a library of splinker or anchor molecules with an overhang of three nucleotides. As an example for the generation of such molecules, the construction of a library of splinker molecules with an overhang of three nucleotides is depicted in FIGS. 2 and 3. In the context of the description of the FIGS. 2 and 3, the term "anchor" or "anchor molecules" denotes an oligonucleotide according to aa) or ba), respectively of the Sloning procedure, and the term "splinker" or "splinker molecule" denotes an oligonucleotide according to ab) or bb), respectively of the Sloning procedure.

The construction of the library starts from an anchor molecule, which carries a modification allowing a coupling to a solid matrix and a splinker molecule, which also carries a modification allowing a coupling to a solid matrix, whereby this splinker modification is preferably cleavable. To an anchor molecule, more precisely a generic anchor molecule (the same for all splinker or anchor oligonucleotides to be synthesized) one adds a single-stranded nucleic acid molecule, herein also referred to as linker, which in the present case consists of a nonamer comprising a part B and a part A. Part A is in this case complementary to the 5' overhang of the anchor molecule. Part B comprises three nucleotides comprising any desired sequence. In the same manner one preferably proceeds for a generic splinker molecule, i.e. one adds a linker likewise consisting of a part A and a part B, whereby the parts A and B are in principle identically designed as in the case of the linker added to the anchor molecule. In view of the fact that at each of the three positions, denoted as N in FIG. 16(A) there may be one of the four nucleotides, one can, with 64 different single-stranded linkers, represent the complete range of sequences, i.e. all possible molecules that may differ in these three nucleotide positions. Preferably, the length of the part A of the linker is six nucleotides, whereby however linkers with larger and smaller lengths of part A are also within the scope of protection.

By hybridization of the anchor or the splinker molecule, with one of a total of 64 linkers respectively, a total of 64 different anchor or splinker molecules can be formed, which each differ in part B. In this context, part A of the linker is typically complementary to the recognition sequence or a part thereof of the anchor- or splinker-specific restriction enzyme or to the sequence complementary thereto. The overhangs of the anchor or splinker molecules, respectively, which have been filled in with the linker, are then filled in with a polymerase, as for example Klenow polymerase thus creating anchor and splinker molecules with blunt ends.

The anchor molecule as well as the splinker molecule are preferably coupled to a surface or a solid matrix. The modification of the splinker molecule can preferably be cleaved under mild conditions so that the filled in splinker can be detached from the surface and be added to a ligation reaction with a suitable blunt end anchor molecule.

In a next step the ligation product from step (C) is then cleaved with an anchor-specific type IIS restriction endonuclease, whereby splinker molecules with a three nucleotide overhang are generated. In the same manner, the cleavage with the splinker-specific restriction endonuclease can occur. By this process one can create, starting from a total of 64 different single-stranded linkers differing in three consecutive nucleotides, a total of 4096 different double-stranded splinker molecules, which can then be used as starting library for a Sloning procedure in the described manner.

In the synthesis of gene fragments from anchor and splinker molecules according to the invention it is required to provide anchor or splinker molecules, respectively that have a three nucleotide overhang but carry a recognition site for a type IIS restriction enzyme that creates overhangs with a length of one, two, four, five or more nucleotides. This is necessary because in any case at least two type IIS restriction enzymes with different recognition sites have to be used for the execution of the Sloning procedure, which moreover create overhangs of the same length. Presently, however, the only known isoschizomers of type IIS restriction enzymes creating a three nucleotide overhang, recognize the same sequences. One of these restriction enzymes is SapI. Prior to the transition into the transposition phase (i.e. the assembly of the partial fragments synthesized in parallel, which have to be cleaved in pairs, respectively with the different restriction enzymes) it is first necessary to create fragments with an overhang of identical length (e.g. consisting of 4 nucleotides).

The FIGS. 4 and 5 show a procedure for the synthesis of a library, which allows the transition from splinker or anchor molecules, respectively from a three nucleotide overhang to such molecules with a four nucleotide overhang. Thereby one basically proceeds in a similar manner as with the above described procedure for the synthesis of a library of splinker and anchor molecules with a three nucleotide overhang. The main difference is in the design of the linker molecule, which, as shown in (A), in the present case has a length of two nucleotides. Insofar 32 single-stranded linker molecules, 16 anchor-specific as well as 16 splinker-specific, are sufficient to build up a complete library, i.e. a library comprising a 11 possible sequences differing in the last two 5' terminal positions. In step (D) one then cuts with the anchor-specific restriction endonuclease, in the present case SapI, thereby generating a three nucleotide overhang. With this procedure a total of 256 different double-stranded molecules can be generated, which when used allow the transition from splinker and anchor molecules with a three nucleotide overhang to such molecules with a four nucleotide overhang and are therefore also referred to as splinker-adapters.

Based on the previously described two libraries and the procedures for their generation, a synthesis of gene fragments from anchor and splinker molecules can take place. The corresponding procedure is depicted in the FIGS. 6 to 8. In the context of the description of the figures, the term "anchor" or "anchor molecules" denotes an oligonucleotide according to aa) or ba), respectively of the Sloning procedure, and the term "splinker" or "splinker molecule" denotes an oligonucleotide according to ab) or bb), respectively of the Sloning procedure.

If one starts from the sequence to be synthesized shown in (A), herein also referred to as target sequence, this can be subdivided into the parts A and B as in the present case. Part A as well as part B consist of 9 nucleotides, which are arranged in three groups of three nucleotides each. Correspondingly, starting from an anchor coupled to a solid matrix, the first group of three nucleotides can be transferred to the anchor molecule by ligation of a first splinker molecule. By cleavage of the ligation product in step (B) with the type IIS restriction enzyme SapI, which generates a three nucleotide overhang, one generates a further three nucleotide overhang, to which a second splinker molecule is ligated in step (C), which is subsequently cleaved off with the splinker-specific restriction enzyme.

In the same manner one proceeds with a third splinker molecule, whereby the ligation product according to (D) is then obtained. After the cleavage of the ligation product from (D) one now uses, in step (E), a splinker-adapter allowing the transition from a three nucleotide overhang to a four nucleotide overhang. If after ligation this splinker molecule, also referred to as adapter-splinker or 3→4 adapter-linker, ic cleaved with the splinker-specific restriction enzyme, in the present case with Eco31I, this does not generate a three nucleotide overhang but a four nucleotide overhang and thus creates the pre-condition for a transposition in the context of the Sloning procedure, in which two matched type IIS restriction enzymes are used.

In the steps (B) to (E) of FIG. 7 one proceeds in principle in the same manner as in the steps (B) to (E) of FIG. 6, whereby here the splinker used in step (B) has a 3 nucleotide overhang corresponding to first triplet of part (B) of the target sequence. After the third triplet of part B has been ligated via a respective splinker molecule to the elongated anchor molecule, one cuts again with SapI and uses then a further splinker molecule comprising the first triplet of part C of the target sequence. To create the precondition for a transposition also in this case, one then cleaves with the anchor-specific type IIS restriction enzyme, in the present case Esp3I, thereby generating a four nucleotide overhang. The target sequence from part A and part B, as shown in (A) of FIG. 8 is synthesized by the fact that the cleavage product, i.e. the anchor molecule with a four nucleotide overhang from FIG. 6 (F) is ligated with a splinker molecule from step (F) having a four nucleotide overhang.

The FIGS. 9 to 14 show the basic steps of the inventive procedure for the simultaneous production of different gene variants using the Sloning procedure. In the context of this further embodiment of the Sloning procedure it should be annotated that the relevant point herein is that a correctly elongated anchor molecule or a correctly elongated splinker molecule is divided into several reactions, preferably in different reaction vessels. This partitioning is not unproblematic, particularly when the modification of the anchor or splinker molecules, respectively allow a coupling to a solid matrix, which does not permit said molecules to be released, as is e.g. the case when using non-cleavable modifications or modifications that result in a very stable interaction between the nucleic acid or the modification, respectively and the solid matrix.

As shown in FIGS. 9 to 14, this embodiment of the Sloning procedure is characterized basically by the specific design of the steps aa) to ag) or ba) to bg), respectively. In the context of the description of the FIGS. 9 to 14, the term "anchor" or "anchor molecules" denotes an oligonucleotide according to aa) or ba), respectively of the Sloning procedure, and the term "splinker" or "splinker molecule" denotes an oligonucleotide according to ab) or bb), respectively of the Sloning procedure.

Provided that the binding sites of the solid matrix have been blocked, a special splinker molecule can be ligated to the elongated anchor molecule in place of the normal (non-modified) splinker oligonucleotide. This special splinker molecule contains a modification, which allows a coupling to a solid matrix (A). In a next step (B) the thus formed ligation product is cleaved with the anchor-specific type IIS restriction enzyme. As a result of this cleavage an elongated splinker molecule is released, which carries a modification and is present in solution in this reaction. This reaction, more precisely the liquid supernatant thereof is then aliquoted to the desired extent, particularly to the extent, in which different gene variants are to be generated. If, for instance, three gene variants are to be generated, as illustrated for example in the FIGS. 9 to 14 herein, the liquid supernatant is divided into a total of three aliquots.

Each aliquot that contains a separated, elongated splinker molecule with a modification is transferred to a reaction vessel of its own, whereby the elongated splinker molecule is bound to the solid matrix due to the modification (C). The cartoons denoted as reaction 1, reaction 2 and reaction 3 in FIG. 10 (C) depict the overall three reactions herein described by example.

To each reaction an anchor molecule is then added, which hybridizes to the splinker molecule coupled to the solid matrix due to the complementarity of the overhangs, and which is subsequently ligated using suitable ligases. Since the anchor molecules themselves carry a modification allowing a coupling to solid matrix, it is necessary to block the binding sites for this matrix prior to the addition of the anchor molecules so that a coupling of the added anchor molecules to the solid matrix does not occur. This blocking step is not required if the modification of the anchor molecules does not allow a coupling to the solid matrix, in which the splinker molecule attached to a solid surface is contained.

In a next step the ligation product is then cut with a splinker-specific type IIS restriction enzyme (E). Since the anchor in step (D) in FIG. 10 carries a modification but cannot couple to the solid matrix, the elongated anchor will be, after the cleavage of the ligation product, in the liquid supernatant of the reaction whereas the splinker molecule remains bound to the solid matrix due to the coupling via the modification. Each of the supernatants is then transferred to a new reaction vessel, whereby the elongated anchor contained therein is coupled to the surface due to its modification (E).

To the thus immobilized anchor molecules one adds in each of the respective reactions different splinker molecules, whereby the splinker molecules differ in a variable region following the 5' overhang. Preferably, the following variable region has a length of 1 to 9 nucleotides, whereby 3 nucleotides are preferred as one can thereby provide a codon for a coding sequence. In the reactions shown in FIG. 11 (F) the splinkers differ at the positions 4 to 6 (AGA, CCG and GTT, respectively). If now the thus obtained ligation product from step (F) is cut with a splinker-specific restriction endonuclease, different elongated anchor molecules are formed in the reactions. In reaction 1 the variant comprises nTTT, in reaction 2 GGC and in reaction 3 CAA (G). In a next step different linker molecules are then added, the overhang of which is complementary to the overhang of the immobilized anchor molecules. Due to the variability of the overhang of the individual anchor molecules in the reaction one must add to each reaction those splinker molecules that have a respective complementary sequence so that each reaction requires another linker (FIG. 7 (H)).

Preferably the various splinker molecules differ only in this region. Subsequently, another cleavage occurs of the ligation product obtained in step (H) with a splinker-specific restriction endonuclease (J). In a next step a further splinker molecule is then ligated, which is complementary to the respective overhang of the elongated anchor molecule in each of the three reactions. Here the same linker can be used in each case because the overhangs of the elongated anchor molecules produced in step (J) have an identical sequence. The splinker molecule added in step (J) can be such a one enabling the transition from a three nucleotide overhang to a four nucleotide overhang, as shown in FIGS. 4 and 5.

This transition using an oligonucleotide with an overhang three nucleotides in length, the recognition sites of which for a type IIS restriction enzyme produce, upon cleavage with this enzyme, a four nucleotide overhang, is herein also referred to as splinker-adaptor. It is intended in the herein specially described embodiment that this splinker-adapter has a modification, which allows a coupling to the surface of a solid matrix. Depending on whether the ligation product obtained in step (J) is cleaved with a splinker-specific type IIS restriction enzyme, one either obtains the elongated anchor molecules shown in step (K), which are coupled to a solid matrix or, when using an anchor-specific type IIS restriction enzyme, the splinker molecules shown in (L). In the first case the gene variants are arranged on the anchor side, in the second case on the splinker side. The design of the splinker molecule with a modification is a precondition for the use of a thus elongated splinker molecule as anchor molecule in a transposition step of the Sloning procedure.

Although in the FIGS. 9 to 14 only the one-time introduction of a gene variant has been described, it is within the scope of the present disclosure that this can be done several times. In order not to obtain splinker and anchor molecules that are unnecessarily long and thereby abandon the advantage of the parallel synthesis, i.e. carrying out transpositions, the integration of a gene variant as described above typically occurs less than ten times, preferably less than five times.

The FIGS. 15 to 17 show the different steps of the removal of uncleaved failure sequences according to the present invention. In the context of the description of the FIGS. 1 to 3, the term "anchor" or "anchor molecules" denotes an oligonucleotide according to aa) or ba), respectively of the Sloning procedure, and the term "splinker" or "splinker molecule" denotes an oligonucleotide according to ab) or bb), respectively of the Sloning procedure.

As with the herein collectively disclosed further embodiments of the procedure for the production of nucleic acid molecules by parallel synthesis referred to as Sloning procedure, the nucleic acid molecule, which is produced by the steps aa) to ag) and the oligonucleotide, which is produced according to steps ba) to bg) can be combined. This combination is also herein referred to as transposition.

During the execution of the Sloning procedure the situation may occur that defective intermediates may be formed in the context of the sequential addition of splinker molecules from the library (herein also described as elongation synthesis) in such a way that (e.g. by incomplete cleavage of the splinker-specific type IIS restriction enzyme) both correctly elongated as well as incompletely elongated anchor and splinker molecules are present in the reaction. The presence of such incompletely elongated molecules would lead to an incorrect sequence in case they are used as elements in the transposition. For this reason, there is a need to adapt the Sloning procedure in such a way to make sure that only correct sequences, in particular at the level of the anchor molecules are used in the transposition phase, i.e. the parallel assembly of the synthesized gene fragments. In the context of the present invention this is achieved by using a modified splinker molecule prior to the last ligation of the anchor molecule with a splinker, i.e. before the transposition of the ligation product obtained by this ligation, whereby the modification is that the splinker, principally comparable to the anchor molecule carries a modification, which allows coupling to a solid matrix. Since it is not possible to ligate such a modified splinker molecule to molecules of the reaction, which have not been cleaved by the splinker-specific type IIS restriction enzyme, only the ligation products of the correctly elongated anchor with the respective last (modified) splinker molecule carry a modification. The incompletely elongated anchor molecules have, as a product from a previous ligation the splinker molecules used therein, which do not carry such a modification (see FIG. 1(A)).

In a further step (B) the cleavage of the correctly elongated anchor molecules present in the reaction occurs with the anchor-specific type IIS restriction enzyme. The cleavage products not coupled to the solid matrix are for one thing correctly elongated splinker molecules, which carry a label as well as incompletely elongated splinker molecules carrying no label (B). The thus obtained splinker molecules are preferably transferred to a new reaction vessel. The vessel has a surface as solid matrix, which allows a coupling via the modification present on the correctly elongated splinker molecule. This results in an immobilization of the correctly elongated splinker molecules whereas the splinker molecules, which are not correctly elongated and which miss the modification allowing the coupling to a solid matrix do not bind to the solid matrix. By one or several washing steps the splinker molecules, which are not correctly elongated are removed from the reaction. The correctly elongated splinker molecule remains bound to the matrix and can be removed from this matrix in case cleavable modifications are used and which can then be ligated with the originally used anchor molecule (C), whereby the sequence of the anchor molecule is identical to the sequence of the originally used anchor molecule.

Alternatively and in the case that the modification does not permit cleavage of the correctly elongated splinker molecule, one adds an anchor molecule carrying a modification allowing a coupling to a solid matrix but in this case not bound to a surface, to the reaction containing solely the immobilized, correctly elongated splinker molecule. The binding to the surface of the anchor molecule carrying a modification can be prevented by the fact that the anchor possesses another modification than the one used for the coupling of the correctly elongated splinker to the surface. In case the modification are identical, the free binding sites of the matrix can be saturated or blocked by adding the molecule mediating the modification prior to the addition of the anchor molecule. When using the biotin-streptavidin system, this can be done by example by adding soluble biotin. Thereby the anchor molecule binds to the correctly elongated splinker molecule, which is coupled to the solid matrix as a consequence of the hybridization or base pairing of the overhangs, which is followed by a ligation using suitable ligases (D).

The thus obtained ligation product is then cleaved with a splinker-specific type IIS restriction enzyme. The thus obtained cleavage product, which is present in the supernatant of the reaction vessel is transferred to a new reaction vessel, whereby in this case the correctly elongated anchor molecule is initially present in solution but is immobilized to the solid matrix of the new reaction vessel due to the modification allowing a coupling to a solid matrix (E).

In a next step a suitable splinker molecule is added to the correctly elongated anchor molecule, which is bound to the solid matrix. Due to the respective complementary overhangs of the correctly elongated anchor molecule and the splinker molecule, they can hybridize with each other. The thus obtained annealing product can then be ligated by means of a ligase activity (F).

In a last step (H) the thus obtained ligation product is cleaved with an anchor-specific type IIS restriction enzyme and a correctly elongated splinker molecule is obtained in solution, which then both may be subject of a transposition Taken together one can say that by means of this specific procedure design one can guarantee that interfering oligonucleotides, i.e. ones that are incorrect in their sequence, can be removed from the reaction. The necessity for removing oligonucleotides that are not correctly elongated is important for an especially good yield and the correctness of the oligonucleotide to be synthesized, which is used as anchor or splinker molecule in the context of the Sloning procedure.

In principle, this procedure can also be applied after each synthesis step. In this case the actual gene synthesis occurs in solution whereas incorrect intermediates are removed from the reaction by binding to a suitable solid phase. FIGS. 18 to 20 show the different steps of such a gene synthesis in solution, which is another embodiment of the Sloning procedure.

In step (A) an anchor molecule, which in the present case carries no modification allowing a coupling to a solid phase is ligated with a splinker molecule. In this case, the splinker molecule carries a modification allowing a coupling to a solid matrix. This reaction occurs in solution, i.e. neither the added splinker molecule nor the ligation product of the anchor molecule and the splinker molecule is initially bound to a solid phase (A). By this a permanent selection for correctly elongated and cleaved intermediates is achieved. A further advantage of this procedure is that both ligation as well as restriction reactions generally proceed with a higher efficiency in solution than on the solid phase.

After inactivation of the ligase has occurred one cleaves with the splinker-specific type IIS restriction endonuclease. As a consequence, the reaction contains an elongated anchor molecule as well as the splinker molecule again in solution. The thus obtained cleavage products are then transferred to a new reaction vessel, in which due to the presence of a modification at the splinker molecule (in the present case a biotin) they bind to the solid matrix. Beside the cleaved splinker molecule the reaction further contains uncleaved ligation products from step (A) as well as unligated splinker molecules. All three splinker molecule derivatives bind to the solid phase but not the elongated anchor molecule obtained from step (B), which is still present in solution (C). The supernatant from step (C), i.e. the elongated anchor molecule is then transferred into a new reaction vessel and is there reacted with a further splinker molecule, which is complementary at its ends to the end of the elongated anchor molecule (E). The new splinker molecule in turn has a modification, which allows a coupling to a solid matrix.

The thus obtained ligation product is cleaved, after the inactivation of the ligase, with the splinker-specific type IIS restriction enzyme and thereby provides a further elongated anchor molecule.

This kind of procedure c an principally be repeated as many times as desired. The special advantage of this embodiment of the Sloning procedure consists in the fact that a purification of an oligonucleotide usable in the Sloning procedure is guaranteed. This kind of procedure can principally be applied to each level of the Sloning procedure.

The FIGS. 21 and 22 show the basic steps in the synthesis of fragments with internal methylation according to the present invention, which can be steps of the Sloning procedure. In this respect, a further embodiment of the Sloning procedure is hereby disclosed.

In the context of the description of the FIGS. 21 and 22, the term "anchor" or "anchor molecule" denotes an oligonucleotide according to aa) or ba), respectively of the Sloning procedure, and the term "splinker" or "splinker molecule" denotes an oligonucleotide according to ab) or bb), respectively of the Sloning procedure.

In the context of the synthesis of nucleic acid molecules as for example gene fragments using the Sloning procedure it was observed that some sequences cannot be synthesized, which is caused by the fact that, as a consequence of the ligation of an anchor molecule and a splinker molecule, a recognition site for a restriction enzyme is formed, which corresponds to the restriction enzyme of the splinker molecule and/or the anchor molecule as a consequence of which another cleavage would occur than would be necessary for the correct extension of an anchor and/or a splinker molecule.

According to the invention this restriction of the use of the Sloning procedure is circumvented by the fact that the additional recognition sites for either the anchor or the splinker-specific type IIS restriction enzyme, resulting from the specific combination of anchor and splinker sequence, are methylated and thus cannot be cut. The recognition sequences in the constant regions of the splinker and/or anchor that are necessary for carrying out the Sloning procedure, however, are not methylated and can therefore still be cut.

Specifically, one proceeds in such a way that, in the context of a sequential ligation of partially methylated splinker molecules from a library, it is intended that the 5' overhang sequences ((5'→3') GTC, CTC, TCT) and the following 3' terminal sequences (AGA, ACG, GAC) are methylated. In step (A) the anchor molecule carrying a modification, which allows a coupling to a solid matrix, has a methylation at the adenosine in its overhang. The splinker molecule complementary to the anchor molecule likewise exhibits a methylation in its overhang, in the present case at the cytosine. It is within the scope of the present invention that a Methylierung is also possible in other parts than the overhangs, as long as thereby one of the two necessary recognition sites for a type IIS restriction enzyme is not functionally inactivated.

After the ligation of the two molecules the ligation product shown in (A) is obtained, which is cleaved, after removing the ligase, with the splinker-specific type IIS restriction endonuclease. As a consequence of this cleavage, the anchor molecule is elongated and now exhibits a methylation in the two strands of double strand. To the thus obtained elongated anchor molecule a further splinker molecule is ligated, whereby the splinker molecule leads to the fact that in the ligation product obtained in step (C) a further recognition site is formed for the Splinker specific restriction enzyme beside the splinker-specific restriction enzyme recognition site, contained in the splinker molecule. As shown in (C), still another recognition site for Eco31I would thereby be created beside the recognition site for Eco31I in the splinker molecule in the ligation region indicated in the present example, with the consequence, that when using Eco31I, after removing the Ligase, three cleavage products would typically be formed. However, as a consequence of the methylation of the second recognition site for Eco31I formed by the ligation of the splinker molecule and the anchor molecule, this site is not accessible for the splinker-specific restriction enzyme. Consequently Eco31I cuts this ligation product only proximal to the splinker, but not distal to it. Therefore the anchor molecule can be correctly elongated and be used for the further synthesis in the context of the Sloning procedure.

FIG. 23 shows a procedure for the (intermediate) product amplification as it can be carried out in any step of the Sloning procedure. Typically, the (intermediate) product amplification occurs with ligation products arising in the context of the Sloning procedure, as e.g. in the context of the so-called elongation synthesis (i.e. one or more cycles of steps aa) to ag) or ba) to bg), respectively or in the context of the transpositions. Such (intermediate) product amplifications are especially useful when the concentration of an (intermediate) product has become so low that an efficient execution of the following steps is endangered.

The (intermediate) product amplification is carried out by a procedure known in the art as polymerase chain reaction. Thereby one proceeds in such a way that oligonucleotide primers complementary to the splinker and the anchor are annealed to a ligation product generated in the context of the Sloning procedure. Preferably, the primers are complementary to the constant region of the anchor or splinker molecule, respectively or a part thereof. The advantage of such a primer design is that one pair of primers is sufficient to carry out the amplification of the product or an intermediate, respectively irrespective of the nucleic acid assembled, i.e. the target sequence or a part thereof. However, it is likewise possible and within the scope of the present invention that the primers bind, partially or completely, to a region of the anchor or splinker molecule corresponding to the assembled nucleic acid. The term "complementary" is to be understood in such a way that a nucleic acid interacts with another nucleic acid via base pairing. It is acknowledged by those skilled in the art that "complementary" does not necessarily imply complete complementarity. Rather one or more false base pairs may be contained, and one or more nucleotides may not be base-paired.

When selecting the primers, it should be kept in mind that preferably they should not be self-complementary. Consequently, the primers used in this procedure preferably hybridise only with 3 or 4 nucleotides of the clamp (the constant double-stranded region directly abutting the loop), the loop region of the anchor or splinker molecule itself, as well as the following nucleotides (to the maximum to the end of the constant region of the 5' overhang of the anchor molecule or the splinker molecule, respectively (A)). After annealing the anchor- and splinker-specific primers, an amplification of the internal gene fragments is carried out with a thermostable polymerase, which preferably possesses a proof-reading function. Typically, primers are added to the reaction in large excess. In case a continued synthesis is intended using the thus amplified (intermediate) product, one preferably uses modified oligonucleotides as primers, which allow to bind the oligonucleotides to a solid matrix. The result of the (intermediate) product amplification no longer possesses a loop structure connecting the strand and the opposite strand. Instead the amplified ligation product is present as a double-strand structure of two single strands. These molecules, herein also described as bipartite structure, can likewise be used as educts.

It is within the scope of the present invention that the various aspects can be combined with each other at will, and thus a multitude of embodiments of the Sloning procedure are possible.

The features of the invention disclosed in the fore-going description, the claims and the figures may be essential both individually as well as in any desired combination for the realization of the invention in its various embodiments.

What is claimed is:

1. A method comprising the steps:
   a) providing a sequence of a defined nucleic acid molecule to be synthesized,
   b) providing an oligonucleotide produced by the following steps:
      ba) providing a partially double-stranded first oligonucleotide with a 5'-overhang comprising a recognition site for a first type IIS restriction enzyme which cuts outside of its recognition site, wherein the first oligonucleotide comprises a modification which allows coupling to a solid matrix, wherein the 5'-overhang has a length of 3 nucleotides,
      bb) providing a partially double-stranded second oligonucleotide with a 5'-overhang comprises a recognition site for a second type IIS restriction enzyme which cuts outside of its recognition site, the recognition site for the first and second type IIS restriction enzymes being different, wherein the 5'-overhang has a length of 3 nucleotides,
      bc) ligating the first and second oligonucleotides from steps ba) and bb) in the orientation defined by the blocking of the ends not to be ligated,
      bd) removing unconsumed reactants as well as enzymes,
      be) cleaving the ligation product from step bc) with the second type IIS restriction enzyme which cuts outside of its recognition site, wherein the cleavage occurs in the nucleic acid sequence of the second oligonucleotide from step bb), creating a first elongated product, wherein the first elongated product comprises the first oligonucleotide from step ba) which has been elongated, bf) separating the reaction mixture from the first elongated product,
   c) providing a further oligonucleotide produced by the following steps:
      ca) providing a partially double-stranded third oligonucleotide with a 5'-overhang, comprising a recognition site for a third type IIS restriction enzyme which cuts outside of its recognition site, wherein the third oligonucleotide comprises a modification which allows coupling to a solid matrix, wherein the 5'-overhang has a length of 3 nucleotides,
      cb) providing a partially double-stranded fourth oligonucleotide with a 5'-overhang comprising a recognition site for a fourth type IIS restriction enzyme which cuts outside of its recognition site, the recognition sites of the third and fourth type IIS restriction enzymes being different, wherein the 5'-overhang has a length of 3 nucleotides,
      cc) ligating the third and fourth oligonucleotides from steps ca) and cb) in the orientation defined by the blocking of the ends not to be ligated,
      cd) removing unconsumed reactants as well as enzymes,
      ce) cleaving the ligation product from step cc) with the fourth type IIS restriction enzyme, which cuts outside of its recognition site, whereby the cleavage occurs in the fourth oligonucleotide in step cb), creating a second elongated product, wherein the second elongated product comprises the third oligonucleotide from step ca) which has been elongated,
      cf) separating the reaction mixture from the second elongated product,
   d) ligating the first and second elongated products from steps b) and c) in the orientation defined by the blocking of the ends not to be ligated,
   e) removing unconsumed reactants as well as enzymes,
   f) cleavage of the ligation product from step d) with a type IIS restriction enzyme which cuts outside of its recognition site, whereby the cleavage occurs in the first or second elongated product from steps b) or c), thus creating a third elongated product,
   g) separating the third elongated product from the reaction mixture, characterized in that the second oligonucleotide from step bb) has the recognition site for a type IIS restriction enzyme which generates an overhang three nucleotides in length as long as steps bb) to be) are repeated and the second oligonucleotide from step bb) has the recognition site for a type IIS restriction enzyme which generates an overhang other than an overhang three nucleotides in length, in the last cycle of the steps bb) to be) and/or the fourth oligonucleotide from step cb) has the recognition site for a type IIS restriction enzyme which generates an overhang three nucleotides in length, as long as steps cb) to ce) are repeated and the fourth oligonucleotide from step cb) has the recognition site of a type IIS restriction enzyme, which produces an overhang other than an overhang three nucleotides in length, in the last cycle of the steps cb) to ce) and
   h) isolating the nucleic acid molecule or part thereof having the sequence provided in step a).

2. The method according to claim 1, characterized in that, following step bf), steps bb) to bf) are repeated at least once and/or, following step cf), steps cb) to ce) are repeated at least once, whereby, following the final ligation in step cc) and the removing of unconsumed reactants as well as enzymes, the final ligation product is cut with a type IIS restriction enzyme, whereby the cleavage occurs in the third oligonucleotide from step ca).

3. A method comprising the steps:
   a) providing a sequence of a defined nucleic acid molecule to be synthesized,
   b) providing an oligonucleotide produced by the following steps:
      ba) providing a partially double-stranded first oligonucleotide comprising a 5' overhang and a recognition site for a first type IIS restriction enzyme which cuts outside of its recognition site, wherein the 5' overhang has a length of 3 nucleotides,
      bb) providing a partially double-stranded second oligonucleotide comprising a 5' overhang and a recognition site for a second type IIS restriction enzyme which cuts outside of its recognition site, the recognition sites of the first and second type IIS restriction enzymes being different, wherein the second oligonucleotide comprises a modification allowing coupling to a solid matrix, wherein the 5' overhang has a length of 3 nucleotides, bc) ligating the first and second oligonucleotides from steps ba) and bb) in the orientation defined by the blocking of the ends not to be ligated, bd) cleaving the ligation product from step be) with the second type IIS restriction enzyme which cuts outside of its recognition site, wherein the cleavage occurs in the nucleic acid sequence of the second oligonucleotide from step bb), creating a first elongated product, wherein the first elongated product comprises the first oligonucleotide from step ba) which has been elongated, bf) separating from the reaction mixture the first elongated product, c) providing a further oligonucleotide produced by the following steps:

ca) providing a third oligonucleotide comprising a 5' overhang and a recognition site for a third type IIS restriction enzyme, wherein the 5' overhang has a length of 3 nucleotides, cb) providing a partially double-stranded fourth oligonucleotide comprising a 5' overhang and a recognition site for a fourth type IIS restriction enzyme which cuts outside of its recognition site, the recognition sites of the third and fourth type IIS restriction enzymes being different, wherein the fourth oligonucleotide comprises a modification which allows coupling to a solid matrix, wherein the 5' overhang has a length of 3 nucleotides, cc) ligating the third and fourth oligonucleotides from steps ca) and cb) in the orientation defined by the blocking of the ends not to be ligated, ce) cleaving the ligation product from step cc) with a fourth type IIS restriction enzyme which cuts outside of its recognition site, whereby the cleavage occurs in the fourth oligonucleotide from step cb), creating a second elongated product, wherein the second elongated product comprises the third oligonucleotide from step ca) which has been elongated, cf) separating from the reaction mixture the second elongated product from step ce), d) ligating the first and second elongated products from steps b) and c) in the orientation defined by the blocking of the ends not to be ligated, e) removing and/or inactivating unconsumed reactants as well as enzymes, f) cleaving the ligation product from step d) with a type IIS restriction enzyme which cuts outside of its recognition site, whereby the cleavage occurs in the first or second elongated product from steps b) or c), creating a third elongated product, g) separating the third elongated product from the reaction mixture, and h) isolating the nucleic acid molecule or part thereof having the sequence provided in step a).

4. The method according to claim 3, characterized in that, following step bc), as step bd), unconsumed reactants as well as enzymes are removed and/or, following step bf), steps bb) to bf) are repeated at least once and/or, following step cf), steps cb) to cf) are repeated at least once, whereby, following the final ligation in step cc) and the removing and/or inactivating of unconsumed reactants as well as enzymes, the ligation product is cut using a third type IIS restriction enzyme, whereby the cleavage occurs in the third oligonucleotide from step ca).

5. The method according to claim 3, further comprising the step of transferring cleavage products that do not contain a modification to a new reaction.

6. The method according to claim 3, whereby step cd) follows step cc), and comprises cd) removing and/or inactivating unconsumed reactants as well as enzymes.

7. A method comprising the steps:

a) providing a sequence of a defined nucleic acid molecule to be synthesized, b) providing an oligonucleotide produced by the following steps:

ba) providing a first oligonucleotide comprising a 5' overhang and a recognition site for a first type IIS restriction enzyme which cuts outside of its recognition site, wherein the first oligonucleotide comprises a modification which allows coupling to a solid matrix, and coupling the first oligonucleotide to the solid matrix, wherein the 5' overhang has a length of 3 nucleotides, bb) providing a partially double-stranded second oligonucleotide comprising a 5' overhang and a recognition site for a second type IIS restriction enzyme which cuts outside of its recognition site, the recognition site for the first and second type II restriction enzymes being different, wherein the 5' overhang has a length of 3 nucleotides, bc) ligating the first and second oligonucleotides from steps ba) and bb) in the orientation defined by the blocking of the ends not to be ligated, bd) removing unconsumed reactants as well as enzymes, be) cleaving the ligation product from step be) with the second type IIS restriction enzyme which cuts outside of its recognition site, wherein the cleavage occurs in the nucleic acid sequence of the second oligonucleotide from step bb), creating a first elongated product, wherein the first elongated product comprises the first oligonucleotide from step ba) which has been elongated, bf) separating the reaction mixture from the first elongated product, c) providing a further oligonucleotide produced by the steps:

ca) providing a third oligonucleotide comprising a 5' overhang and a recognition site for a third type IIS restriction enzyme which cuts outside of its recognition site, wherein the third oligonucleotide comprises a modification which allows coupling to a solid matrix, coupling of the third oligonucleotide to the solid matrix, wherein the 5' overhang has a length of 3 nucleotides, cb) providing a partially double-stranded fourth oligonucleotide comprising a 5' overhang and a recognition site for a fourth type IIS restriction enzyme which cuts outside of its recognition site, the recognition site of the third and fourth type IIS restriction enzymes being different, wherein the 5' overhang has a length of 3 nucleotides, cc) ligation of the third and fourth oligonucleotides from steps ca) and cb) in the orientation defined by the blocking of the ends not to be ligated, cd) removing unconsumed reactants as well as enzymes, ce) cleavage of the ligation product from step cc) with the fourth type IIS restriction enzyme which cuts outside of its recognition site, whereby the cleavage occurs in the fourth oligonucleotide in step cb), creating a second elongated product, wherein the second elongated product comprises the third oligonucleotide from step ca) which has been elongated, cf) separating the second elongated product from the reaction mixture, d) ligating the first and second elongated products from steps b) and c) in the orientation defined by the blocking of the ends not to be ligated, e) removing unconsumed reactants as well as enzymes, f) cleavage of the ligation product from step d) with a type IIS restriction enzyme, which cuts outside of its recognition site, whereby the cleavage occurs in the first or second elongated product from steps b) or c), creating a third elongation product, g) separating the third elongation product from the reaction mixture, wherein the last repetition of steps bb) to bf) the first oligonucleotide added in step bb) carries a modification, which allows coupling to a solid matrix, and h) isolating the nucleic acid molecule or part thereof having the sequence provided in step a).

8. The method according to claim 7, wherein after the last repetition of steps bb) to bf), as step bh), the ligation product from step be) is cut with a type IIS restriction enzyme which cuts outside of its recognition site, whereby the cleavage occurs in the nucleic acid sequence of the first oligonucleotide from step ba) and the cleavage product is released from the oligonucleotide coupled to the solid matrix, and the released cleavage product is divided into at least two reactions.

9. The method according to claim 7, characterized in that, following step bf), steps bb) to bf) are repeated at least once and/or, following step cf), steps cb) to cf) are repeated at least once, whereby, following the final ligation in step cc) and the removing of unconsumed reactants as well as enzymes, the ligation product is cut with a type IIS restriction enzyme, whereby the cleavage occurs in the third oligonucleotide from step ca).

10. The method according to claim 7, characterized in that the cleavage product released in step bh) is coupled to a solid matrix via the modification, and that the cleavage products that do not contain the modification are removed from the reaction.

11. The method according to claim 10, characterized in that, as step bi), in each of the reactions an oligonucleotide is added to the cleavage product coupled to the solid matrix from step bh), whereby the oligonucleotide contains a recognition site for a type IIS restriction enzyme which is different from the recognition site of a type IIS restriction enzyme of the cleavage product from step bh), with the oligonucleotide carrying a modification which allows coupling to a solid matrix, and, as step bk), the cleavage product from step bh) is ligated with the oligonucleotide.

12. The method according to claim 11, characterized in that the ligation product from step bk) is cut with a type IIS restriction enzyme which cuts outside of its recognition site, whereby the cleavage occurs in the nucleic acid sequence of the cleavage product from step bh).

13. The method according to claim 11, characterized in that the oligonucleotide added in step bi) has a different sequence in each reaction.

14. The method according to claim 7, characterized in that the oligonucleotides added to the reactions have identical single-stranded overhangs.

15. The method according to claim 7, characterized in that the oligonucleotides differ in a region that is different from the single-stranded region, preferably in a region comprising a sequence of nucleotides following the single-stranded region of the oligonucleotide.

16. The method according to claim 15, characterized in that the sequence of nucleotides has a length of 1 to 10 nucleotides, preferably 3 to 6 nucleotides.

17. The method according claim 7, characterized in that, in a step al), the oligonucleotide added in step bi) is cleaved.

18. The method according to claim 17, characterized in that the steps bb) to bk) and/or bl) are repeated at least once.

19. The method according to claim 18, characterized in that, after the last repetition, the oligonucleotides coupled to the solid phases are ligated, as step bm), with a further oligonucleotide according to bb), whereby these oligonucleotides in the different reactions differ from each other in the sequence of the single-stranded overhang and optionally in the sequence of the directly abutting double-stranded region.

20. The method according to claim 7, characterized in that, to the cleavage product coupled to the solid matrix from step bh), an oligonucleotide is added which contains a recognition site for a type IIS restriction enzyme that is different from the recognition site for a type IIS restriction enzyme of the cleavage product from step bh), the oligonucleotide carrying a modification which allows coupling to a solid matrix, and that, as step bi), the cleavage product from step bh) is ligated with the oligonucleotide.

21. The method according to claim 20, characterized in that the ligation product from step bi) is cut with a type IIS restriction enzyme which cuts outside of its recognition site, whereby the cleavage occurs in the nucleic acid sequence of the cleavage product from step bh).

* * * * *